US008383636B2

(12) United States Patent
Clinch et al.

(10) Patent No.: US 8,383,636 B2
(45) Date of Patent: Feb. 26, 2013

(54) ACYCLIC AMINE INHIBITORS OF 5-METHYTIOADENOSINE PHOSPHORYLASE AND NUCLEOSIDASE

(75) Inventors: Keith Clinch, Lower Hutt (NZ); Gary Brian Evans, Lower Hutt (NZ); Richard Frohlich, Vienna (AT); Richard Hubert Furneaux, Wellington (NZ); Peter Michael Kelly, Wellington (NZ); Jennifer Mary Mason, Lower Hutt (NZ); Vern L. Schramm, New Rochelle, NY (US); Peter Charles Tyler, Wellington (NZ); Shivall Ashwah Ashwin Gulab, Wellington (NZ)

(73) Assignees: Industrial Research Limited, Lower Hutt (NZ); Albert Einstein College of Medicine of Yeshiva University, Bronx, NY (US)

( * ) Notice: Subject to any disclaimer, the term of this patent is extended or adjusted under 35 U.S.C. 154(b) by 235 days.

(21) Appl. No.: 12/310,597

(22) PCT Filed: Sep. 7, 2007

(86) PCT No.: PCT/NZ2007/000260
§ 371 (c)(1),
(2), (4) Date: Nov. 5, 2010

(87) PCT Pub. No.: WO2008/030118
PCT Pub. Date: Mar. 13, 2008

(65) Prior Publication Data
US 2011/0046167 A1  Feb. 24, 2011

Related U.S. Application Data

(60) Provisional application No. 60/842,900, filed on Sep. 7, 2006.

(51) Int. Cl.
C07D 487/04 (2006.01)
A61K 31/519 (2006.01)
A61P 35/00 (2006.01)
(52) U.S. Cl. .................. 514/265.1; 544/280
(58) Field of Classification Search .............. 544/280; 514/265.1
See application file for complete search history.

(56) References Cited

U.S. PATENT DOCUMENTS

| 5,985,848 | A  | 11/1999 | Furneaux et al. |
| 6,066,722 | A  | 5/2000  | Furneaux et al. |
| 6,228,847 | B1 | 5/2001  | Furneaux et al. |
| 6,379,911 | B2 | 4/2002  | Schramm et al. |
| 6,458,799 | B1 | 10/2002 | Montgomery et al. |
| 6,492,347 | B2 | 12/2002 | Furneaux et al. |
| 6,693,193 | B1 | 2/2004  | Furneaux et al. |
| 6,764,829 | B2 | 7/2004  | Schramm et al. |
| 6,803,455 | B2 | 10/2004 | Furneaux et al. |
| 7,022,852 | B2 | 4/2006  | Furneaux et al. |
| 7,098,334 | B2 | 8/2006  | Furneaux et al. |
| 7,109,331 | B2 | 9/2006  | Furneaux et al. |
| 7,211,653 | B2 | 5/2007  | Furneaux et al. |
| 7,211,677 | B2 | 5/2007  | Furneaux et al. |
| 7,390,890 | B2 | 6/2008  | Furneaux et al. |
| 7,405,297 | B2 | 7/2008  | Furneaux et al. |
| 7,528,140 | B2 | 5/2009  | Kataoka et al. |
| 7,553,839 | B2 | 6/2009  | Evans et al. |
| 7,655,795 | B2 | 2/2010  | Evans et al. |
| 7,777,025 | B2 | 8/2010  | Schramm et al. |
| 8,173,662 | B2 | 5/2012  | Evans et al. |
| 8,183,019 | B2 | 5/2012  | Lenz et al. |
| 2004/0110772 | A1 | 6/2004 | Furneaux |
| 2006/0160765 | A1 | 7/2006 | Evans et al. |
| 2006/0217551 | A1 | 9/2006 | Evans et al. |
| 2007/0275988 | A1 | 11/2007 | Schramm |
| 2008/0280334 | A1 | 11/2008 | Lenz et al. |
| 2009/0012104 | A1 | 1/2009 | Babu et al. |
| 2009/0192138 | A1 | 7/2009 | Baeschlin et al. |
| 2009/0227532 | A1 | 9/2009 | Furneaux et al. |
| 2009/0233948 | A1 | 9/2009 | Evans et al. |
| 2009/0239885 | A1 | 9/2009 | Evans et al. |
| 2009/0325986 | A1 | 12/2009 | Furneaux et al. |
| 2010/0062995 | A1 | 3/2010 | Schramm |
| 2010/0094003 | A1 | 4/2010 | Evans et al. |
| 2010/0168141 | A1 | 7/2010 | Evans et al. |
| 2010/0222370 | A1 | 9/2010 | Schramm et al. |
| 2011/0086812 | A1 | 4/2011 | Schramm |
| 2011/0092521 | A1 | 4/2011 | Furneaux et al. |
| 2011/0130412 | A1 | 6/2011 | Clinch et al. |
| 2011/0190265 | A1 | 8/2011 | Schramm |

FOREIGN PATENT DOCUMENTS

| EP | 1477489 A1 | 11/2004 |
| WO | WO 00/61783 | 10/2000 |
| WO | WO 02/18371 | 3/2002 |
| WO | WO 03/080620 A1 | 10/2003 |
| WO | WO 2004/018496 A1 | 3/2004 |
| WO | 2004065389 A1 | 8/2004 |
| WO | WO 2005/118532 | 12/2005 |
| WO | WO 2006/014913 A2 | 2/2006 |

(Continued)

OTHER PUBLICATIONS

PCT Notification Concerning Transmittal of International Preliminary Report on Patenetability dated Mar. 19, 2009 in connection with PCT International Patent Application No. PCT/NZ2007/00260, 2 pages.

Written Opinion of the International Searching Authority dated Dec. 13, 2007 in connection with PCT International Patent Application No. PCT/NZ2007000260, 3 pages.

(Continued)

Primary Examiner — Susanna Moore
(74) Attorney, Agent, or Firm — Amster, Rothstein & Ebenstein LLP

(57) ABSTRACT

The present invention relates to compounds of the general formula (I) which are inhibitors of 5'-methylthioadenosine phosphorylase or 5'-methylthioadenosine nucleosidase. The invention also relates to the use of these compounds in the treatment of diseases or conditions in which it is desirable to inhibit 5'-methylthioadenosine phosphorylase or 5'-methylthioadenosine nucleosidase including cancer, and to pharmaceutical compositions containing the compounds.

37 Claims, No Drawings

FOREIGN PATENT DOCUMENTS

| | | | |
|---|---|---|---|
| WO | WO 2006/123953 | A1 | 11/2006 |
| WO | WO 2007/016291 | A2 | 2/2007 |
| WO | 2007717738 | A1 | 6/2007 |
| WO | WO 2007/069923 | A1 | 6/2007 |
| WO | WO 2007/097647 | A1 | 8/2007 |
| WO | WO 2007/097648 | A1 | 8/2007 |
| WO | WO 2008/030119 | A1 | 3/2008 |
| WO | WO 2009/082247 | A1 | 7/2009 |
| WO | WO 2010/033236 | A2 | 3/2010 |
| WO | 2011008110 | A1 | 1/2011 |

OTHER PUBLICATIONS

PCT International Preliminary Report on Patentability and Written Opinion of the International Searching Authority in connection with PCT International.

Patent Application No. PCT/NZ2007/000260, 4 pages, mailing date Dec. 13, 2007.

Communication Supplemental European Search Report in connection with European Patent Application No. 07834862.0, 2 pages, completion date Jun. 16, 2010.

ACYCLIC AMINE INHIBITORS OF 5-METHYTIOADENOSINE PHOSPHORYLASE AND NUCLEOSIDASE

CROSS-REFERENCE TO RELATED APPLICATIONS

This application is a national stage entry under 35 U.S.C. §371 of PCT International Patent Application No. PCT/NZ2007/000260, filed Sep. 7, 2007, and claims priority to U.S. Provisional Patent Application No. 60/842,900, filed Sep. 7, 2006, the contents of which are incorporated herein by reference in their entirety.

STATEMENT OF GOVERNMENT SUPPORT

This invention was made with government support under grant number GM41916 awarded by the National Institutes of Health, U.S. Department of Health and Human Services. The government has certain rights in the invention.

TECHNICAL FIELD

This invention relates generally to certain nucleoside analogues, the use of these compounds as pharmaceuticals, pharmaceutical compositions containing the compounds, processes for preparing the compounds, and methods of treating diseases or conditions in which it is desirable to inhibit 5'-methylthioadenosine phosphorylase or 5'-methylthioadenosine nucleosidase.

BACKGROUND

U.S. Pat. No. 5,985,848, U.S. Pat. No. 6,066,722 and U.S. Pat. No. 6,228,741 describe nucleoside analogues that are inhibitors of purine nucleoside phosphorylases (PNPs) and purine phosphoribosyl-transferases (PRTs). The analogues are useful in treating parasitic infections, T-cell malignancies, autoimmune diseases and inflammatory disorders. The analogues are also useful for immunosupression in organ transplantation.

U.S. Pat. No. 6,693,193 describes a process for preparing certain PNP inhibitor compounds. This application recognises the compounds as PNP inhibitors and addresses a need for simpler methods of preparing them. U.S. Ser. No. 10/363,424 discloses further nucleoside analogues that are inhibitors of PNPs and PRTs.

PNPs catalyse the phosphorolytic cleavage of ribo- and deoxyribonucleosides, for example those of guanine and hypoxanthine, to give the corresponding sugar-1-phosphate and guanine, hypoxanthine or other purine bases.

Humans deficient in PNP suffer a specific T-cell immunodeficiency due to an accumulation of dGTP which prevents proliferation of stimulated T lymphocytes. Inhibitors of PNP are, therefore immunosuppressive, and are active against T-cell malignancies and T-cell proliferative disorders.

Nucleoside hydrolases (NHs) catalyse the hydrolysis of nucleosides. These enzymes are not found in mammals but are required for nucleoside salvage in some protozoan parasites. Some protozoan parasites use nucleoside phosphorylases either instead of or in addition to nucleoside hydrolases for this purpose. Inhibitors of nucleoside hydrolases and phosphorylases can be expected to interfere with the metabolism of the parasite and can therefore be usefully employed against protozoan parasites.

5'-Methylthioadenosine phosphorylase (MTAP) and 5'-methylthioadenosine nucleosidase (MTAN) function in the polyamine biosynthesis pathway, in purine salvage in mammals, and in the quorum sensing pathways in bacteria. MTAP catalyses the reversible phosphorolysis of methylthioadenosine (MTA) to adenine and 5-methylthio-$\alpha$-D-ribose-1-phosphate (MTR-1P). MTAN catalyses the reversible hydrolysis of MTA to adenine and 5-methylthio-$\alpha$-D-ribose, and of S-adenosyl-L-homocysteine (SAH) to adenine and S-ribosyl-homocysteine (SRH). The adenine formed is subsequently recycled and converted into nucleotides. Essentially, the only source of free adenine in the human cell is a result of the action of these enzymes. The MTR-1P is subsequently converted into methionine by successive enzymatic actions.

MTA is a by-product of the reaction involving the transfer of an aminopropyl group from decarboxylated S-adenosylmethionine to putrescine during the formation of spermidine. The reaction is catalyzed by spermidine synthase. Likewise, spermine synthase catalyses the conversion of spermidine to spermine, with concomitant production of MTA as a by-product. The spermidine synthase is very sensitive to product inhibition by accumulation of MTA. Therefore, inhibition of MTAP or MTAN severely limits the polyamine biosynthesis and the salvage pathway for adenine in the cells.

Although MTAP is abundantly expressed in normal cells and tissues, MTAP deficiency due to a genetic deletion has been reported with many malignancies. The loss of MTAP enzyme function in these cells is known to be due to homozygous deletions on chromosome 9 of the closely linked MTAP and p16/MTS1 tumour suppressor gene. As absence of p16/MTS1 is probably responsible for the tumour, the lack of MTAP activity is a consequence of the genetic deletion and is not causative for the cancer. However, the absence of MTAP alters the purine metabolism in these cells so that they are mainly dependent on the de novo pathway for their supply of purines.

MTA has been shown to induce apoptosis in dividing cancer cells, but to have the opposite, anti-apoptotic effect on dividing normal cells such as hepatocytes (E. Ansorena et al., Hepatology, 2002, 35: 274-280). MTAP inhibitors may therefore be used in the treatment of cancer. Such treatments are described in U.S. Ser. No. 10/395,636 and U.S. Ser. No. 10/524,995.

Compounds where the location of the nitrogen atom in the sugar ring is varied or where two nitrogen atoms form part of the sugar ring, have also been identified as inhibitors of MTAP and MTAN. These compounds are described in U.S. Ser. No. 10/524,995.

The need for new cancer therapies remains ongoing. For some prevalent cancers the treatment options are still limited. Prostate cancer, for example, is the most commonly diagnosed non-skin cancer in the United States. Current treatment options include radical prostatectomy, radiation therapy, hormonal therapy, and watchful waiting. Although the therapies may offer successful treatment of an individual's condition, the pitfalls are quite unfavorable and lead to a decrease in a man's overall quality of life. Surgery may inevitably result in impotence, sterility, and urinary incontinence. Side effects associated with radiation therapy include damage to the bladder and rectum as well as slow-onset impotence. Hormonal therapy will not cure the cancer and eventually most cancers develop a resistant to this type of therapy. The major risk associated with watchful waiting is that it may result in tumour growth, cancer progression and metastasis. It is therefore desirable that alternative treatment options are made available to patients diagnosed with prostate cancer.

MTAP and MTAN inhibitors may also be used in the treatment of diseases such as bacterial infections or protozoal parasitic infections, where it is desirable to inhibit MTAP/ MTAN. Such treatments are described in U.S. Ser. No. 10/395,636 and U.S. Ser. No. 10/524,995. However, the search continues for more effective treatments using these inhibitors.

The imino sugar part of the compounds described in the patent specifications referred to above has the nitrogen atom located between C-1 and C-4 so as to form 1,4-dideoxy-1,4-imino-D-ribitol compounds. The location of the nitrogen atom in the ribitol ring may be critical for binding to MTAP and MTAN enzymes. In addition, the location of the link between the sugar moiety and the nucleoside base analogue may be critical for enzyme inhibitory activity. The compounds described above have that link at C-1 of the sugar ring.

The applicants have also developed other MTAP and MTAN inhibitors, where the location of the nitrogen atom in the sugar ring is varied and, additionally, where two nitrogen atoms form part of the sugar ring. Alternative modes of linking the sugar part and the base analogue have also been investigated, resulting in a class of inhibitors where the sugar moiety is linked to the nucleoside base analogue via a methylene bridge. These other inhibitors are described in U.S. Ser. No. 10/395,636.

It has been considered to date that the three dimensional structure of the imino sugar ring of the above compounds is critical for effective binding to MTAP and MTAN, and therefore inhibition of these enzymes. The ring structure constrains the spatial locations that important functional groups, such as the imino nitrogen and various hydroxyl groups, can adopt when interacting with the enzymes. These steric constraints have previously been considered to be necessary for binding of the compounds in the active site of the enzymes. In the absence of such steric constraints, compounds would not be expected to be proficient binders to the enzyme active sites and consequently would not be effective inhibitors of the enzymes.

The view that the imino sugar ring is important for effective enzyme inhibition is reinforced in *J. Biol. Chem.*, 2005, 280, 30320-30328, which describes an investigation of transition state analogue interactions with human and *Plasmodium falciparum* PNPs. Inhibition activities against these PNPs for various nucleoside analogues are described. The structure of the great majority of the analogues contains an imino sugar ring. However, two compounds are described where that ring is, in effect, opened to give hydroxyethyl and hydroxypropyl substituents on the amino nitrogen.

The applicants surprisingly found that certain compounds analogous to the compounds described above, having an acyclic amine group rather than an imino ring, are effective inhibitors of PNPs. At least one such compound is a surprisingly potent inhibitor of human PNP.

Further investigations were carried out by the applicants into the enzyme inhibitory activity of structurally related compounds, in particular those having an amino group, rather than an hydroxy or alkoxy group, at the 4 position of the heterocyclic part of the compound structure. The applicants have now found that compounds of this type are effective inhibitors of MTAP and/or MTAN.

It is therefore an object of the present invention to provide acyclic amine compounds that are inhibitors of MTAP or MTAN, or to at least provide a useful choice.

STATEMENTS OF INVENTION

Accordingly, in a first aspect, the present invention provides a compound of the formula (I):

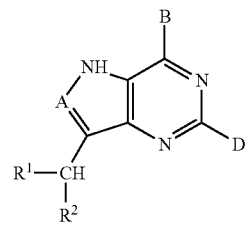

where:
R$^1$ is H or NR$^3$R$^4$;
R$^2$ is H or is an alkyl, alkenyl, alkynyl, aralkyl, aralkenyl, aralkynyl, or aryl group each of which is optionally substituted with one or more hydroxy, alkoxy, thiol, alkylthio, arylthio, aralkylthio, halogen, carboxylic acid, carboxylate alkyl ester, nitro, or NR$^3$R$^4$ groups, where each alkylthio, arylthio and aralkylthio group is optionally substituted with one or more alkyl, halogen, amino, hydroxy, or alkoxy groups;
provided that when R$^1$ is H, R$^2$ is an alkyl, alkenyl, alkynyl, aralkyl, aralkenyl, aralkynyl, or aryl group which is substituted with at least one NR$^3$R$^4$ group;
R$^3$ and R$^4$, independently of each other, is H or is an alkyl, alkenyl, alkynyl, aralkyl, aralkenyl, aralkynyl, or aryl group each of which is optionally substituted with one or more hydroxy, alkoxy, thiol, alkylthio, arylthio, aralkylthio, halogen, carboxylic acid, carboxylate alkyl ester, nitro, or NR$^3$R$^4$ groups, where each alkylthio, arylthio and aralkylthio group is optionally substituted with one or more alkyl, halogen, amino, hydroxy, or alkoxy groups;
A is N or CH;
B is NH$_2$ or NHR$^5$,
R$^5$ is an alkyl, alkenyl, alkynyl, aralkyl, aralkenyl, aralkynyl, or aryl group, each of which is optionally substituted with one or more halogen or hydroxy groups; and
D is H, OH, NH$_2$, or SCH$_3$;
or a tautomer thereof, or a pharmaceutically acceptable salt thereof, or an ester prodrug form thereof.
When R$^1$ is H then R$^2$ is preferably alkyl substituted with at least one NR$^3$R$^4$ group.
When R$^3$ or R$^4$ is optionally substituted alkyl, the alkyl group is preferably substituted by one or more hydroxy groups. For example, R$^3$ or R$^4$ may be hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxpentyl.
R$^3$ or R$^4$ may also preferably be alkyl substituted by one or more hydroxy groups and/or one or more optionally substituted thiol, alkylthio, arylthio, or aralkylthio groups For example, R$^3$ or R$^4$ may be methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl or methylthiotetrahydroxypentyl.
When R$^1$ is NR$^3$R$^4$, and R$^3$ and R$^4$ are H, R$^2$ is preferably an optionally substituted alkyl, more preferably an optionally substituted C$_1$-C$_5$ alkyl, for example, hydroxymethyl, hydroxyethyl, hydroxypropyl, dihydroxypropyl, hydroxybutyl, dihydroxybutyl, trihydroxybutyl, hydroxypentyl, dihydroxypentyl, trihydroxpentyl, methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl or methylthiotetrahydroxypentyl.

When $R^1$ is $NR^3R^4$, and $R^3$ is H and $R^4$ is an optionally substituted alkyl, $R^2$ is preferably H.

When $R^1$ is $NR^3R^4$, and $R^3$ is H and $R^4$ is an optionally substituted alkyl, $R^2$ is preferably an optionally substituted alkyl, more preferably an optionally substituted $C_1$-$C_5$ alkyl.

When $R^1$ is $NR^3R^4$, and $R^3$ and $R^4$ are each an optionally substituted alkyl, $R^2$ is preferably H.

Preferably A is CH. Alternatively, A may be N.

It is also preferred that B is $NH_2$.

It is further preferred that D is H. Alternatively, D may preferably be OH, $NH_2$ or $SCH_3$.

Preferred compounds of the invention include:
2-amino-7-(3,4-dihydroxy-5-(methylthiomethyl)pyrrolidin-2-yl)-4-amino-5H-pyrrolo[3,2-d]pyrimidine;
7-(3,4-dihydroxy-5-(methylthiomethyl)pyrrolidin-2-yl)-4-amino-5H-pyrrolo[3,2-d]pyrimidine;
2-amino-7-(2,3-dihydroxy-1-(2-(methylthio)ethylamino)propyl)-4-amino-5H-pyrrolo[3,2-d]pyrimidine;
7-(2,3-dihydroxy-1-(2-(methylthio)ethylamino)propyl)-4-amino-5H-pyrrolo[3,2-d]pyrimidine;
2-amino-7-(1-amino-2,3-dihydroxy-5-(methylthio)pentyl)-4-amino-5H-pyrrolo[3,2-d]pyrimidine;
7-(1-amino-2,3-dihydroxy-5-(methylthio)pentyl)-4-amino-5H-pyrrolo[3,2-d]pyrimidine;
2-amino-7-(2-hydroxy-1-(1-hydroxy-3-(methylthio)propan-2-ylamino)ethyl)-4-amino-5H-pyrrolo[3,2-d]pyrimidine;
7-(2-hydroxy-1-(1-hydroxy-3-(methylthio)propan-2-ylamino)ethyl)-4-amino-5H-pyrrolo[3,2-d]pyrimidine;
2-amino-7-((3,4-dihydroxy-1-(methylthio)butan-2-ylamino)methyl)-4-amino-5H-pyrrolo[3,2-d]pyrimidine;
7-((3,4-dihydroxy-1-(methylthio)butan-2-ylamino)methyl)-4-amino-5H-pyrrolo[3,2-d]pyrimidine;
2-amino-7-(((2-hydroxy-4-(methylthio)butyl)(methyl)amino)methyl)-4-amino-5H-pyrrolo[3,2-d]pyrimidine;
7-(((2-hydroxy-4-(methylthio)butyl)(methyl)amino)methyl)-4-amino-5H-pyrrolo[3,2-d]pyrimidine;
2-amino-7-((2-hydroxy-4-(methylthio)butylamino)methyl)-4-amino-5H-pyrrolo[3,2-d]pyrimidine;
7-((2-hydroxy-4-(methylthio)butylamino)methyl)-4-amino-5H-pyrrolo[3,2-d]pyrimidine;
2-amino-7-((3,4-dihydroxy-2-(methylthiomethyl)butylamino)methyl)-4-amino-5H-pyrrolo[3,2-d]pyrimidine;
7-((3,4-dihydroxy-2-(methylthiomethyl)butylamino)methyl)-4-amino-5H-pyrrolo[3,2-d]pyrimidine;
2-amino-74-(3-hydroxy-2-(methylthiomethyl)propylamino)methyl)-4-amino-5H-pyrrolo[3,2-d]pyrimidine;
7-((3-hydroxy-2-(methylthiomethyl)propylamino)methyl)-4-amino-5H-pyrrolo[3,2-d]pyrimidine;
7-(((3-hydroxy-2-(methylthiomethyl)propyl)(methyl)amino)methyl)-4-amino-5H-pyrrolo[3,2-d]pyrimidine;
2-amino-7-(((3-hydroxy-2-(methylthiomethyl)propyl)(methyl)amino)methyl)-4-amino-5H-pyrrolo[3,2-d]pyrimidine;
2-((4-amino-5H-pyrrolo[3,2-d]pyrimidin-7-yl)methylamino)-2-(methylthiomethyl)propane-1,3-diol;
(S)-1-((4-amino-5H-pyrrolo[3,2-d]pyrimidin-7-yl)methylamino)-3-(methylthio)propan-2-ol;
(R)-4-amino-5H-pyrrolo[3,2-d]pyrimidin-7-yl)methylamino)-3-(methylthio)propan-2-ol;
(2R,3S)-4-[(4-amino-5H-pyrrolo[3,2-d]pyrimidin-7-yl)methylamino]-3-(methylthiomethyl)butane-1,2-diol;
(2S,3S)-4-[(4-amino-5H-pyrrolo[3,2-d]pyrimidin-7-yl)methylamino]-3-(methylthiomethyl)butane-1,2-diol;
(2R,3S)-4-[(4-amino-5H-pyrrolo[3,2-d]pyrimidin-7-yl)methylamino]-3-(methylthiomethyl)butane-1,2-diol;
(2R,3S)-4-[(4-amino-5H-pyrrolo[3,2-d]pyrimidin-7-yl)methylamino]-3-(methylthiomethyl)butane-1,2-diol;
(2R,3R)-4-(((4-amino-5H-pyrrolo[3,2-d]pyrimidin-7-yl)methyl)(methyl)amino)-3-(methylthiomethyl)butane-1,2-diol;
(2S,3S)-4-(((4-amino-5H-pyrrolo[3,2-d]pyrimidin-7-yl)methyl)(methyl)amino)-3-(methylthiomethyl)butane-1,2-diol;
(2R,3S)-4-(((4-amino-5H-pyrrolo[3,2-d]pyrimidin-7-yl)methyl)(methyl)amino)-3-(methylthiomethyl)butane-1,2-diol;
(2S,3R)-4-(((4-amino-5H-pyrrolo[3,2-d]pyrimidin-7-yl)methyl)(methyl)amino)-3-(methylthiomethyl)butane-1,2-diol;
(2R,3R)-4-(((4-amino-5H-pyrrolo[3,2-d]pyrimidin-7-yl)methylamino)-4-(methylthio)butane-1,3-diol;
(2S,3S)-4-(((4-amino-5H-pyrrolo[3,2-d]pyrimidin-7-yl)methylamino)-4-(methylthio)butane-1,3-diol;
(2R,3S)-2-((4-amino-5H-pyrrolo[3,2-d]pyrimidin-7-yl)methylamino)-4-(methylthio)butane-1,3-diol;
(2S,3R)-2-((4-amino-5H-pyrrolo[3,2-d]pyrimidin-7-yl)methylamino)-4-(methylthio)butane-1,3-diol;
(2R,3R)-2-(((4-amino-5H-pyrrolo[3,2-d]pyrimidin-7-yl)methyl)(methyl)amino)-4-(methylthio)butane-1,3-diol;
(2S,3S)-2-(((4-amino-5H-pyrrolo[3,2-d]pyrimidin-7-yl)methyl)(methyl)amino)-4-(methylthio)butane-1,3-diol;
(2R,3S)-2-(((4-amino-5H-pyrrolo[3,2-d]pyrimidin-7-yl)methyl)(methyl)amino)-4-(methylthio)butane-1,3-diol;
(2S,3R)-2-(((4-amino-5H-pyrrolo[3,2-d]pyrimidin-7-yl)methyl)(methyl)amino)-4-(methylthio)butane-1,3-diol;
(2R,3R)-2-{[(4-amino-5H-pyrrolo[3,2-d]pyrimidin-7-yl)methylamino]methyl}-4-(methylthio)butane-1,3-diol;
(2S,3S)-2-{[(4-amino-5H-pyrrolo[3,2-d]pyrimidin-7-yl)methylamino]methyl}-4-(methylthio)butane-1,3-diol;
(2R,3S)-2-{[(4-amino-5H-pyrrolo[3,2-d]pyrimidin-7-yl)methylamino]methyl}-4-(methylthio)butane-1,3-diol;
(2S,3R)-2-{[(4-amino-5H-pyrrolo[3,2-d]pyrimidin-7-yl)methylamino]methyl}-4-(methylthio)butane-1,3-diol;
(2R,3R)-1-(((4-amino-5H-pyrrolo[3,2-d]pyrimidin-7-yl)methyl)(methyl)amino)-4-(methylthio)butane-2,3-diol;
(2S,3S)-1-(((4-amino-5H-pyrrolo[3,2-d]pyrimidin-7-yl)methyl)(methyl)amino)-4-(methylthio)butane-2,3-diol;
(2R,3S)-1-(((4-amino-5H-pyrrolo[3,2-d]pyrimidin-7-yl)methyl)(methyl)amino)-4-(methylthio)butane-2,3-diol;
(2S,3R)-1-(((4-amino-5H-pyrrolo[3,2-d]pyrimidin-7-yl)methyl)(methyl)amino)-4-(methylthio)butane-2,3-diol;
(R)-2-((R)-1-(4-amino-5H-pyrrolo[3,2-d]pyrimidin-7-yl)-2-hydroxyethylamino)-3-(methylthio)propan-1-ol;
(S)-2-((S)-1-(4-amino-5H-pyrrolo[3,2-d]pyrimidin-7-yl)-2-hydroxyethylamino)-3-(methylthio)propan-1-ol;
(R)-2-((S)-1-(4-amino-5H-pyrrolo[3,2-d]pyrimidin-7-yl)-2-hydroxyethylamino)-3-(methylthio)propan-1-ol; and
(S)-2-((R)-1-(4-amino-5H-pyrrolo[3,2-d]pyrimidin-7-yl)-2-hydroxyethylamino)-3-(methylthio)propan-1-ol.

In a second aspect of the invention there is provided a pharmaceutical composition comprising a pharmaceutically effective amount of a compound of formula (I).

In another aspect of the invention there is provided a method of treatment of a disease or condition in which it is desirable to inhibit 5'-methylthioadenosine phosphorylase or 5'-methylthioadenosine nucleosidase comprising administering a pharmaceutically effective amount of a compound of formula (I) to a patient requiring treatment.

The diseases or conditions include cancer and bacterial infections. More preferably the disease is prostate cancer or head and neck cancer.

In a further aspect of the invention there is provided the use of a compound of formula (I) in the manufacture of a medicament for the treatment of one or more of these diseases or conditions.

DETAILED DESCRIPTION

Definitions

The term "alkyl" means any saturated hydrocarbon radical having up to 30 carbon atoms and includes any $C_1$-$C_{25}$, $C_1$-$C_{20}$, $C_1$-$C_{10}$, or $C_1$-$C_6$ alkyl group, and is intended to include both straight- and branched-chain alkyl groups. The same terminology applies to the non-aromatic moiety of an aralkyl radical. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group and 1-methyl-2-ethylpropyl group.

The term "alkenyl" means any hydrocarbon radical having at least one double bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkenyl group, and is intended to include both straight- and branched-chain alkenyl groups. The same terminology applies to the non-aromatic moiety of an aralkenyl radical. Examples of alkenyl groups include: ethenyl group, n-propenyl group, iso-propenyl group, n-butenyl group, iso-butenyl group, sec-butenyl group, t-butenyl group, n-pentenyl group, 1,1-dimethylpropenyl group, 1,2-dimethylpropenyl group, 2,2-dimethylpropenyl group, 1-ethylpropenyl group, 2-ethylpropenyl group, n-hexenyl group and 1-methyl-2-ethylpropenyl group.

The term "alkynyl" means any hydrocarbon radical having at least one triple bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkynyl group, and is intended to include both straight- and branched-chain alkynyl groups. The same terminology applies to the non-aromatic moiety of an aralkynyl radical. Examples of alkynyl groups include: ethynyl group, n-propynyl group, iso-propynyl group, n-butynyl group, iso-butynyl group, sec-butynyl group, t-butynyl group, n-pentynyl group, 1,1-dimethylpropynyl group, 1,2-dimethylpropynyl group, 2,2-dimethylpropynyl group, 1-ethylpropynyl group, 2-ethylpropynyl group, n-hexynyl group and 1-methyl-2-ethylpropynyl group.

The term "aryl" means an aromatic radical having 4 to 18 carbon atoms and includes heteroaromatic radicals. Examples include monocyclic groups, as well as fused groups such as bicyclic groups and tricyclic groups. Some examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "aralkyl" means an alkyl radical having an aryl substituent.

The term "alkoxy" means an hydroxy group with the hydrogen replaced by an alkyl group.

The term "halogen" includes fluorine, chlorine, bromine and iodine.

The term "optionally substituted" means, in reference to the optionally substituted group, the group may have one or more substituents chosen from the group comprising hydroxy, alkyl, alkoxy, thiol, optionally substituted alkylthio, optionally substituted arylthio, optionally substituted aralkylthio, halogen, amino, carboxylic acid, and carboxylate alkyl ester.

The term "prodrug" as used herein means a pharmacologically acceptable derivative of the compound of formula (I), such that an in vivo biotransformation of the derivative gives the compound as defined in formula (I). Prodrugs of compounds of formula (I) may be prepared by modifying functional groups present in the compounds in such a way that the modifications are cleaved in vivo to give the parent compound.

The term "pharmaceutically acceptable salts" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

The term "patient" includes human and non-human animals.

Description of Inhibitor Compounds

The acyclic amine compounds of the invention are inhibitors of MTAP and/or MTAN. Based on their particular knowledge of PNPs, MTAP and MTAN, and the enzyme inhibitory activities of the imino ring compounds, the applicants would not have predicted that acyclic amine compounds would be potent PNP inhibitors. It was previously considered that a sterically unconstrained acyclic amine, rather than an imino ring, would have rendered acyclic amine compounds much less potent than their cyclic amine counterparts. However, certain related compounds, having a hydroxyl group for B rather than an amino moiety, were found to be surprisingly potent inhibitors of human PNP. Indeed, one compound has a $K_i^*$ for human PNP of 8.5±0.6 pM, a potency sufficient to have therapeutic potential.

Investigations into the enzyme inhibitory activity of structurally related compounds, i.e. those having an amino group, rather than an hydroxy or alkoxy group, for B. The applicants found that compounds of this type are effective inhibitors of MTAP and/or MTAN.

Synthesis of Inhibitor Compounds

The compounds of the invention may be prepared by a variety of different methods. The following are representative non-limiting examples.

Compounds where $R^1$ is $NR^3R^4$ may be prepared by reacting an amine $NHR^5R^6$ (where $R^5$ and $R^6$ may be the same as $R^3$ and $R^4$ or protected versions thereof) with an aldehyde (e.g. formaldehyde) and a 9-deazapurine (e.g. 9-deazaadenine) in a Mannich reaction as shown in Scheme 1. The Mannich reaction is followed by deprotection, if necessary.

Alternatively reductive amination of an aldehyde with the amine NHR$^5$R$^6$ (as shown in Scheme 2) can be effected using reagents such as, but not limited to, NaBH$_3$CN or NaAcO$_3$BH. Conversion of the 4-t-butoxy- to 4-amino-5H-pyrrolo-[3,2-d]-pyrimidine may be effected as shown. Suitable deprotection steps follow. Suitable protected aldehydes are known (e.g. *J. Org. Chem.* 2004, 69, 2217-2220).

Reductive amination of the aldehyde of 4-choro compounds followed by conversion of the 4-chloro to the 4-amino- can be employed. An example is the preparation and reductive amination of 5-(benzyloxymethyl)-4-chloro-5H-pyrrolo[3,2-d]pyrimidine-7-carbaldehyde as shown in Scheme 3.

Another example is shown in Scheme 4. A carbonyl compound, where R$^7$ is an optionally substituted alkyl or protected version thereof and R$^8$ is H or an optionally substituted alkyl or protected version thereof, may be treated with a lithiated purine derivative (some examples of which may be found in *J. Org. Chem.* 2004, 69, 2217-2220). A standard deoxygenation step may be followed by conversion of the 4-hydroxy- to 4-amino-5H-pyrrolo-[3,2-d]-pyrimidine.

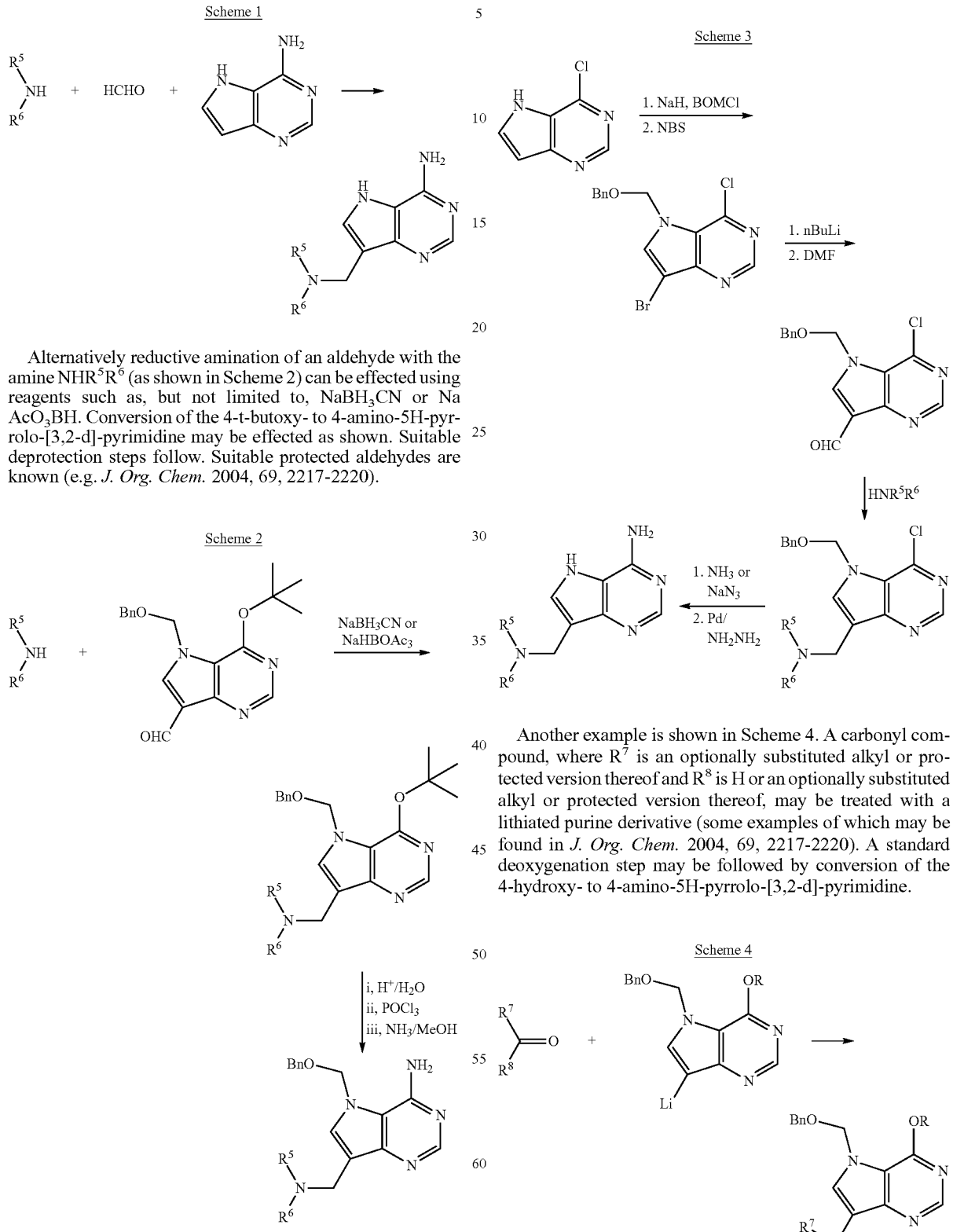

The amines NHR⁵R⁶ described above may be prepared by a number of methods. The following are representative non-limiting examples.

Cycloaddition of but-2-ene-1,4-diol with a nitrone derived from N-benzylhydroxylamine and formaldehyde (Scheme 5) followed by zinc reduction to give an amine that may be further functionalized to provide compounds of the invention.

Scheme 5

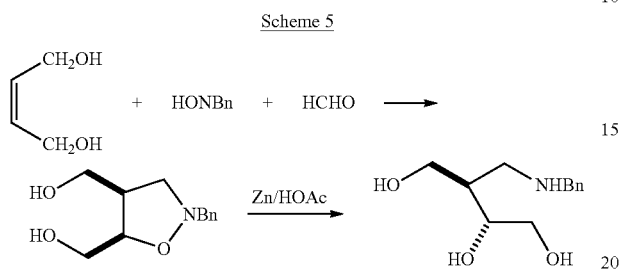

Conversion of butane 1,2,4-triol into either the 2,4-O-benzylidene or the 1,2-O-isopropylidene derivatives (Scheme 6). These compounds may then be converted into amines that can be further functionalized into compounds of the invention by activation of the primary hydroxy group, and displacement and appropriate manipulation of protecting groups.

Scheme 6

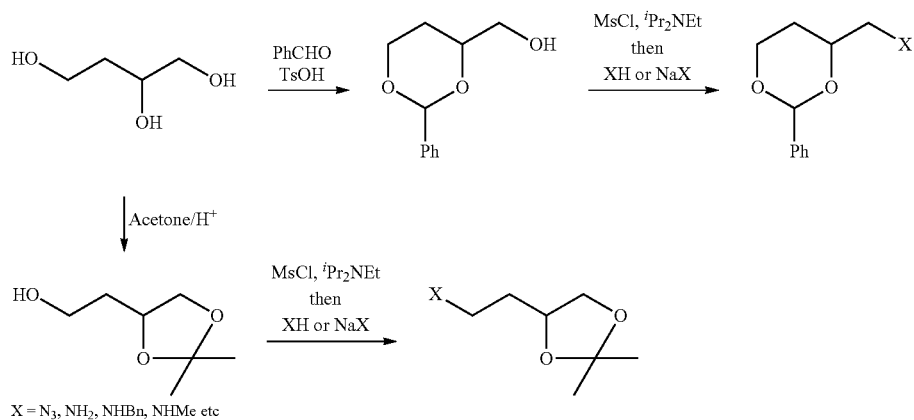

Compounds such as (R)- or (S)-(2,2-dimethyl-1,3-dioxolan-4-yl)methanol may be converted into amines using the chemistry described in Scheme 6, and the amines then converted into compounds of the invention.

But-2-ene 1,4-diol may be protected, epoxidized and ring opened as shown in Scheme 7 to give precursors to amines that may then be converted into compounds of the invention.

Scheme 7

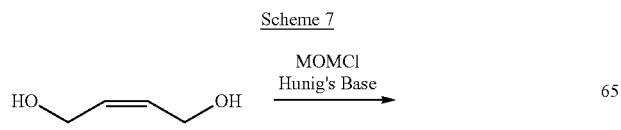

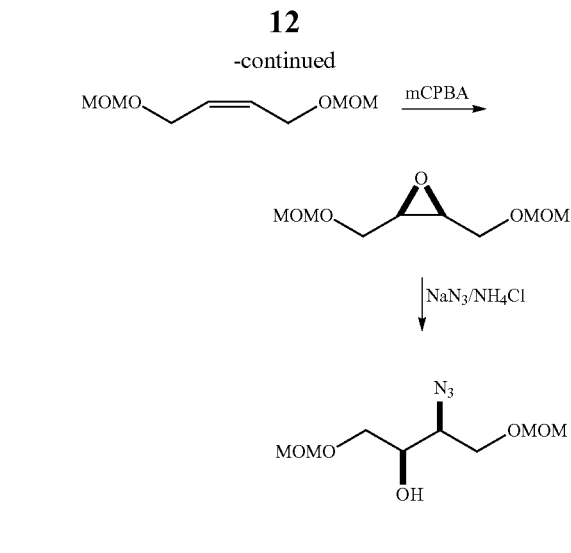

D- and L-Diethyl tartrate can be converted into chiral amines as shown in Scheme 8 (A. Breuning, R. Vicik and T. Schirmeister, *Tetrahedron Asymm.*, 2003, 14, 3301 and Z. Tang, Z.-H. Yang, X.-H. Chen, L.-F. Cun, A.-Q. Mi, Y.-Z. Jiang and L.-Z. Gong, *J. Am. Chem. Soc.*, 2005, 127, 9285) from which other useful amines may be derived.

Scheme 8

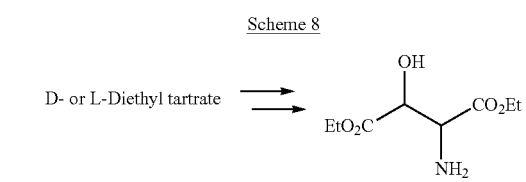 [SMILES: CCOC(=O)C(N)C(O)C(=O)OCC]

Reaction of 4,4-dimethyl-3,5,8-trioxabicyclo[5.1.0]octane with either enantiomer of α-methylbenzylamine (J. Org. Chem. 1998, 63, 7582-7583) affords diastereomeric mixtures of amino alcohols (Scheme 9). Crystallisation of the desired diastereomer followed by hydrogenolysis provides access to the enantiomerically pure amino alcohol.

Scheme 9

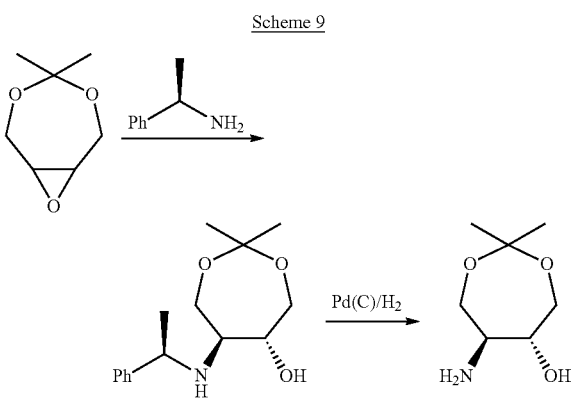

Various protected lactones and esters can be treated with ammonia to give amido alcohols, which can be converted to the corresponding amino alcohols on treatment with lithium aluminium hydride (Scheme 10).

Scheme 10

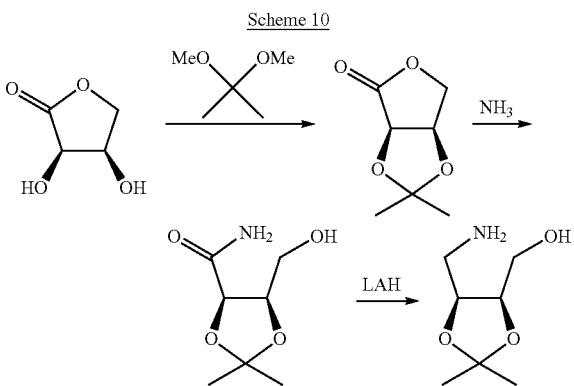

General Aspects

The compounds of the invention are useful in both free base form and in the form of salts.

It will be appreciated that the compounds of the invention include all optical isomers and stereoisomers of the formula (I).

The active compounds may be administered to a patient by a variety of routes, including orally, parenterally, by inhalation spray, topically, rectally, nasally, buccally or via an implanted reservoir. The amount of compound to be administered will vary widely according to the nature of the patient and the nature and extent of the disorder to be treated. Typically the dosage for an adult human will be in the range less than 1 to 1000 milligrams, preferably 0.1 to 100 milligrams. The specific dosage required for any particular patient will depend upon a variety of factors, including the patient's age, body weight, general health, sex, etc.

For oral administration the compounds can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant.

The compounds may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

EXAMPLES

The following examples further illustrate the invention. It is to be appreciated that the invention is not limited to the examples.

General Methods

Anhydrous solvents were obtained commercially. Air sensitive reactions were carried out under argon. Organic solutions were dried over $MgSO_4$ and the solvents were evaporated under reduced pressure. Chromatography solvents were distilled prior to use. Thin layer chromatography (t.l.c.) was performed on glass or aluminium sheets coated with 60 $F_{254}$ silica. Organic compounds were visualised under uv light or by use of a dip of cerium(IV) sulfate (0.2%, w/v) and ammonium molybdate (5%) in sulfuric acid (2M), one of $I_2$ (0.2%) and KI (7%) in $H_2SO_4$ (M), or 0.1% ninhydrin in EtOH. Flash column chromatography was performed on Scharlau or Merck silica gel 60 (40-60 μm). Optical rotations were recorded on a Perkin-Elmer 241 polarimeter with a path length of 1 dm and are in units of $10^{-1}$ deg $cm^2$ $g^{-1}$; concentrations are in g/100 ml. NMR spectra were recorded on a Bruker AC300E. Unless otherwise stated, $^1H$ spectra at 300 MHz were measured in $CDCl_3$, $CD_3OD$ (internal reference $Me_4Si$, δ 0) or $D_2O$ (no internal reference), and $^{13}C$ spectra at 75.5 MHz in $CDCl_3$ (reference, solvent centre line, δ 77.4), $CD_3OD$ (reference, solvent centre line δ 49.5) or $D_2O$ (no internal reference). Positive electrospray mass spectra were recorded on a Waters Q-TOF Premier Tandem Mass Spectrometer.

Example 1

2-((4-amino-5H-pyrrolo[3,2-d]pyrimidin-7-yl)methylamino)-2-(methylthiomethyl)propane-1,3-diol

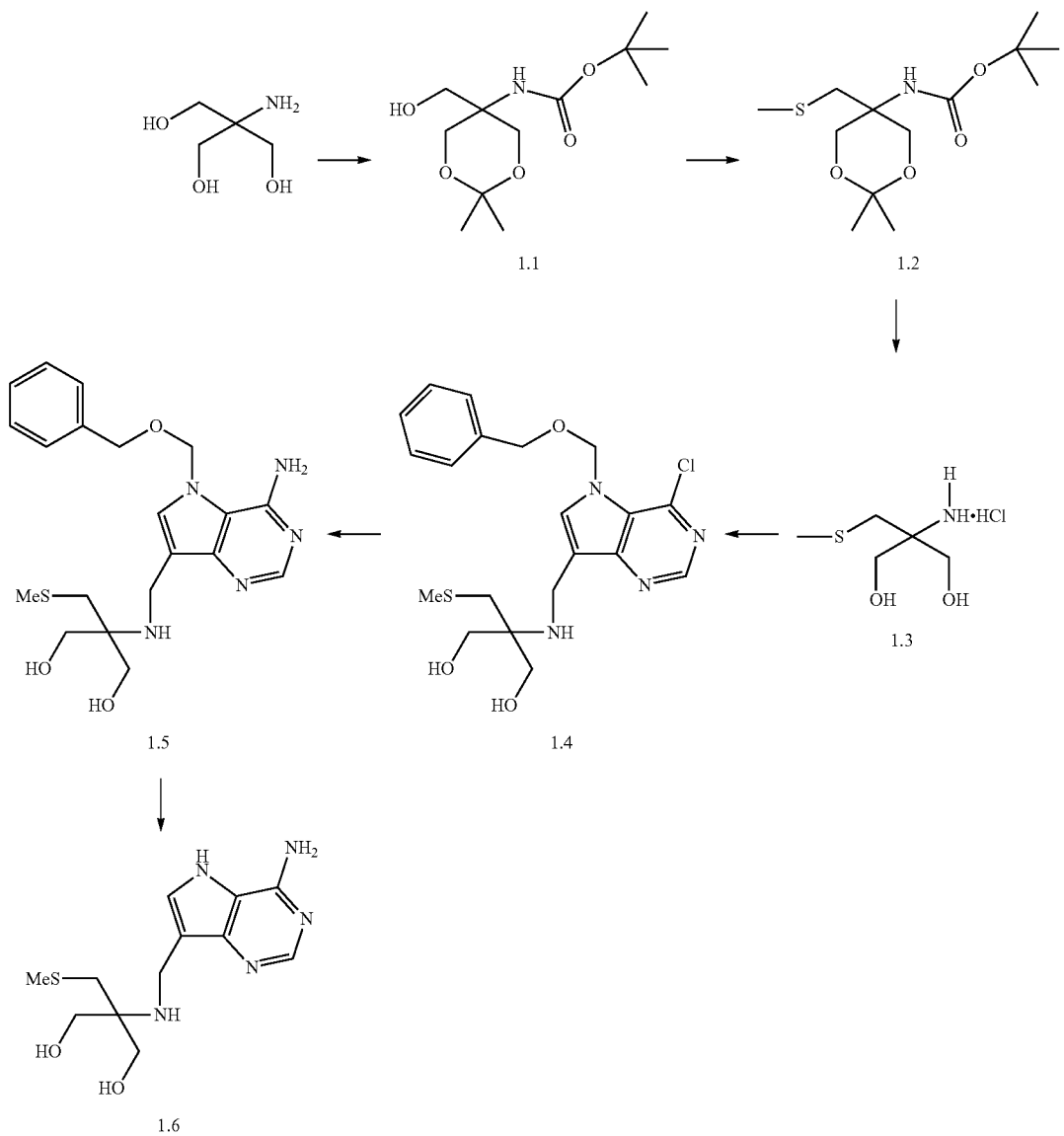

Example 1.1

Synthesis of N-(5-(hydroxymethyl)-2,2-dimethyl-1,3-dioxan-5-yl)pivalamide

A solution of 2-amino-2-(hydroxymethyl)propane-1,3-diol (15.7 g, 130 mmol) and di-tert-butyl dicarbonate (31.1 g, 143 mmol) in methanol (400 mL) and water (40 mL) was stirred at ambient temperature for 72 h. The contents of the flask were evaporated and the resulting white solid dissolved in minimal hot ethyl acetate and allowed to recrystallise overnight. The crystals were filtered and washed with petroleum ether to give N-(1,3-dihydroxy-2-(hydroxymethyl)propan-2-yl)pivalamide (26.5 g, 130 mmol, 100%) as fluffy, white needles. To a solution of N-(1,3-dihydroxy-2-(hydroxymethyl)propan-2-yl)pivalamide (9.50 g, 42.0 mmol) and 2,2-dimethoxypropane (16.0 mL, 129 mmol) in DMF (100 mL) was added pyridinium para-toluenesulfonate (0.540 g, 2.15 mmol) at RT. The reaction was stirred at ambient temperature for 15 h. after which time the reaction was complete by TLC (petroleum ether:ethyl acetate, 4:1, visualised with Erlichs). The reaction mixture was diluted with diethyl ether, washed three times with aqueous sodium bicarbonate, once with brine, dried over magnesium sulphate, filtered and evaporated. The resulting semi-solid was recrystallised from minimal hot petroleum ether to give N-(5-(hydroxymethyl)-2,2-dimethyl-1,3-dioxan-5-yl)pivalamide (7.32 g, 65%) as white crystals. $^1$H NMR (CDCl$_3$) δ 5.31 (br s, 1H, NH), 4.18 (br s, 1H, OH), 3.85 (d, J=11.5 Hz, 2H), 3.80 (d, J=11.5 Hz, 2H), 3.70 (d, 6.6 Hz, 2H), 1.46 (s, 12H), 1.44 (s, 3H). $^{13}$C NMR (CDCl$_3$) δ 154.0, 98.8, 80.5, 64.8, 64.5 (2C), 53.4, 28.3 (3C), 26.9, 20.3.

Example 1.2

Synthesis of tert-butyl 2,2-dimethyl-5-(methylthiomethyl)-1,3-dioxan-5-ylcarbamate To a solution of N-(5-(hydroxymethyl)-2,2-dimethyl-1,3-dioxan-5-yl)pivalamide (1.03 g, 4.20 mmol) and triethylamine (1.52 mL, 10.9 mmol) in $CH_2Cl_2$ (10 mL) was added methanesulfonyl chloride (0.425 mL, 5.46 mmol) dropwise at 0° C. The reaction was allowed to warm to room temperature and was complete after 1.5 h as indicated by TLC (petroleum ether:ethyl acetate, 4:1, visualised with Erlichs). The reaction mixture was diluted with $CH_2Cl_2$, washed with water and brine, dried over magnesium sulfate, filtered and evaporated to yield (2,2-dimethyl-5-pivalamino-1,3-dioxan-5-yl)-methyl methanesulfonate (1.35 g, 4.17 mmol, 99%) as a pale yellow solid. To a solution of (2,2-dimethyl-5-pivalamino-1,3-dioxan-5-yl)-methyl methanesulfonate (0.566 g, 1.67 mmol), in DMF (3 mL) was added sodium thiomethoxide (0.292 g, 4.17 mmol) at room temperature under argon for 15 h. TLC (petroleum ether:ethyl acetate, 4:1, visualised with Erlichs) indicated the reaction was complete so the contents of the flask were diluted with ethyl acetate, washed three times with aqueous sodium bicarbonate and once with brine. The organic layer was dried over magnesium sulfate, filtered and concentrated. The resulting pale yellow solid was purified by flash column chromatography (petroleum ether:ethyl acetate, 5:1) to give tert-butyl 2,2-dimethyl-5-(methylthiomethyl)-1,3-dioxan-5-ylcarbamate (0.460 g, 95%) as a white solid. $^1H$ NMR ($CDCl_3$) δ 4.86 (br s, 1H, NH), 4.01 (d, J=11.7 Hz, 2H), 3.82 (d, J=11.7 Hz, 2H), 3.02 (s, 2H), 2.16 (s, 3H), 1.50 (s, 3H), 1.45 (s, 9H), 1.41 (s, 3H). $^{13}C$ NMR ($CDCl_3$) δ 154.8, 98.5, 95.3, 65.4 (2C), 52.4, 37.3, 28.4 (3C), 24.6, 22.6, 17.5.

Example 1.3

Synthesis of 2-amino-2-(methylthiomethyl)propane-1,3-diol, hydrochloride salt

A solution of tert-butyl 2,2-dimethyl-5-(methylthiomethyl)-1,3-dioxan-5-ylcarbamate (2.64 g, 9.06 mmol) in methanol (10 mL) was added to a solution of concentrated hydrochloric acid (8 mL) in methanol (100 mL) and evaporated to give a yellow oil, which was purified by flash column chromatography ($CH_2Cl_2$:methanol:7 M methanolic ammonia, 5:2:1). The residue was reconverted to the hydrochloride salt by treatment with a solution of concentrated hydrochloric acid (1 mL) in methanol (5 mL) to give the 2-amino-2-(methylthiomethyl)propane-1,3-diol, hydrochloride salt (1.37 g, 100%). $^1H$ NMR ($D_2O$) δ 3.74 (s, 4H), 2.88 (s, 2H), 2.19 (s, 3H). $^{13}C$ NMR (DMSO) δ 64.4 (2C), 57.9, 48.9, 17.5. +ESMS Found 152.0744 (M–Cl$^-$) $C_5H_{14}NO_2S$ requires 152.0745.

Example 1.4

2-((5-(benzyloxymethyl)-4-chloro-5H-pyrrolo[3,2-d]pyrimidin-7-yl)methylamino)-2-(methylthiomethyl)propane-1,3-diol To a solution of 2-amino-2-(methylthiomethyl)propane-1,3-diol, hydrochloride salt (60.0 mg, 0.397 mmol) and 5-(benzyloxymethyl)-4-chloro-5H-pyrrolo[3,2-d]pyrimidine-7-carbaldehyde (126 mg, 0.397 mmol) in methanol (4 mL) was added sodium cyanoborohydride (27.4 mg, 0.436 mmol). After 15 h at ambient temperature the contents of the flask were concentrated under reduced pressure. Purification by flash column chromatography ($CH_2Cl_2$:7 M methanolic ammonia, 10:1) gave 2-((5-(benzyloxymethyl)-4-chloro-5H-pyrrolo[3,2-d]pyrimidin-7-yl)methylamino)-2-(methylthiomethyl)propane-1,3-diol (110 mg, 0.252 mmol, 64%) as a yellow gum. $^1H$ NMR ($CD_3OD$) δ 8.57 (s, 1H), 7.84 (s, 1H), 7.18-7.13 (m, 5H), 5.82 (s, 2H), 4.52 (s, 2H), 3.95 (s, 2H), 3.68 (d, J=11.5 Hz, 2H), 3.61 (d, J=11.5 Hz, 2H), 2.76 (s, 2H), 2.11 (s, 3H). +ESMS Found 437.1407 (M+H$^+$) $C_{20}H_{26}N_4O_3SCl$ requires 437.1414.

Example 1.5

2-((5-(benzyloxymethyl)-4-chloro-5H-pyrrolo[3,2-d]pyrimidin-7-yl)methylamino)-2-(methylthiomethyl)propane-1,3-diol A solution of 2-((5-(benzyloxymethyl)-4-chloro-5H-pyrrolo[3,2-d]pyrimidin-7-yl)methylamino)-2-(methylthiomethyl)propane-1,3-diol (20.0 mg, 0.0458 mmol) in 7 M methanolic ammonia (~3 mL) was stirred in a sealed pressure tube in an oil bath heated to 135° C. for 20 h. The contents of the pressure tube were cooled to ambient temperature then concentrated under reduced pressure to give 2-((5-(benzyloxymethyl)-4-chloro-5H-pyrrolo[3,2-d]pyrimidin-7-yl)methylamino)-2-(methylthiomethyl)propane-1,3-diol (19.0 mg, 0.0455 mmol, 99%) as a yellow gum. The product was of sufficient purity to be used directly in the final deprotection step. $^1H$ NMR ($CD_3OD$): δ 8.24 (s, 1H), 7.76 (s, 1H), 7.40-7.36 (m, 5H), 5.78 (s, 2H), 4.62 (s, 2H), 4.33 (s, 2H), 3.95 (d, J=11.9 Hz, 2H), 3.90 (d, J=11.9 Hz, 2H), 2.98 (s, 2H), 2.24 (s, 3H).

Example 1.6

2-((4-amino-5H-pyrrolo[3,2-d]pyrimidin-7-yl)methylamino)-2-(methylthiomethyl)propane-1,3-diol To a suspension of 2-((5-(benzyloxymethyl)-4-chloro-5H-pyrrolo[3,2-d]pyrimidin-7-yl)methylamino)-2-(methylthiomethyl)propane-1,3-diol (9.0 mg, 0.037 mmol) and palladium-black (10 mg) in 7 M methanolic ammonia (2 mL) was added hydrazine hydrochloride (0.250 mL, 6.87 mmol) dropwise. After 1 h at ambient temperature the reaction was virtually complete by TLC (dichloromethane:7 M methanolic ammonia, 3:1, visualised with UV and Erlichs). The supernatant solution was filtered through a small pad of celite and the palladium was washed twice with methanol and also filtered through celite. The combined filtrates were concentrated under reduced pressure and the resulting residue triturated with chloroform and dichloromethane. Lyophilization of the residue gave 2-((4-amino-5H-pyrrolo[3,2-d]pyrimidin-7-yl)methylamino)-2-(methylthiomethyl)propane-1,3-diol (4 mg, 63%) as a white solid. $^1H$ NMR ($D_2O$) δ 8.16 (s, 1H), 7.58 (s, 1H), 4.12 (s, 2H), 3.79-3.70 (m, 4H), 2.85 (s, 2H), 2.15 (s, 3H). +ESMS Found 298.1346 (M+H$^+$) $C_{12}H_{20}N_5O_2S$ requires 298.1338.

Example 2

Synthesis of (S)-1-((4-amino-5H-pyrrolo[3,2-d]pyrimidin-7-yl)methylamino)-3-(methylthio)propan-2-ol

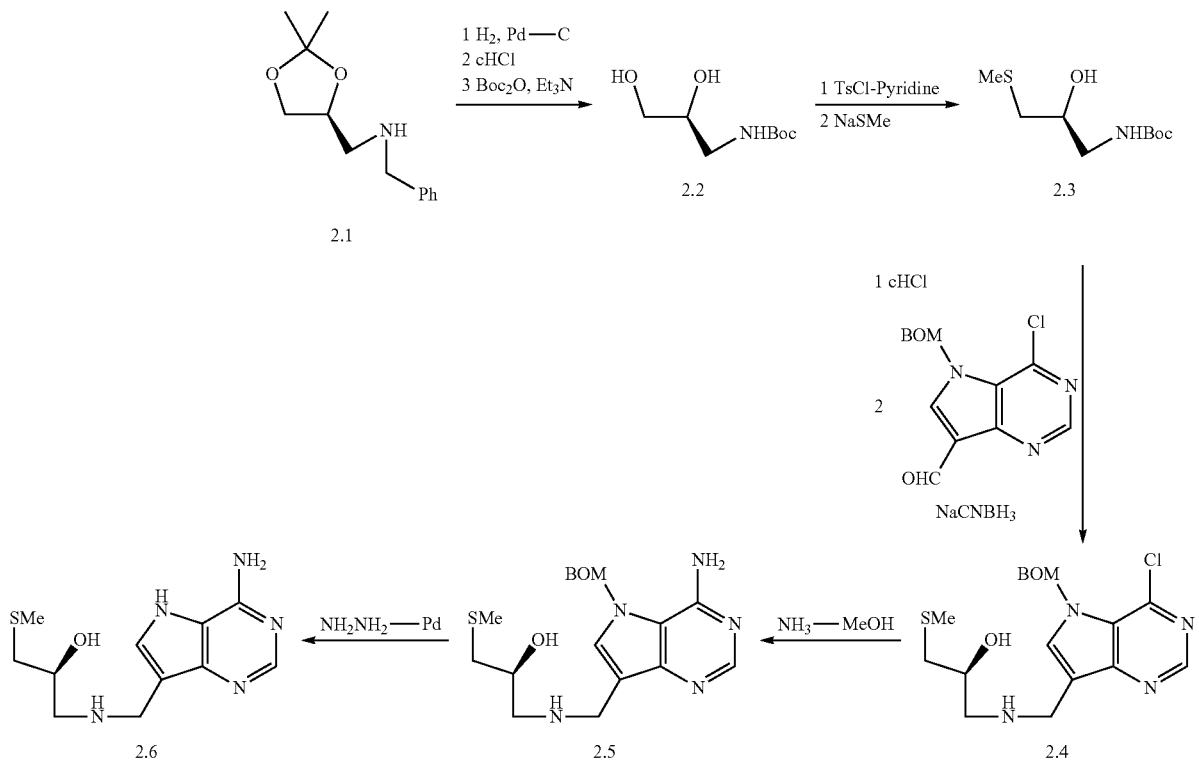

Example 2.1

(S)—N-benzyl-1-(2,2-dimethyl-1,3-dioxolan-4-yl)methanamine (R)-(2,2-Dimethyl-1,3-dioxolan-4-yl)methyl methanesulfonate was prepared from (S)-(2,2-dimethyl-1,3-dioxolan-4-yl)methanol (Sigma-Aldrich, 99% ee) by a known literature procedure (H. S. Kim, D. Barak, T. K. Harden, J. L. Boyer and K. A. Jacobson, *J. Med. Chem.*, 2001, 44, 3092). The title compound was prepared in the same way as described by M. Lemaire, F. Posada, J.-G. Gourcy and G. Jeminet, *Synlett*, 1995, 627. A solution of (R)-(2,2-dimethyl-1,3-dioxolan-4-yl)methyl methanesulfonate (3.9 g, 18.55 mmol) and benzylamine (8.10 ml, 74.2 mmol) was refluxed in CH₃CN (50 ml) for 48 h. The solvent was evaporated and the residue dissolved in EtOAc and washed with aqueous sat. NaHCO₃, dried and the solvent evaporated. The residue was chromatographed (EtOAc-hex, 6:4 then 8:2) to give (S)—N-benzyl-1-(2,2-dimethyl-1,3-dioxolan-4-yl)methanamine (3.1 g, 14.01 mmol, 76% yield) as a yellow oil.

Example 2.2

Synthesis of (S)-tert-butyl 2,3-dihydroxypropylcarbamate

The product from Example 2.1 (1.5 g, 6.78 mmol) was dissolved in EtOH (30 ml), 10% Pd—C (200 mg) added and the mixture stirred under hydrogen from a balloon at rt for 16 h. The catalyst was filtered off over Celite and the solvent evaporated to give (S)-(2,2-dimethyl-1,3-dioxolan-4-yl)methanamine as a colourless oil (840 mg). The ¹H NMR was in agreement with that described in G. Wang and R. I. Hollingsworth, *J. Org. Chem.*, 1999, 64, 1036. The oil was dissolved in a mixture of water (2 ml) and 37% aq. HCl (2 ml) and heated to 100° C. for 30 mins. The solvent was evaporated to give (S)-3-aminopropane-1,2-diol hydrochloride as an oil (720 mg, 5.65 mmol). The ¹H and ¹³C NMR data were in agreement with those quoted in G. Wang and R. I. Hollingsworth, *J. Org. Chem.*, 1999, 64, 1036. +ESMS (free base) found 92.0705 (M+H)⁺ C₃H₁₀NO₂ requires 92.0712. The HCl salt (0.71 g, 5.57 mmol) was dissolved in MeOH (20 ml) and triethylamine (1.5 ml, 11.1 mmol) added followed by di-tert-butyl dicarbonate (1.33 g, 6.1 mmol). The mixture was stirred at rt for 2 h then the solvent evaporated. The residue was chromatographed on silica gel (CH₂Cl₂-MeOH, 92:8) to give the title compound as a colourless gum contaminated with some Et₃NHCl. The products were dissolved in MeOH and stirred with Amberlyst A26 (OH⁻) resin, filtered and the solvent evaporated to give pure (S)-tert-butyl 2,3-dihydroxypropylcarbamate (0.849 g, 66%). The ¹H NMR was in agreement with data in T Kai, X.-L. Sun, K. M. Faucher, R. P. Apkarian and E. L. Chaikof, *J. Org. Chem.*, 2005, 70, 2606 and G Kokotos, R. Verger and A. Chiou, *Chem. Europ. J.*, 2000, 6, 4211. The $^{13}$C NMR was in agreement with that described in G Kokotos, R. Verger and A. Chiou, *Chem. Europ. J.,* 2000, 6, 4211.

+ESMS Found 214.1053 (M+Na)$^+$ C$_8$H$_{17}$NNaO$_4$ requires 214.1055. [α]$^{D\ 21}$ +7.8 (c 0.895, CHCl$_3$). Lit G Kokotos, R. Verger and A. Chiou, *Chem. Europ. J.,* 2000, 6, 4211 [α]$^{D\ 21}$ +6.7 (c 0.5, CHCl$_3$).

Example 2.3

Synthesis of (S)-tert-butyl 2-hydroxy-3-(methylthio)propylcarbamate p-Toluenesulfonyl chloride (0.812 g, 4.26 mmol) was added to a solution of the product from Example 2.2 (0.74 g, 3.87 mmol) in dry pyridine (15 ml) at 0° C. After 15 mins the solution was warmed to it and stirred for 2 h. More p-toluenesulfonyl chloride (400 mg) was added and the mixture stirred for 16 h. A further quantity of p-toluenesulfonyl chloride (800 mg) was added and the mixture stirred a further 24 h. The solvent was evaporated and the residue chromatographed on silica gel (EtOAc-hexanes, 1:1, then EtOAc) to give first intermediate tosylate (490 mg) then recovered (S)-tent-butyl 2,3-dihydroxypropylcarbamate (223 mg). The latter was dissolved in dry pyridine (10 ml) and p-toluenesulfonyl chloride (446 mg) added and the mixture stirred for 16 h at rt. Work-up and chromatography as above gave another 179 mg of tosylate. The combined tosylate products (625 mg 1.8 mmol) were dissolved in DMF (5 ml) and sodium thiomethoxide (257 mg, 3.6 mmol) added with initial ice cooling. The mixture was stirred at it for 2 h then the solvent evaporated and the residue chromatographed on silica gel (EtOAc-hexanes, 2:8) to give (S)-tert-butyl 2-hydroxy-3-(methylthio)propylcarbamate (0.189 g, 22%) as a colourless oil. [α]$^{D\ 21}$ −9.2 (c 0.65, MeOH). $^1$H NMR (CDCl$_3$) δ ppm 5.02 (brs, 1H, exchanged to D$_2$O), 3.80 (m, 1H), 3.42 (m, 1H), 3.22 (s, 1H, exchanged to D$_2$O), 3.14 (m, 1H), 2.65 (dd, J=13.8, 4.6 Hz, 1H), 2.51 (dd, J=13.8, 8.3 Hz, 1H), 2.12 (s, 3H), 1.45 (s, 9H). $^{13}$C NMR (CDCl$_3$, referenced to the centre line of CDCl$_3$ at 77.0 ppm) δ 156.7, 79.7, 68.7, 45.2, 38.9, 28.4, 15.6. +ESMS Found 244.0980 (M+Na)$^+$ C$_9$F$_{19}$NNaO$_3$S requires 244.0983.

Example 2.4

Synthesis of (S)-1-((5-(benzyloxymethyl)-4-chloro-5H-pyrrolo[3,2-d]pyrimidin-7-yl)methylamino)-3-(methylthio)propan-2-ol The product from Example 2.3 (0.18 g, 0.813 mmol) was dissolved in a mixture MeOH (3 ml) and 37% aq. HCl (2 ml). After 5 mins the solvent was evaporated. The residue of (S)-1-amino-3-(methylthio)propan-2-ol hydrochloride was dissolved in MeOH (8 ml) and 5-(benzyloxymethyl)-4-chloro-5H-pyrrolo[3,2-d]pyrimidine-7-carbaldehyde (0.270 g, 0.895 mmol) and sodium cyanoborohydride (0.066 g, 1.057 mmol) were added and the mixture stirred at rt for 60 h. The solvent was evaporated and the residue chromatographed on silica gel (CH$_2$Cl$_2$-7M NH$_3$-MeOH 98:2) to give (S)-1-((5-(benzyloxymethyl)-4-chloro-5H-pyrrolo[3,2-d]pyrimidin-7-yl)methylamino)-3-(methylthio)propan-2-ol (0.146 g, 44%) as a colourless gum. $^1$H NMR (CD$_3$OD) δ 8.62 (s, 1H), 7.89 (s, 1H), 7.21 (m, 5H), 5.90 (s, 2H), 4.56 (s, 2H), 4.03 (d, J=13.8 Hz, 1H), 3.96 (d, J=13.8 Hz, 1H), 3.87 (m, 1H), 2.85 (dd, J=12.1, 3.5 Hz, 1H), 2.63 (dd, J=12.1, 8.3 Hz, 1H), 2.55 (d, J=6.4 Hz, 2H), 2.09 (s, 3H). $^{13}$C NMR (CD$_3$OD, referenced to the centre line of CD$_3$OD at 49.0 ppm) δ 153.0, 150.6, 143.9, 138.7, 138.5, 129.3, 128.8, 128.7, 125.5; 115.6, 78.3, 71.7, 70.3, 54.6, 43.1, 40.4, 16.2. +ESMS Found 407.1310 (M+H)$^+$ C$_{19}$H$_{24}$$^{35}$ClN$_4$O$_2$S requires 407.1309.

Example 2.5

Synthesis of (S)-1-((4-amino-5-(benzyloxymethyl)-5H-pyrrolo[3,2-d]pyrimidin-7-yl)methylamino)-3-(methylthio)propan-2-ol The product from Example 2.4 (0.124 g, 0.305 mmol) was stirred in a solution of 7M NH$_3$-MeOH (25 ml) for 24 h in a sealed tube at 135° C. (oil bath). After cooling to rt the solvent was evaporated and the residue chromatographed on silica gel (CH$_2$Cl$_2$-7M NH$_3$ in MeOH, 98:2) to give (S)-1-((4-amino-5-(benzyloxymethyl)-5H-pyrrolo[3,2-d]pyrimidin-7-yl)methylamino)-3-(methylthio)propan-2-ol (0.085 g, 72%) as a colourless gum. $^1$H NMR (CD$_3$OD) δ 8.16 (s, 1H), 7.47 (s, 1H), 7.28 (m, 5H), 5.66 (s, 2H), 4.58 (s, 2H), 3.97 (d, J=13.8 Hz, 1H), 3.91-3.83 (m, 2H), 2.84 (dd, J=12.1, 3.5 Hz, 1H), 2.62 (dd, J=12.1, 8.4 Hz, 1H), 2.56 (d, J=6.4 Hz, 2H), 2.09 (s, 3H). $^{13}$C NMR (CD$_3$OD) δ 152.8, 151.6, 149.4, 137.7, 133.5, 129.5, 129.3, 129.2, 116.0, 114.3, 78.6, 71.4, 70.3, 54.6, 43.3, 40.4, 16.2. +ESMS Found 388.1813 (M+H)$^+$ C$_{19}$H$_{26}$N$_5$O$_2$S requires 388.1807.

Example 2.6

Synthesis of (S)-1-((4-amino-5H-pyrrolo[3,2-d]pyrimidin-7-yl)methylamino)-3-(methylthio)propan-2-ol The product from Example 2.5 (0.08 g, 0.206 mmol) was dissolved in 7M NH3-MeOH solution (8 ml) and Pd black (80 mg) added followed by hydrazine hydrate (1.2 ml). The mixture was stirred for 40 mins, filtered and the solvent evaporated. The residue was chromatographed on silica gel (CH$_2$Cl$_2$-7M NH3 in MeOH, 85:15) to give(S)-1-((4-amino-5H-pyrrolo[3,2-d]pyrimidin-7-yl)methylamino)-3-(methylthio)propan-2-ol (0.042 g, 76%) as a colourless solid. [α]$_D$$^{20}$ −12.4 (c, 0.355, MeOH). $^1$H NMR (CD$_3$OD), δ 8.16 (s, 1H), 7.48 (s, 1H), 4.00 (d, J=13.5 Hz, 1H), 3.92-3.84 (m, 2H), 2.85 (dd, J=12.2, 3.5 Hz, 1H), 2.65 (dd, J=12.2, 8.5 Hz, 1H), 2.55 (d, J=6.5 Hz, 2H), 2.10 (s, 3H). $^{13}$C NMR (CD$_3$OD, referenced to the centre line of CD$_3$OD at 49.0 ppm), δ 152.1, 150.9, 146.6, 129.1, 115.4, 114.2, 70.2, 54.6, 43.5, 40.4, 16.2. +ESMS Found 268.1241 (M+H)$^+$ C$_{11}$H$_{18}$N$_5$OS requires 268.1232.

Example 3

Synthesis of (2RS,3SR)-4-[(4-amino-5H-pyrrolo[3,2-d]pyrimidin-7-yl)methylamino]-3-(methylthiomethyl)butane-1,2-diol

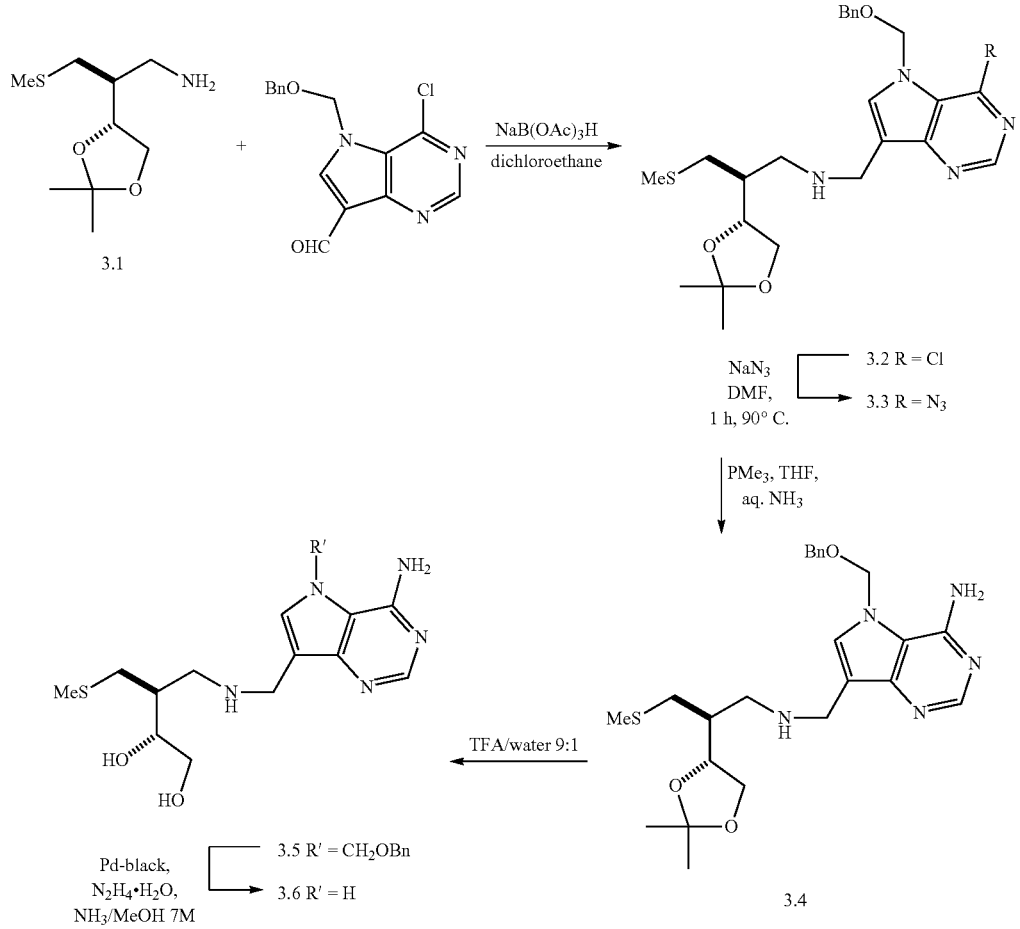

Example 3.1

Synthesis of (SR)—N-benzyl-2-(RS)-2,2-dimethyl-1,3-dioxolan-4-yl)-3-(methylthio)propan-1-amine A mixture of N-benzylhydroxylamine hydrochloride (13.59 g, 85.15 mmol) and sodium acetate (9.31 g, 114 mmol) were stirred together in ethanol (75 mL) at rt for 15 mins. Aqueous 37% formaldehyde solution (12.68 ml, 170 mmol) was added and stirring continued for 30 mins, then cis-2-butene-1,4-diol (4.67 ml, 56.8 mmol) added and the mixture heated under reflux for 16 h. The solvent was evaporated and the residue dissolved in CHCl$_3$ and washed with aq. sat. NaHCO$_3$, dried (MgSO$_4$) and the solvent evaporated to give a brown syrup suitable for use without further purification (12.5 g, 98%). An aliquot was purified by chromatography on silica gel (EtOAc then EtOAc-MeOH, 95:5) to give ((4RS,5RS)-2-benzylisoxazolidine-4,5-diyl)dimethanol as a colourless syrup. $^{13}$C NMR (CDCl$_3$, referenced to the centre line of CDCl$_3$ at 77.0 ppm) δ 136.5, 129.0, 128.4, 127.6, 78.5, 62.4, 61.3, 60.4, 56.8, 45.8.

To a solution of (±)-((4RS,5RS)-2-benzylisoxazolidine-4,5-diyl)dimethanol (0.74 g, 3.28 mmol) in acetone (15 mL) and 2,2-dimethoxypropane (5 mL) was added 1R-(−)-camphorsulfonic acid (0.916 g, 3.94 mmol) and the mixture stirred at rt for 1 h. Triethylamine (0.916 ml, 6.57 mmol) was added and the solvent was evaporated. The residue was dissolved in CHCl$_3$ and washed with 10% aq Na$_2$CO$_3$, dried (MgSO$_4$) and the solvent evaporated. The residue was chromatographed on silica gel (CHCl$_3$-EtOAc-MeOH, 5:2:1) to give (RS)-3-(benzylamino)-2-((RS)-2,2-dimethyl-1,3-dioxalan-4-yl)propan-1-ol as a syrup (0.55 g, 63%). $^1$H NMR (CDCl$_3$) δ 7.36-7.23 (m, 5H), 4.04-3.97 (m, 2H), 3.89 (dd, J=10.9, 4.3 Hz, 1H), 3.82-3.62 (m, 4H), 3.10 (br.s, 2H),2.79 (dd, J=11.8, 4.0 Hz, 1H), 2.71 (dd, J=11.8, 8.8 Hz, 1H), 1.94 (m, 1H), 1.39 (s, 3H), 1.33 (s, 3H). $^{13}$C NMR (CDCl$_3$, referenced to the centre line of CDCl$_3$ at 77.0 ppm) δ 139.1, 128.5, 128.1, 127.3, 108.8, 76.2, 67.8, 64.8, 54.0, 50.5, 43.3, 26.5, 25.3.

This product (0.5 g, 1.884 mmol) and di-tent-butyl dicarbonate (0.452 g, 2.073 mmol) were stirred together in MeOH (10 ml) for 1 h. The solvent was evaporated and the residue of (±)-tert-butyl benzyl((RS)-2-((RS)-2,2-dimethyl-1,3-dioxolan-4-yl)-3-hydroxypropyl)carbamate was dissolved in CH$_2$Cl$_2$ (10 ml) and triethylamine (0.394 ml, 2.83 mmol)

added. The mixture was cooled in an ice bath and methanesulfonyl chloride (0.176 ml, 2.261 mmol) was added dropwise. The mixture was warmed to rt and stirred for 30 min. then washed with aq. sat. NaHCO$_3$, dried (MgSO$_4$) and the solvent evaporated to give crude (±)-(R/S)-3-(benzyl(tert-butoxycarbonyl)amino)-2-((R/S)-2,2-dimethyl-1,3-dioxolan-4-yl)propyl methanesulfonate. The latter was dissolved in DMF (3 ml) and sodium thiomethoxide (0.264 g, 3.77 mmol) added. After stirring at it for 3 h the mixture was diluted with diethyl ether (50 ml) and washed with water (4×5 ml), dried (MgSO$_4$) then the solvent evaporated. The residue was chromatographed on silica gel (EtOAc-hexanes, 15:85) to give tent-butyl benzyl((SR)-2-((RS)-2,2-dimethyl-1,3-dioxolan-4-yl)-3-(methylthio)propyl)carbamate as a colourless gum (421 mg) which was dissolved in a mixture of CH$_2$Cl$_2$ (10 ml) and TFA (1 ml) and stirred for 70 mins. The mixture was diluted with CH$_2$Cl$_2$ and washed with aq. sat. NaHCO$_3$, dried (MgSO$_4$) and the solvent evaporated. The residue was chromatographed on silica gel (toluene-acetone, 13:1) to give (SR)—N-benzyl-2-((RS)-2,2-dimethyl-1,3-dioxolan-4-yl)-3-(methylthio)propan-1-amine (0.13 g, 23%) as a pale yellow oil. $^1$H NMR (CDCl$_3$) δ 7.39-7.20 (m, 5H), 4.17 (q, J=6.8 Hz, 1H), 4.03 (dd, J=8.1, 6.2 Hz, 1H), 3.77 (s, 2H), 3.68 (t, J=7.8 Hz, 1H), 2.78 (dd, J=13.1, 4.3 Hz, 1H), 2.73-2.64 (m, 2H), 2.60 (dd, J=13.1 7.9 Hz, 1H), 2.11 (s, 3H), 1.92 (m, 1H), 1.70 (br.s, 1H, exchanged to D$_2$O), 1.38 (s, 3H), 1.34 (s, 3H). $^{13}$C NMR (CDCl$_3$, referenced to the centre line of CDCl$_3$ at 77.0 ppm) δ 140.3, 128.4, 128.1, 126.9, 108.5, 76.9, 67.8, 54.2, 49.3, 42.1, 34.3, 26.6, 25.4, 16.5. +ESMS Found 296.1683 C$_{16}$H$_{26}$NO$_2$S (M+H)$^+$ requires 296.1684.

Example 3.2

Synthesis of (SR)—N-[(5-(benzyloxymethyl)-4-chloro-5H-pyrrolo[3,2-d]pyrimidin-7-yl)methyl]-2-((RS)-2,2-dimethyl-1,3-dioxolan-4-yl)-3-(methylthio)propan-1-amine To a solution of the product of Example 3.1 (70 mg, 0.34 mmol) and 5-(benzyloxymethyl)-4-chloro-5H-pyrrolo[3,2-d]pyrimidine-7-carbaldehyde (80%, 129 mg, 0.34 mmol) in 1,2-dichloroethane (5 mL) was added Na(OAc)$_3$BH (95%, 152 mg, 0.68 mmol) at room temperature. After 40 min saturated aqueous NaHCO$_3$ (10 mL) was added, vigorously stirred and the organic layer was separted, dried (MgSO$_4$) and evaported in vacuo. The residue was purified by chromatography (12 g silica, CHCl$_3$/EtOAc/MeOH=5:2:1 v/v/v) which gave compound 3.1 as a colourless oil (107 mg, 64%). R$_f$=0.35 (CHCl$_3$/EtOAc/MeOH=5:2:1 v/v/v). NMR (CDCl$_3$) δ 8.72 (s, 1H), 7.53 (s, 1H), 7.35-7.21 (m, 5H), 5.82 (s, 2H), 4.53 (s, 2H), 4.18 (dd, J=6.7, 13.4 Hz, 1H), 4.04 (dd, J=6.3, 8.1 Hz, 1H), 4.00 (br s, 2H), 3.69 (dd, J=7.6, 7.9 Hz, 1H), 2.83-2.67 (m, 3H), 2.61 (dd, J=7.8, 13.1 Hz, 1H), 2.19-1.88 (m, 5H), 1.38 (s, 3H), 1.33 (s, 3H). $^{13}$C NMR (CDCl$_3$, referenced to the middle chloroform peak at 77.4 ppm) δ 152.2, 150.3, 142.8, 136.7, 135.3, 128.9, 128.5, 128.0, 124.7, 116.6, 108.9, 77.1, 76.8, 70.8, 68.0, 49.7, 43.7, 42.3, 34.5, 26.9, 25.7, 16.8. HRMS: (M+H)$^+$ calcd. for C$_{22}$H$_{33}$N$_4$O$_3$NaS$^{33}$Cl: 491.1860. found: 491.1864.

Example 3.3

Synthesis of (SR)—N-((4-azido-5-(benzyloxymethyl)-5H-pyrrolo[3,2-d]pyrimidin-7-yl)methyl)-2-((RS)-2,2-dimethyl-1,3-dioxolan-4-yl)-3-(methylthio)propan-1-amine Under Argon the product of Example 3.2 (100 mg, 0.20 mmol) was dissolved in dry DMF (3 ml), NaN$_3$ (50 mg, 0.77 mmol) was added and the mixture was heated to 90° C. After 1 h the reaction mixture was cooled to room temperature and concentrated in vacuo. The residue was suspended in CHCl$_3$/MeOH and absorbed on silica in vacuo and purified by chromatography (~12 g silica, EtOAc, then CHCl$_3$/MeOH=15:1 v/v) which gave compound 3.2 as a colourless oil (101 mg, 100%). R$_f$=0.24 (CHCl$_3$:MeOH=15:1). $^1$H NMR (CDCl$_3$) δ 9.38 (s, 1H), 7.55 (s, 1H), 7.30-7.15 (m, 5H), 6.05 (s, 2H), 4.64 (s, 2H), 4.20 (dd, J=6.7, 13.5 Hz, 1H), 4.14-4.00 (m, 3H), 3.71 (dd, J=7.6, 7.8 Hz, 1H), 2.98-2.69 (m, 3H), 2.62 (dd, J=7.8, 13.1 Hz, 1H), 2.24 (br s, 1H), 2.10 (s, 3H), 2.07-1.91 (m, 1H), 1.38 (s, 3H), 1.33 (s, 3H). $^{13}$C NMR (CDCl$_3$, referenced to middle chloroform peak at 77.4 ppm) δ 142.1, 138.8, 136.8, 131.5, 129.5, 128.7, 128.3, 128.0, 120.1, 113.7, 108.9, 78.3, 77.1, 71.8, 68.0, 49.8, 43.9, 42.3, 34.5, 26.9, 25.7, 16.8. HRMS: (M+H)$^+$ calcd. for C$_{24}$H$_{32}$N$_7$O$_3$S: 498.2287. found: 498.2276.

Example 3.4

Synthesis of 5-(benzyloxymethyl)-7-{[(SR)-2-((RS)-2,2-dimethyl-1,3-dioxolan-4-yl)-3-(methylthio)propylamino]methyl}-5H-pyrrolo[3,2-d]pyrimidin-4-amine The product of Example 3.3 (90 mg, 0.18 mmol) was dissolved in THF (2 mL) and PMe$_3$ (1.0M in THF, 500 µL, 0.50 mmol) was added at room temperature. After 1.5 h reaction was not complete and further PMe3 (1.0M in THF, 300 µL, 0.30 mmol) was added. After 2 h conc. aq. NH$_3$ (1.5 mL) was added and the mixture was stirred for further 15 min, evaporated in vacuo and left overnight. Next day, the residue was redissolved in CH$_2$Cl$_2$ (~5 mL) and absorbed on silica, evaporated in vacuo, purified by chromatography (30 g silica, CH$_2$Cl$_2$:NH$_3$ in MeOH 7M=15:1 v/v) which gave compound 3.3 as a colourless oil (78 mg, 91%). R$_f$=0.38 (CH$_2$Cl$_2$:NH$_3$ in MeOH 7M=12:1 v/v). $^1$H NMR (CDCl$_3$) δ 8.38 (s, 1H), 7.42-7.24 (m, 5H), 7.11 (s, 1H), 5.81 (s, 2H, D$_2$O exchangeable), 5.49 (s, 2H), 4.56 (s, 2H), 4.19 (dd, J=6.9, 13.4, 1H), 4.05 (dd, J=6.3, 8.1 Hz, 1H), 3.95 (br s, 2H), 3.70 (dd, J=7.5, 7.9 Hz, 1H), 2.85-2.68 (m, 3H), 2.62 (dd, J=7.6, 13.1 Hz, 1H), 2.21 (br s, 1H, D$_2$O exchangeable), 2.10 (s, 3H), 2.03-1.90 (m, 1H), 1.38 (s, 3H), 1.33 (s, 3H). $^{13}$C NMR (CDCl$_3$, referenced to the middle chloroform peak at 77.4 ppm) δ 151.7, 151.3, 149.9, 135.9, 130.5, 129.1, 129.0, 128.7, 115.7, 115.3, 108.9, 77.2, 77.1, 70.2, 68.1, 49.7, 44.0, 42.4, 34.6, 26.9, 25.7, 16.9. HRMS: (M+H)$^+$ calcd. for C$_{24}$H$_{34}$N$_5$O$_3$S: 472.2382. found: 472.2370.

Example 3.5

Synthesis of (2RS,3SR)-4-{[4-amino-5-(benzyloxymethyl)-5H-pyrrolo[3,2-d]pyrimidin-7-yl]methylamino}-3-(methylthiomethyl)-butane-1,2-diol The product of Example 3.4 (78 mg, 0.16 mmol) was treated with TFA/water (9:1 v/v, 2.0 mL). After 10 min the solution was evaporated in vacuo. Excess TFA was removed by evaporation with water (~5 mL) in vacuo. The residue was dissolved in MeOH (~1 mL) and toluene was added (~10 mL) and again evaporated in vacuo, and further dried under high vacuum which gave the trifluoroacetic acid salt of compound 3.4 as an oil (116 mg, 112%). The material was used without purification in the following step. R$_f$=0.26 (CH$_2$Cl$_2$:NH$_3$ in MeOH 7M=9:1), $^1$H NMR (CD$_3$OD) δ 8.46 (s, 1H), 8.01 (s, 1H), 7.32-7.25 (m, 5H), 5.84 (s, 2H), 4.44 (d, J=14.1 Hz, 1H), 4.39 (d, J=14.1 Hz, 1H), 3.87 (dd, J=4.4, 8.7

Hz, 1H), 3.70-3.58 (m, 2H), 3.44-3.34 (m, 2H), 2.68 (dd, J=5.3, 13.5 Hz, 1H), 2.48 (dd, J=9.1, 13.5 Hz, 1H), 2.42-2.26 (m, 1H), 2.08 (s, 3H). $^{13}$C NMR (CD$_3$OD, referenced to the middle methanol peak at 49.0 ppm) δ 153.2, 146.3, 141.1, 138.8, 137.2, 129.6, 129.5, 129.3, 114.6, 104.1, 79.4, 73.0, 72.5, 63.4, 49.4, 41.6, 40.1, 33.6, 15.5. HRMS: (M+H)$^+$ calcd. for C$_{21}$H$_{30}$N$_5$O$_3$S: 432.2069. found: 432.2059.

Example 3.6

Synthesis of (2RS,3SR)-4-[(4-amino-5H-pyrrolo[3,2-d]pyrimidin-7-yl)methylamino]-3-(methylthiomethyl)butane-1,2-diol The product of Example 3.5 (70 mg, 0.11 mmol) was dissolved in methanolic ammonia (7M, 5 mL) and Pd-black (95 mg, 0.89 mmol) was added, followed by hydrazine hydrate (500 μL, 10.3 mmol). After 15 min further Pd-black (101 mg, 0.95 mmol) was added. After 45 min the supernatant solution was filtered through flux calcined diatomaceous earth and the Pd catalyst was rinsed with MeOH (2×1 mL). The MeOH washes were also filtered and the combined filtrate was evaporated in vacuo. The residue was triturated with CHCl3 (~5 mL) and dried in high vacuum which gave the trifluoroacetic acid salt of compound 3.5 as a colourless oil (57 mg, 100%). R$_f$=0.26 (CH$_2$Cl$_2$:NH$_3$ in MeOH 7M=4:1 v/v). $^1$H NMR (CD$_3$OD) δ 8.21 (s, 1H), 7.68 (s, 1H), 4.35 (s, 2H), 3.84 (dd, J=4.7, 9.1, 1H), 3.66-3.57 (m, 2H), 3.36-3.22 (m, 2H), 2.68 (dd, J=5.2, 13.6 Hz, 1H), 2.46 (dd, J=9.1, 13.6 Hz, 1H), 2.33-2.20 (m, 1H), 2.06 (s, 3H). $^{13}$C NMR (CD$_3$OD, referenced to the middle methanol peak at 49.0 ppm) δ 163.2 (q, J=34 Hz), 152.4, 151.7, 146.5, 131.3, 118.2 (q, J=293 Hz), 115.5, 106.7, 73.3, 63.6, 42.8, 40.2, 33.6, 15.6.

Example 4

Synthesis of (2R,3S)-4-(((4-amino-5H-pyrrolo[2,3-d]pyrimidin-7-yl)methyl)(methyl)amino)-3-(methylthiomethyl)butane-1,2-diol

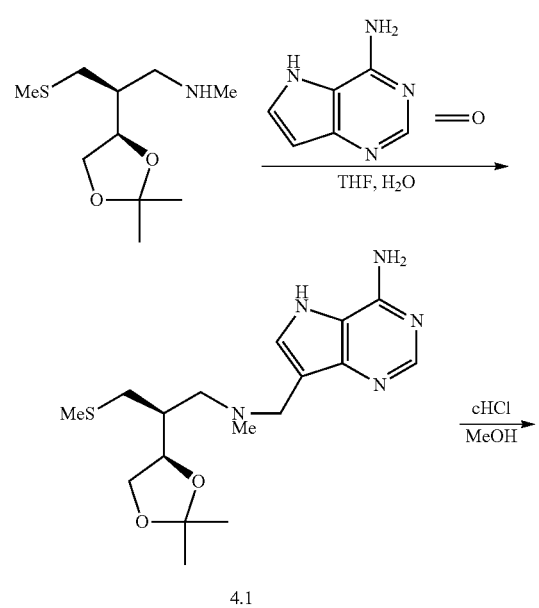

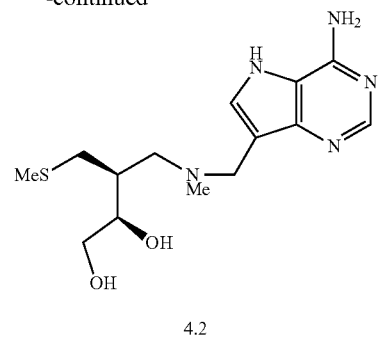

4.2

Example 4.1

Synthesis of 7-((((S)-2-((R)-2,2-dimethyl-1,3-dioxolan-4-yl)-3-(methylthio)propyl)(methyl)amino)methyl)-5H-pyrrolo[3,2-d]pyrimidin-4-amine 9-Deazaadenine (73 mg, 547 μmol) was added to a solution of (S)-2-((R)-2,2-dimethyl-1,3-dioxolan-4-yl)-N-methyl-3-(methylthio)propan-1-amine (80 mg, 365 μmol) and formaldehyde (0.044 ml, 37% aq, 547 μmol) in a 1,4-dioxane (2 ml) and water (0.5 ml) mixture and the resulting suspension heated to 90 C (bath temp). After 1 h the reaction was cooled to ambient and 7N NH3 in MeOH (2.5 ml) was added and the resulting reaction left to stir for a further 1 h. The reaction was then concentrated in vacuo and the residue purified by flash chromatography on silica gel eluting with 10% 7N NH3 in MeOH/DCM=>20% 7N NH3 in MeOH/DCM to afford the title compound (110 mg, 83%) as a syrup. $^1$H NMR (CD$_3$OD) δ 8.16 (s, 1H), 7.46 (s, 1H), 3.91 (m, 2H), 3.57 (m, 2H), 2.71 (dd, J=13.2, 4.1 Hz, 1H), 2.49 (m, 2H), 2.32 (m, 1H), 2.26 (s, 3H), 2.04 (s, 3H), 1.94 (m, 1H), 1.31 (s, 3H), 1.25 (s, 3H).

Example 4.2

Synthesis of (2R,3S)-4-(((4-amino-5H-pyrrolo[3,2-d]pyrimidin-7-yl)methyl)(methyl)amino)-3-(methylthiomethyl)butane-1,2-diol Concentrated hydrochloric acid (0.5 ml, 178 μmol) was added to a solution of 7-((((S)-2-((R)-2,2-dimethyl-1,3-dioxolan-4-yl)-3-(methylthio)propyl)(methyl)amino)methyl)-5H-pyrrolo[3,2-d]pyrimidin-4-amine (65 mg, 178 μmol) in methanol (5 ml) and the resulting reaction concentrated in vacuo. The resulting residue was purified by flash chromatography on silica gel eluting with 15% 7N NH3 in MeOH/DCM=>20% 7N NH3 in MeOH/DCM to afford (2R,3S)-4-(((4-amino-5H-pyrrolo[3,2-d]pyrimidin-7-yl)methyl)(methyl)amino)-3-(methylthiomethyl)butane-1,2-diol (35 mg, 61% yield) as a syrup. $^1$H NMR (CD$_3$OD) δ 8.16 (s, 1H), 7.49 (s, 1H), 3.84 (d, J=13.5. Hz, 1H), 3.68 (m, 2H), 3.54 (d, J=4.8 Hz, 2H), 2.70 (m, 2H), 2.53 (dd, J=12.8, 3.8 Hz, 1H), 2.39 (dd, J=13.1, 8.1 Hz, 1H), 2.28 (s, 3H), 2.14 (m, 1H), 2.08 (s, 3H). $^{13}$C NMR (CD$_3$OD). 152.5, 151.4, 147.6, 130.6, 115.6, 112.9, 75.4, 65.7, 59.7, 52.0, 42.7, 41.0, 36.0, 16.6.

Example 5

Synthesis of (2S,3S)-2-((4-amino-5H-pyrrolo[3,2-d]pyrimidin-7-yl)methylamino)-4-(methylthio)butane-1,3-diol

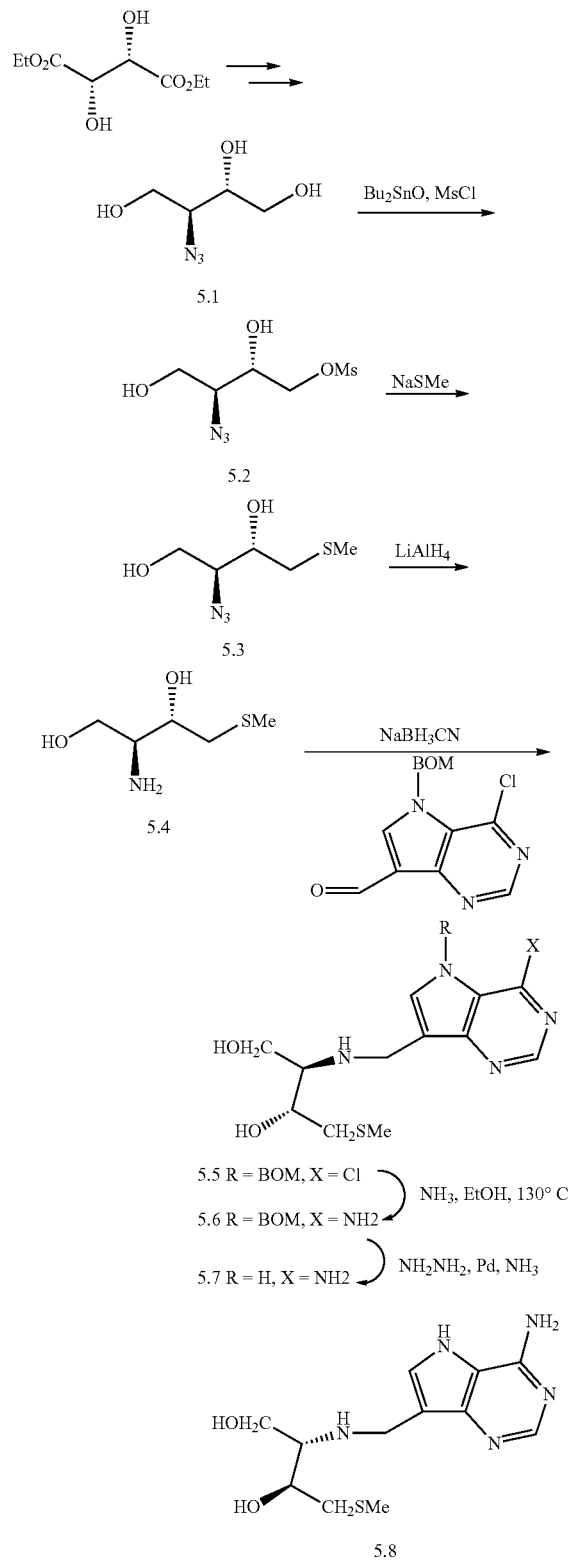

Example 5.2

Synthesis of (2R,3R)-3-Azido-2,4-dihydroxybutylmethanesulfonate

A suspension of (2R,3R)-3-azidobutanetriol (5.1) [1] (1.0 g, 6. mmol) and dibutyltin oxide (1.9 g, 1.2 eq) in toluene (60 mL) was heated to reflux under a Dean-Stark trap. After 30 min the resulting clear solution was cooled to room temperature and methanesulfonyl chloride (1.0 mL, 1.05 eq) was added. The solution was stirred overnight and then evaporated on to silica gel. The silica was placed on top of a column of silica and eluted with hexanes-ethyl acetate (1:1) to give the title compound as a pale yellow oil (1.1 g, 4.7 mmol, 72%). $^1$H NMR (CD$_3$OD) δ 4.36 (dd, 1H, J 3.2, 10.7), 4.30 (dd, 1H, J=5.6, 10.7), 3.94 (dd, 1H, J=3.6, 11.6), 3.84 (m, 1H), 3.34 (dd, 1H, J=7.0, 11.6), 3.56 (m, 1H), 3.13 (m, 3H). $^{13}$C NMR (CD$_3$OD) δ 73.1, 70.2, 66.3, 63.2, 37.7. HRMS C$_5$H$_{11}$N$_3$O$_5$$^{23}$NaS (M$^{23}$Na)$^+$ requires 248.0317. found 248.0320.

Example 5.3

Synthesis of (2R,3R)-2-azido-4-(methylthio)butane-1,3-diol

Sodium thiomethoxide (0.62 g, 8.8 mmol, 2 eq) was added to a solution of mesylate 5.2 (1.0 g, 4.4 mmol) in dry DMF (12 mL). After stirring for 2 h the mixture was diluted with water (100 mL) and extracted with EtOAc (5×50 mL). The combined extracts were dried, concentrated under reduced pressure and chromatographed on a column of silica gel eluted with hexanes-ethyl acetate (1:1) to give the title compound as a pale yellow syrup (0.40 g, 51%). $^1$H NMR (CDCl$_3$) δ 3.87 (dd, 1H, J=4.6, 11.6), 3.83 (dd, 1H, J=5.4, 11.6), 3.71 (m, 1H) 2.9 (brs, 1H), 2.80 (dd, 1H, J=3.3, 13.9), 2.55 (dd, 1H, J=9.1, 13.9), 2.07 (s, 3H). $^{13}$C NMR (CDCl$_3$) δ 69.5, 66.2, 63.2, 39.3, 15.9. HRMS C$_5$H$_{11}$N$_3$O$_2$$^{23}$NaS (M$^{23}$Na)$^+$ requires 200.0470. found 200.0472.

Example 5.4

Synthesis of (2R,3R)-2-amino-4-(methylthio)butane-1,3-diol

LAH (2M in THF, 1.8 mL, 1.6 eq) was added to a solution of azide 5.3 (0.4 g, 2.3 mmol) in dry THF (12 mL) cooled in an ice water bath. The solution was bought to room temperature and stirred in for 1 h and then water (0.5 mL) was added. The resulting slurry was concentrated to dryness on silica gel and chromatographed on a column of silica gel using 20% methanolic ammonia (7 M) in CH$_2$Cl$_2$ as eluant to give the title compound (0.22 g, 65%) as a yellow oil. $^1$H NMR (CD$_3$OD) δ 3.73 (dd, 1H, J 4.3, 10.8) 3.69 (m, 1H, 3.51 (dd, 1H, J=7.0, 10.8) 2.86 (m, 1H), 2.76 (dd, 1H, J=4.2, 13.7), 2.59 (dd, 1H, J=8.2, 13.7), 2.13 (s, 3H). $^{13}$C NMR (CD$_3$OD, 75 MHz) 73.5, 64.6, 57.7, 39.6, 16.4; HRMS C$_5$H$_{14}$NO$_2$S (MH)$^+$ requires 152.0745. found 152.0739.

Example 5.5

Synthesis of (2R,3R)-2-(5-benzyloxymethyl-4-chloro-5H-pyrrolo[3,2-d]pyrimidin-7-yl)methylamino)-4-(methylthio)butane-1,3-diol A stirred solution of amine 5.4 (85 mg, 0.56 mmol), 5-benzyloxymethyl-4-chloro-5H-pyrrolo[3,2-d]pyrimidine-7-carbaldehyde (170 mg, 0.56 mmol) and sodium cyanoborohydride (42.4 mg, 0.67 mmol) in methanol (5 mL) was brought to pH 7 by addition of HCl (2M in ether, 0.10 mL). After 3 h the solution was concentrated under reduced pressure and the residue was eluted through a column of silica gel with 3% methanolic ammonia (7 M) in $CH_2Cl_2$ to give the title compound (149 mg, 61%) as a yellow oil that solidified on standing. $^1$H NMR ($CD_3OD$) δ 8.62 (s, 1H), 7.91 (s, 1H), 7.22 (m, 5H), 5.90 (s, 2H), 4.56 (s, 2H), 4.04 (s, 2H), 3.90 (m, 1H), 3.76 (dd, 1H, J 4.6, 11.3), 3.66 (dd, 1H, J 5.9, 11.3), 2.75 (m, 2H) 2.61 (dd, 1H, J 7.8, 13.6), 2.08 (s, 3H). $^{13}$C NMR ($CD_3OD$) δ 153.4, 150.9, 144.3, 139.1, 138.9, 129.7, 129.2, 129.1, 126.0, 116.9, 78.7, 72.1, 72.0, 62.9, 61.7, 41.7, 39.6, 16.5. HRMS $C_{20}H_{26}N_4O_3S^{35}Cl$ $(MH)^+$ requires 437.1414. found 437.1412.

Example 5.6

Synthesis of (2R,3R)-2-((5-benzyloxymethyl-4-amino-5H-pyrrolo[3,2-d]pyrimidin-7-yl)methylamino)-4-(methylthio)butane-1,3-diol A solution of chloride 5.5 (120 mg, 0.12 mmol) in ethanolic ammonia (6 M) was heated at 130° C. for 48 h and then concentrated under reduced pressure. The residue was eluted through a column of silica gel with 7% methanolic ammonia (7 M) in $CH_2Cl_2$ to give the title compound (84 mg, 73%) as a yellow oil. $^1$H NMR ($CD_3OD$) δ 8.16 (s, 1H), 7.47 (s, 1H), 7.27 (m, 5H), 5.63 (s, 2H), 4.56 (s, 2H), 3.97 (s, 2H), 3.92 (m, 1H), 3.78 (dd, 1H, J=4.6, 11.3), 3.68 (dd, 1H, J=5.9, 11.3), 2.82 (m, 1H) 2.74 (dd, 1H, J=4.8, 13.5) 2.62 (dd, 1H J=7.9, 13.5), 2.08 (s, 3H). $^{13}$C NMR ($CD_3OD$) δ 153.2, 152.0, 149.8, 138.1, 134.0, 130.0, 129.7, 129.6, 116.5, 115.4, 79.0, 72.0, 71.8, 62.9, 61.7, 41.9, 39.6, 16.5. HRMS $C_{20}H_{28}N_5O_3S$ $(MH)^+$ requires 418.1908. found 437.1903.

Example 5.7

Synthesis of (2R,3R)-2-((4-amino-5H-pyrrolo[3,2-d]pyrimidin-7-yl)methylamino)-4-(methylthio)butane-1,3-diol Palladium black (34 mg, 0.33 mmol) and hydrazine hydrate (0.75 mL, 13 mmol) were added to a solution of compound 5.6 (34 mg, 0.081 mmol) in methanolic ammonia (7 M, 3 mL. After 0.5 h the mixture was filtered through a plug of Celite® and concentrated under reduced pressure. The residue was eluted through a column of silica gel with 20% methanolic ammonia (7 M) in $CH_2Cl_2$ to give the title compound (14 mg, 61%) as a pale yellow foam. $^1$H NMR ($CD_3OD$) δ 8.15 (s, 1H), 7.49 (s, 1H), 4.02 (s, 2H), 3.92 (m, 1H), 3.77 (dd, 1H, J=4.7, 11.4), 3.67 (dd, 1H, J=5.9, 11.4), 2.84 (m, 1H), 2.73 (dd, 1H, J=4.8, 13.6) 2.59 (dd 1H, J=8.0, 13.6) 2.09 (s, 3H). $^{13}$C NMR ($CD_3OD$) δ 152.5, 151.2, 147.0, 129.5, 115.8, 115.2, 71.8, 63.0, 61.6, 42.2, 39.5, 16.4. HRMS $C_{12}H_{20}N_5O_2S$ $(MH)^+$ requires 298.1138. found 298.1338.

Example 5.8

(2S,3S)-2-((4-amino-5H-pyrrolo[3,2-d]pyrimidin-7-yl)methylamino)-4-(methylthio)butane-1,3-diol The title compound was synthesised from (2S,3S)-3-azidobutanetriol in the same manner as its enantiomer 5.7. Both 5.8 and all intermediates had identical NMR spectra to their enantiomers. HRMS $C_{12}H_{20}N_5O_2S$ $(MH)^+$requires 298.1138. found 298.1339.

Example 6

Synthesis of (2R,3S)-2-((4-amino-5H-pyrrolo[3,2-d]pyrimidin-7-yl)methylamino)-4-(methylthio)butane-1,3-diol

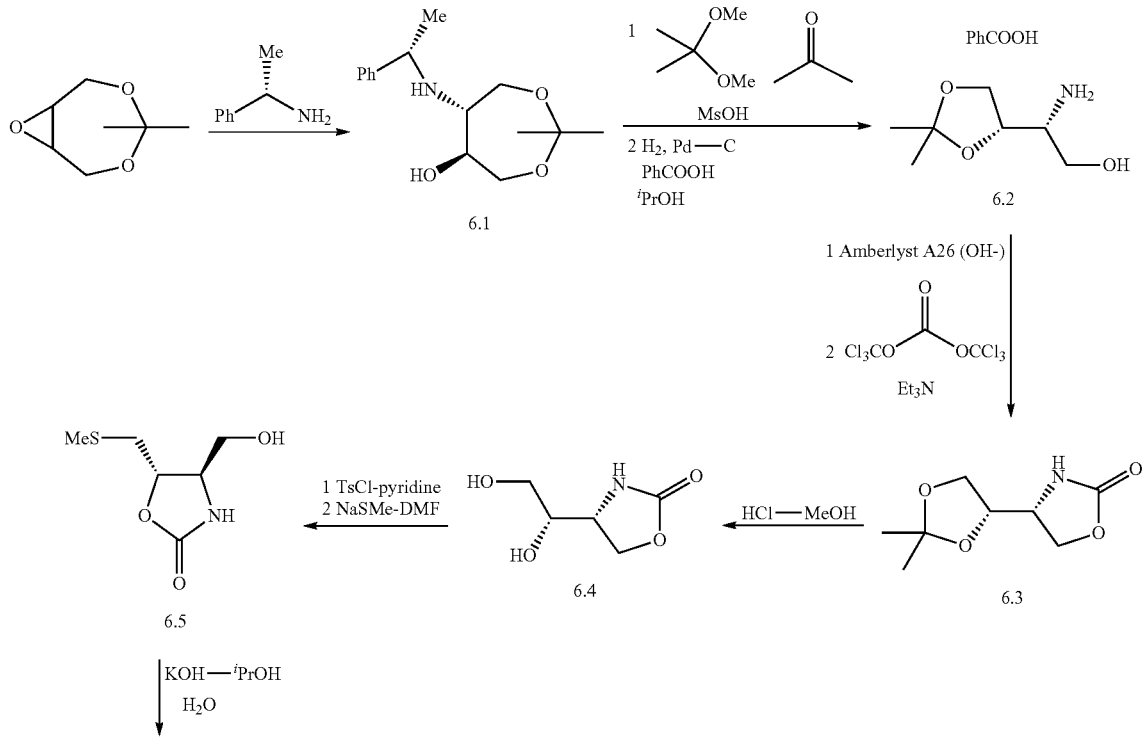

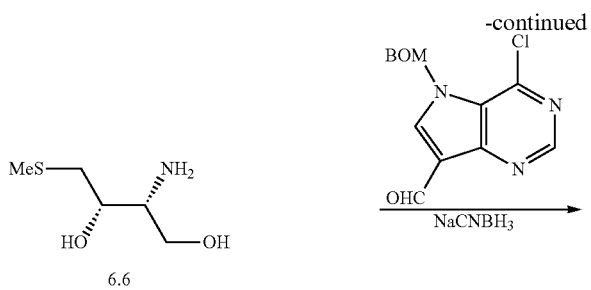
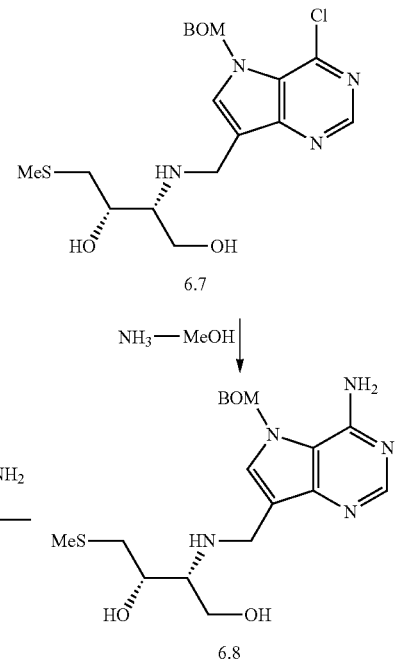

Example 6.1

Synthesis of (5S,6R)-2,2-dimethyl-6-((S)-1-phenyl-ethylamino)-1,3-dioxepan-5-ol

The known method by T. Inaba, A. G. Birchler, Y. Yamada, S. Sagawa, K. Yokata, K. Ando and I. Uchida, *J. Org. Chem.*, 1998, 63, 7582 for the preparation of the enantiomer of the title compound was followed. (S)-1-Phenylethanamine (30.4 ml, 236 mmol) and 4,4-dimethyl-3,5,8-trioxabicyclo[5.1.0] octane (34 g, 236 mmol) were dissolved in $^i$PrOH (16 ml) and heated under reflux for 16 h. The mixture was stirred and cooled in an ice bath. Hexanes (90 ml) was added. After 1 h the colourless crystalline solid was filtered off, washed with hexanes and dried to give (5S,6R)-2,2-dimethyl-6-((S)-1-phenylethylamino)-1,3-dioxepan-5-ol (21.9 g, 35%). The $^1$H NMR was in agreement with that described for the enantiomer of the title compound by T. Inaba, A. G. Birchler, Y. Yamada, S. Sagawa, K. Yokata, K. Ando and I. Uchida, *J. Org. Chem.*, 1998, 63, 7582. $[\alpha]^{D\ 20}$ −96.6 (c, 1.01, MeOH). Lit. (T. Inaba, A. G. Birchler, Y. Yamada, S. Sagawa, K. Yokata, K. Ando and I. Uchida, *J. Org. Chem.*, 1998, 63, 7582) $[\alpha]^{D\ 25}$ +96.2 (c 1.00, MeOH) for the enantiomer.

Example 6.2

Synthesis of (R)-2-amino-2-((S)-2,2-dimethyl-1,3-dioxolan-4-yl)ethanol benzoate

The known method by T. Inaba, Y. Yamada, H. Abe, S. Sagawa and H. Cho, *J. Org. Chem.*, 2000, 65, 1623 for the preparation of the enantiomer of the title compound was followed. Methanesulfonic acid (6.43 ml, 99 mmol) was added dropwise (exothermic) to a stirred suspension of compound 6.1 (21.9 g, 83 mmol) and 2,2-dimethoxypropane (1.023 ml, 8.25 mmol) in acetone (55 ml) keeping the temp. <25° C. by cooling in an ice bath. The solution was stirred a further 4 h at it then neutralized with sat. aq. NaHCO$_3$ and extracted with toluene (100 ml), dried (MgSO$_4$) and the solvent evaporated to give intermediate (R)-2-((S)-2,2-dimethyl-1,3-dioxolan-4-yl)-2-((S)-1-phenylethylamino)ethanol (21.2 g). A portion of the latter compound (11.2 g, 42.2 mmol) and benzoic acid (5.15 g, 42.2 mmol) were dissolved in $^i$PrOH (60 ml) and placed in a glass insert inside a steel bomb hydrogenator. It was hydrogenated (without any metallic contact between the apparatus and solution) at 15 bar and 40° C. for 20 h. The mixture was filtered warm through Celite then hexanes added to the filtrate and the cooled in an ice bath. After 1 h crystalline (R)-2-amino-2-((S)-2,2-dimethyl-1,3-dioxolan-4-yl)ethanol benzoate was filtered off and dried (7.64 g, 64%). The $^1$H NMR was in agreement with that for the enantiomer described in T. Inaba, Y. Yamada, H. Abe, S. Sagawa and H. Cho, *J. Org. Chem.*, 2000, 65, 1623.

Example 6.3

Synthesis of (R)-4-((S)-2,2-dimethyl-1,3-dioxolan-4-yl)oxazolidin-2-one

The product from Example 6.2 (7.2 g, 25.4 mmol) was dissolved in MeOH (30 ml) and passed through a column of Amberlyst A26 resin (OH) (5×18 cm), eluted with MeOH. Fractions containing product were collected and the solvent evaporated to give (R)-2-amino-2-((S)-2,2-dimethyl-1,3-dioxolan-4-yl)ethanol as a yellow gum (4.1 g, 25.4 mmol). This was dissolved in dry CH$_2$Cl$_2$ (60 ml), cooled in an ice bath and triethylamine (10.75 ml, 76 mmol) added. To this solution was added triphosgene (2.72 g, 9.18 mmol) in portions over 60 min then the mixture stirred for 20 min. The solvent was evaporated and the residue chromatographed on silica gel (EtOAc-hexanes, 8:2) to give (R)-4-((S)-2,2-dimethyl-1,3-dioxolan-4-yl)oxazolidin-2-one (4.4 g, 92%) as a colourless solid. A sample was recrystallized from EtOAc-hexanes. Mpt 126-127° C. $^1$H NMR (CDCl$_3$, referenced to the centre line of CDCl$_3$ at 77.0 ppm) δ ppm 6.18 (br.s, 1H, exchanged to D$_2$O), 4.44 (t, J=8.8 Hz, 1H), 4.20-4.06 (m, 3H), 3.91 (m, 1H), 3.74 (dd, J=8.5, 4.7 Hz, 1H), 1.44 (s, 3H), 1.35 (s, 3H). $^{13}$C NMR (CDCl$_3$) δ 159.6, 110.2, 76.6, 66.3, 65.5, 54.6, 26.5, 24.8.

$[\alpha]_D^{21}$ −50.7 (c 0.8, MeOH). +ESMS Found 210.0737 (M+Na)$^+$ C$_8$H$_{13}$NNaO$_4$ requires 210.0742. Found C, 51.46%, H, 6.79%, N, 7.49%. C$_8$H$_{13}$NO$_4$ requires C, 51.33% H, 7.00% N, 7.48%.

Example 6.4

Synthesis of (R)-4-((S)-1,2-dihydroxyethyl)oxazolidin-2-one

The product from Example 6.3 (5.8 g, 31.0 mmol) was dissolved in a mixture of MeOH (80 ml) and acetyl chloride (0.441 ml, 6.20 mmol). The mixture was stirred at rt for 4 h then the solvent evaporated. The residue was again dissolved in MeOH (80 ml) and acetyl chloride (0.5 ml) added. The mixture was stirred a further 1 h. The solvent was evaporated and the residue chromatographed on silica gel (CH$_2$Cl$_2$-MeOH, 9:1 then 85:15) to give (R)-4-((S)-1,2-dihydroxyethyl)oxazolidin-2-one (4.23 g, 93%) as a colourless gum. $[\alpha]^{D\,21}$ −63.0 (c 0.9, MeOH). NMR (CD$_3$OD, 300 MHz), δ ppm 4.47 (t, J=8.8 Hz, 1H), 4.30 (dd, J=8.7, 6.0 Hz, 1H), 3.97 (m, 1H), 3.62-3.49 (m, 3H). $^{13}$C NMR (CD$_3$OD, referenced to the centre line of CD$_3$OD at 49.0 ppm) δ 162.7, 73.7, 68.6, 64.3, 55.9. +ESMS Found 170.0431 (M+Na)$^+$ C$_5$H$_9$NNaO$_4$ requires 170.0429.

Example 6.5

Synthesis of (4R,5S)-4-(hydroxymethyl)-5-(methylthiomethyl)oxazolidin-2-one p-Toluenesulfonyl chloride (2.208 g, 11.58 mmol) was added to a solution of the product from Example 6.4 (1.42 g, 9.65 mmol) in dry pyridine (10 ml) at 0° C. The mixture was warmed to rt and stirred for 3 h. More p-toluenesulfonyl chloride (442 mg, 2.3 mmol) was added and the mixture stirred at rt for 16 h. The solvent was evaporated and the residue chromatographed on silica gel (EtOAc-hexane, 6:4, then EtOAc) to give the intermediate primary tosylate as a colourless solid (1.77 g, 5.9 mmol). The latter compound was dissolved in DMF (7 ml) and sodium thiomethoxide (827 mg, 11.8 mmol) added. The mixture was stirred at rt for 3 h then the solvent evaporated and the residue chromatographed on silica gel (CH$_2$Cl$_2$-MeOH, 98:2 then 95:5) to give (4R,5S)-4-(hydroxymethyl)-5-(methylthiomethyl)oxazolidin-2-one as a colourless gum which solidified on standing a short while. An analytical sample was recrystallized from EtOH-hexanes. Mpt 71-72° C. $^1$H NMR (CDCl$_3$) δ 6.46 (s, 1H, exchanged to D$_2$O), 4.56 (m, 1H), 3.82-3.73 (m, 2H, became a changed m after D$_2$O exchange), 3.63 (m, 1H, became a changed m after D$_2$O exchange), 3.41 (br. t, 1H, exchanged to D$_2$O), 2.88 (dd, J=14.0, 4.9 Hz, 1H), 2.75 (dd, J=14.0, 7.5 Hz, 1H), 2.19 (s, 3H). $^{13}$C NMR (CDCl$_3$, referenced to the centre line of CDCl$_3$ at 77.0 ppm) δ 159.9, 77.7, 63.5, 58.7, 37.6, 16.2. +ESMS Found 200.0358 (M+Na)$^+$ C$_6$H$_{11}$NNaO$_3$S requires 200.0357. $[\alpha]_D^{21}$ +79.5 (c 0.8, MeOH). Found 40.84% C, 6.46% H, 7.85% N, C$_6$H$_{11}$NO$_3$S, requires C, 40.66%, H, 6.26%, N, 7.90%.

Example 6.6

Synthesis of (2R,3S)-2-amino-4-(methylthio)butane-1,3-diol

The product from Example 6.5 (1.16 g, 6.55 mmol) was dissolved in a mixture of iPrOH (32 ml) and 2M aq. KOH (14 ml) and stirred at 80° C. for 4 h. The solvent was evaporated and the residue chromatographed on silica gel (CH$_2$Cl$_2$-MeOH-28% aq. NH$_4$OH, 9:1:0.1) to give (2R,3S)-2-amino-4-(methylthio)butane-1,3-diol (0.932 g, 94%) as a yellow solid.

$[\alpha]_D^{21}$ +3.7 (c 1.11, MeOH). $^1$H NMR (CO$_3$OD) δ 3.75 (m, 1H), 3.60 (dd, J=10.8, 5.7 Hz, 1H), 3.51 (dd, J=10.8, 6.4 Hz, 1H), 2.84 (m, 1H), 2.72 (dd, J=13.6, 5.5 Hz, 1H), 2.61 (dd, J=13.6, 7.5 Hz, 1H), 2.13 (s, 3H). $^{13}$C NMR (CD$_3$OD, referenced to the centre line of CD$_3$OD at 49.0 ppm) 71.0, 65.1, 56.5, 39.2, 15.9. +ESMS Found 152.0750 (M+H)$^+$ C$_5$H$_{14}$NO$_2$S requires 152.0745.

Example 6.7

Synthesis of (2R,3S)-2-((5-(benzyloxymethyl)-4-chloro-5H-pyrrolo[3,2-d]pyrimidin-7-yl)methylamino)-4-(methylthio)butane-1,3-diol Sodium cyanoborohydride (0.036 g, 0.567 mmol) was added to a solution of the product from Example 6.6 (0.066 g, 0.436 mmol), 5-(benzyloxymethyl)-4-chloro-5H-pyrrolo[3,2-d]pyrimidine-7-carbaldehyde (0.132. mg, 0.436 mmol) and acetyl chloride (10.24 μl, 0.144 mmol) in MeOH (5 ml). The mixture was stirred at rt for 4 h. then the solvent evaporated and the residue chromatographed on silica gel (CH$_2$Cl$_2$-7M NH$_3$ in MeOH, 97:3) to give (2R,3S)-2-((5-(benzyloxymethyl)-4-chloro-5H-pyrrolo[3,2-d]pyrimidin-7-yl) methylamino)-4-(methylthio)butane-1,3-diol (0.12 g, 63%) as yellow gum. $^1$H NMR (CD$_3$OD, 300 MHz) δ ppm 8.60 (s, 1H), 7.87 (s, 1H), 7.20 (m, 5H), 5.86 (s, 2H), 4.54 (s, 2H), 4.12 (d, J=13.8 Hz, 1H), 3.99 (d, J=13.8 Hz, 1H), 3.84-3.73 (m, 2H), 3.64 (dd, J=11.2, 5.1 Hz, 1H), 2.82-2.72 (m, 2H), 2.55 (dd, J=13.5, 7.4 Hz, 1H), 2.04 (s, 3H). $^{13}$C NMR (CD$_3$OD, referenced to centre line of CD$_3$OD at 49.0 ppm) δ 152.9, 150.5, 143.8, 138.6, 138.4, 129.3, 128.8, 128.6, 125.5, 116.6, 78.2, 71.6, 71.3, 62.2, 62.0, 41.9, 39.2, 16.0. +ESMS Found 437.1416 (M+H)$^+$ C$_{20}$H$_{26}^{35}$ClN$_4$O$_3$S requires 437.1414.

Example 6.8

Synthesis of (2R,3S)-2-((4-amino-5-(benzyloxymethyl)-5H-pyrrolo[2,3-d]pyrimidin-7-yl)methylamino)-4-(methylthio)butane-1,3-diol The product from Example 6.7 (0.19 g, 0.435 mmol) was stirred in 7M NH$_3$-MeOH (25 ml) for 24 h in a sealed tube at 135° C. (oil bath). After cooling to rt the solvent was evaporated and the residue chromatographed on silica gel (CH$_2$Cl$_2$-7M NH$_3$-MeOH 96.5:3.5 then 95:5) to give (2R,3S)-2-((4-amino-5-(benzyloxymethyl)-5H-pyrrolo[3,2-d]pyrimidin-7- yl)methylamino)-4-(methylthio)butane-1,3-diol (0.108 g, 60%) as a yellow gum. $^1$H NMR (CD$_3$OD) δ 8.17 (s, 1H), 7.46 (s, 1H), 7.28 (m, 5H), 5.63 (s, 2H), 4.57 (s, 2H), 4.07 (d, J=13.7 Hz, 1H), 3.91 (d, J=13.7 Hz, 1H), 3.81-3.73 (m, 2H), 3.64 (dd, J=11.4, 5.0 Hz, 1H), 2.81-2.69 (m, 2H), 2.54 (dd, J=13.5, 7.4 Hz, 1H), 2.04 (s, 3H). $^{13}$C NMR (CD$_3$OD, referenced to the centre line of CD$_3$OD at 49.0 ppm) δ 152.8, 151.5, 149.4, 137.8, 133.6, 129.5, 129.3, 129.2, 116.2, 115.1, 78.6, 71.4, 71.3, 62.1, 62.0, 42.0, 39.3, 16.0. +ESMS Found 418.1907 (M+H)$^+$ C$_{20}$H$_{28}$N$_5$O$_3$S requires 418.1913.

Example 6.9

Synthesis of (2R,3S)-2-((4-amino-5H-pyrrolo[3,2-d]pyrimidin-7-yl)methylamino)-4-(methylthio)butane-1,3-diol The product from Example 6.8 (0.106 g, 0.254 mmol) was dissolved in 7M NH$_3$-MeOH solution (10 ml), Pd black (106 mg) was added followed by hydrazine hydrate (1.5 ml). The mixture was stirred for 1 h then filtered and the solvent evaporated. The residue was chromatographed on silica gel (CH$_2$Cl$_2$-7M NH$_3$ in MeOH, 85:15) to give (2R,3S)-2-((4-amino-5H-pyrrolo[3,2-d]pyrimidin-7-yl)methylamino)-4-(methylthio)butane-1,3-diol (0.056 g, 74%) as a colourless solid. [α]$_D^{20}$ −8.4 (c, 0.695, MeOH). $^1$H NMR (CD$_3$OD) 8.16 (s, 1H), 7.47 (s, 1H), 4.11 (d, j=13.6 Hz, 1H), 3.97 (d, J=13.6 Hz, 1H), 3.84-3.74 (m, 2H), 3.64 (dd, J=11.5, 5.0 Hz, 1H), 2.81 (q, J=5.1 Hz, 1H), 2.72 (dd, J=13.6, 4.7 Hz, 1H), 2.55 (dd, J=13.6, 7.6 Hz, 1H), 2.06 (s, 3H). $^{13}$C NMR (CD$_3$OD, referenced to the centre line of CD$_3$OD at 49.0 ppm) δ 152.0, 150.8, 146.5, 129.1, 115.5, 114.9, 71.2, 62.5, 61.8, 42.2, 39.3, 16.0. +ESMS Found 298.1333 (M+H)$^+$ C$_{12}$H$_{20}$N$_5$O$_2$S requires 298.1338.

Example 7

Synthesis of (2S,3R)-2-((4-amino-5H-pyrrolo[3,2-d]pyrimidin-7-yl)methylamino)-4-(methylthio)butane-1,3-diol

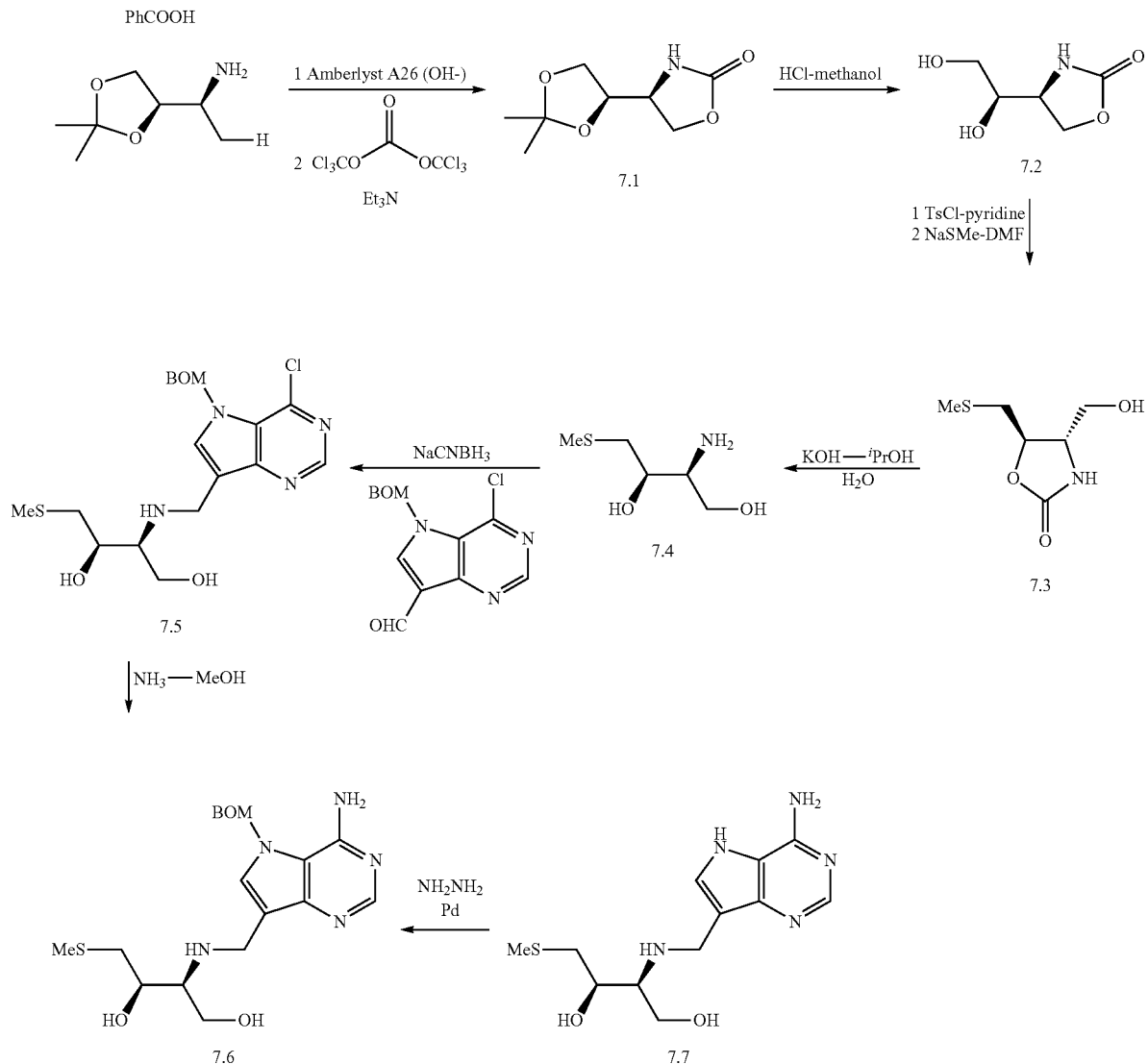

Example 7.1

Synthesis of (S)-4-((R)-2,2-dimethyl-1,3-dioxolan-4-yl)oxazolidin-2-one (S)-2-Amino-2-((R)-2,2-dimethyl-1,3-dioxolan-4-yl)ethanol benzoate (prepared as described in T. Inaba, Y. Yamada, H. Abe, S. Sagawa and H. Cho, *J. Org. Chem.*, 2000, 65, 1623) was converted into (S)-4-((R)-2,2-dimethyl-1,3-dioxolan-4-yl)oxazolidin-2-one as a colourless solid in the same way described for the synthesis of the enantiomer product of Example 6.3. The $^1$H and $^{13}$C NMR spectra were identical to those of the enantiomer product of Example 6.3. $[\alpha]_D^{21}$ +50.5 (c 0.8, MeOH). +ESMS Found 210.0741 (M+Na)$^+$ $C_8H_{13}NNaO_4$ requires 210.0742.

Example 7.2

Synthesis of (S)-4-((R)-1,2-dihydroxyethyl)oxazolidin-2-one

The product from Example 7.1 was converted into (S)-4-((R)-1,2-dihydroxyethyl)oxazolidin-2-one as a colourless gum in the same way described for the synthesis of the enantiomer product of Example 6.4. The $^1$H and $^{13}$C NMR spectra were identical to those of the enantiomer product of Example 6.4. $[\alpha]_D^{21}$ +62.8 (c 0.9, MeOH). +ESMS Found 170.0427 (M+Na)$^+$ $C_5H_9NNaO_4$ requires 170.0429.

Example 7.3

Synthesis of (4S,5R)-4-(hydroxymethyl)-5-(methylthiomethyl)oxazolidin-2-one

The product from Example 7.2 was converted into (4S,5R)-4-(hydroxymethyl)-5-(methylthiomethyl)oxazolidin-2-one as a solid in the same way described for the synthesis of the enantiomer product of Example 6.5. The $^1$H and $^{13}$C NMR spectra were identical to those of the enantiomer product of Example 6.5. +ESMS Found 200.0357 (M+Na)$^+$ $C_6H_{11}NNaO_3S$ requires 200.0357.

Example 7.4

Synthesis of (2S,3R)-2-amino-4-(methylthio)butane-1,3-diol

The product from Example 7.3 was converted into (2S,3R)-2-amino-4-(methylthio)butane-1,3-diol as a solid in the same way described for the synthesis of the enantiomer product of Example 6.6. The $^1$H and $^{13}$C NMR spectra were identical to those of the enantiomer product of Example 6.6. $[\alpha]_D^{21}$ −3.5 (c1.09, MeOH). +ESMS Found 152.0744 (M+H)$^+$ $C_5H_{14}NO_2S$ requires 152.0745.

Example 7.5

Synthesis of (2S,3R)-2-((5-(benzyloxymethyl)-4-chloro-5H-pyrrolo[3,2-d]pyrimidin-7-yl)methylamino)-4-(methylthio)butane-1,3-diol The product from Example 7.4 was converted into (2S,3R)-2-((5-(benzyloxymethyl)-4-chloro-5H-pyrrolo[3,2-d]pyrimidin-7-yl)methylamino)-4-(methylthio)butane-1,3-diol as a yellow gum in the same way described for the synthesis of the enantiomer product of Example 6.7. The $^1$H and $^{13}$C NMR spectra were identical to those of the enantiomer product of Example 6.7. +ESMS Found 437.1422 (M+H)$^+$ $C_{20}H_{26}^{35}ClN_4O_3S$ requires 437.1414.

Example 7.6

Synthesis of (2S,3R)-2-((4-amino-5-(benzyloxymethyl)-5H-pyrrolo[3,2-d]pyrimidin-7-yl)methylamino)-4-(methylthio)butane-1,3-diol The product from Example 7.5 was converted into (2S,3R)-2-((4-amino-5-(benzyloxymethyl)-5H-pyrrolo[3,2-d]pyrimidin-7-yl)methylamino)-4-(methylthio)butane-1,3-diol as a yellow gum in the same way described for the synthesis of the enantiomer product of Example 6.8. The $^1$H and $^{13}$C NMR spectra were identical to those of the enantiomer product of Example 6.8. +ESMS Found 418.1909 (M+H)$^+$ $C_{20}H_{28}N_5O_3S$ requires 418.1913.

Example 7.7

Synthesis of (2S,3R)-2-((4-amino-5H-pyrrolo[3,2-d]pyrimidin-7-yl)methylamino)-4-(methylthio)butane-1,3-diol The product from Example 7.6 was converted into (2S,3R)-2-((4-amino-5H-pyrrolo[3,2-d]pyrimidin-7-yl)methylamino)-4-(methylthio)butane-1,3-diol as a colourless solid in the same way described for the synthesis of the enantiomer product of Example 6.9. The $^1$H and $^{13}$C NMR spectra were identical to those of the enantiomer product of Example 6.9. $[\alpha]_D^{20}$ +8.2 (c, 0.68, MeOH). +ESMS Found 298.1335 (M+H)$^+$ $C_{12}H_{20}N_5O_2S$ requires 298.1338.

Example 8

Synthesis of (2R,3S)-2-(((4-amino-5H-pyrrolo[3,2-d]pyrimidin-7-yl)methyl)(methyl)amino)-4-(methylthio)butane-1,3-diol

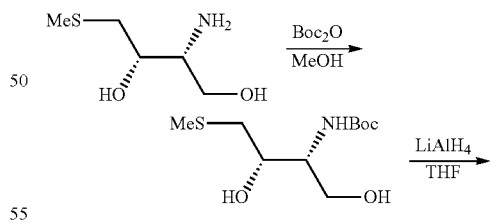

8.1

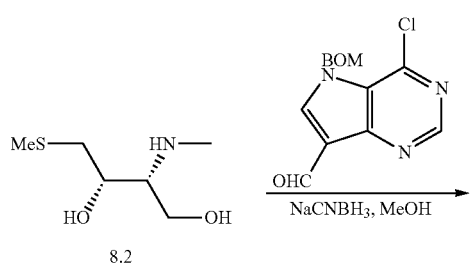

8.2

41

-continued

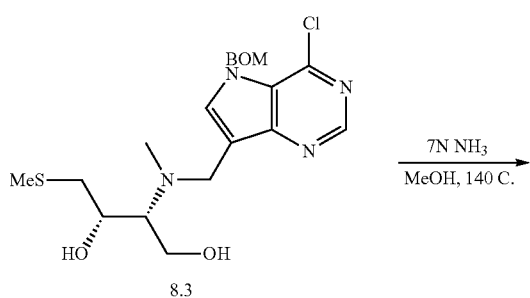

8.3

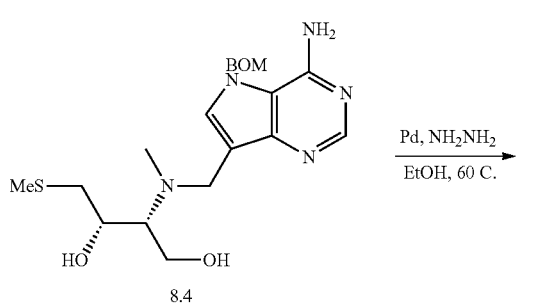

8.4

[structure 8.5]

8.5

Example 8.1

Synthesis of tert-butyl(2R,3S)-1,3-dihydroxy-4-(methylthio)butan-2-ylcarbamate

Di-tert-butyl dicarbonate (548 mg, 2.5 mmol) was added to a stirred solution of (2R,3S)-2-amino-4-(methylthio)butane-1,3-diol (190 mg, 1.3 mmol) in methanol (5 ml) at ambient and the reaction monitored by TLC. After 1 h the reaction was complete by TLC analysis therefore concentrate in vacuo and purify the resulting residue by flash chromatography on silica gel eluting with DCM=>5% 7N NH3 in MeOH/DCM to afford tert-butyl (2R,3S)-1,3-dihydroxy-4-(methylthio)butan-2-ylcarbamate (313 mg, 99% yield) as a syrup. $^1$H NMR (CDCl$_3$) δ 3.99 (brs, 1H), 3.73 (m, 2H), 3.58 (d, J=2.0 Hz, 2H), 3.33 (brs, 1H), 2.63 (m, 2H), 2.12 (s, 3H), 1.45 (s, 9H). $^{13}$C NMR (CDCl$_3$) δ 157.2, 80.6, 69.9, 65.0, 54.8, 39.4, 29.1, 16.2.

42

Example 8.2

Synthesis of (2R,3S)-2-(methylamino)-4-(methylthio)butane-1,3-diol

Lithium aluminium hydride (3 ml, 2M in THF, 6.0 mmol) was added dropwise to a solution of tert-butyl(2R,3S)-1,3-dihydroxy-4-(methylthio)butan-2-ylcarbamate (316 mg, 1.3 mmol) in tetrahydrofuran (5 ml) and the resulting suspension heated to reflux and left overnight. The reaction was cooled to ambient, quenched with water (0.25 ml), 15% aq NaOH (0.25 ml), and water (0.75 ml) and the resulting white suspension left to stir for 30 minutes. The suspension was then filtered through Celite®, washed with hot ethyl acetate, and the filtrate concentrated in vacuo to afford a mobile oil. The residue was purified by flash chromatography on silica gel eluting with 5% 7 N NH$_3$ in MeOH/DCM to afford the title compound as an oil (120 mg, 57%). $^1$H NMR (CDCl$_3$) δ 3.78 (m, 2H), 3.58 (dd, J=11.5, 3.9 Hz, 1H), 2.78 (dd, J=13.6, 4.3 Hz, 1H 1H), 2.64 (dd, J=13.6, 8.2 Hz, 1H), 2.50 (m, 1H), 2.47 (s, 3H), 2.15 (s, 3H). $^{13}$C NMR (CDCl$_3$) δ 70.4, 64.5, 61.0, 39.7, 35.3, 16.6.

Example 8.3

Synthesis of (2R,3S)-2-(((5-(benzyloxymethyl)-4-chloro-5H-pyrrolo[3,2-d]pyrimidin-7-yl)methyl)(methyl)amino)-4-(methylthio)butane-1,3-diol Sodium cyanoborohydride (68 mg, 1.1 mmol) was added to a stirred solution of (2S,3R)-2-(methylamino)-4-(methylthio)butane-1,3-diol (120 mg, 0.7 mmol) and 5-(benzyloxymethyl)-4-chloro-5H-pyrrolo[3,2-d]pyrimidine-7-carbaldehyde (263 mg, 0.9 mmol) in methanol (2 ml) and the resulting reaction left for 48 h. The reaction was concentrated in vacuo and the resulting residue purified by flash chromatography on silica gel eluting with 5% MeOH/DCM=>10% MeOH/DCM to afford, presumably, (2S,3R)-2-(((5-(benzyloxymethyl)-4-chloro-5H-pyrrolo[3,2-d]pyrimidin-7-yl)methyl)(methyl)amino)-4-(methylthio)butane-1,3-diol B.4 (220 mg, 67% yield) as a syrup which was used in the next step without purification.

Example 8.4

Synthesis of (2R,3S)-2-(((4-amino-5-(benzyloxymethyl)-5H-pyrrolo[3,2-d]pyrimidin-7-yl)methyl)(methyl)amino)-4-(methylthio)butane-1,3-diol A solution of (2R,3S)-2-(((5-(benzyloxymethyl)-4-chloro-5H-pyrrolo[3,2-d]pyrimidin-7-yl)methyl)(methyl)amino)-4-(methylthio)butane-1,3-diol (240 mg, 0.5 mmol) in 7N NH3 in MeOH (5 ml) was heated in a sealed tube at 140 C (bath temp) overnight. The reaction was concentrated in vacuo and the resulting residue purified by flash chromatography on silica gel eluting with 10%. MeOH/DCM=>10% 7 N NH3 to afford (2R,3S)-2-(((4-amino-5-(benzyloxymethyl)-5H-pyrrolo[3,2-d]pyrimidin-7-yl)methyl)(methyl)amino)-4-(methylthio)butane-1,3-diol (120 mg, 52%) as a syrup. $^1$H NMR (CD$_3$OD) δ 8.16 (s, 1H), 7.41 (s, 1H), 7.27 (m, 5H), 5.60 (s, 2H), 4.57 (s, 2H), 4.07 (d, J=15.0 Hz, 1H), 3.82 (m, 3H), 3.71 (dd, J=12.0, 6.0 Hz, 1H), 2.88 (m, 1H), 2.77 (dd, J=15.0, 3.0 Hz, 1H), 2.54 (dd, J=15.0, 6.0 Hz, 1H), 2.43 (s, 3H), 2.03 (s, 3H). $^{13}$C NMR (CD$_3$OD) δ 153.2, 151.8, 150.4, 138.2, 134.4, 130.0, 129.7, 129.6, 116.8, 115.3, 79.0, 71.8, 70.8, 67.0, 60.2, 50.0, 40.2, 39.1, 16.8.

Example 8.5

Synthesis of (2R,3S)-2-(((4-amino-5H-pyrrolo[3,2-d]pyrimidin-7-yl)methyl)(methyl)amino)-4-(methylthio)butane-1,3-diol Hydrazine hydrate (0.56 ml, 11.6 mmol) was added dropwise to a suspension of (2S,3R)-2-(((4-amino-5-(benzyloxymethyl)-5H-pyrrolo[3,2-d]pyrimidin-7-yl)methyl)(methyl)amino)-4-(methylthio)butane-1,3-diol (50 mg, 116 μmol), palladium black (50 mg, 47.0 μmol) and ethanol (2 ml). Upon complete addition of the hydrazine the palladium went from a fine suspension to a granular form. The reaction was warmed to 60 C at which point TLC analysis indicated the reaction was complete therefore the reaction was cooled to ambient temperature, the palladium black removed by filtration and the filtrate concentrated in vacuo, and the crude residue co-distilled with ethanol and toluene (50 ml, 2:1 v/v). The resulting residue was purified by flash chromatography on silica gel eluting with 20% 7N NH$_3$ in MeOH/DCM to afford (2S,3R)-2-(((4-amino-5H-pyrrolo[3,2-d]pyrimidin-7-yl)methyl)(methyl)amino)-4-(methylthio)butane-1,3-diol (30 mg, 96 μmol, 83% yield) as a colourless syrup. $^1$H NMR (CD$_3$OD) δ 8.16 (s, 1H), 7.43 (s, 1H), 4.11 (d, J=13.4 Hz, 1H), 3.86 (m, 3H), 3.73 (dd, J=11.5, 5.0 Hz, 1H), 2.88 (m, 1H), 2.77 (dd, J=13.7, 3.9 Hz, 1H), 2.54 (dd, J=13.6, 7.0 Hz, 1H), 2.43 (s, 3H), 2.07 (s, 3H). $^{13}$C NMR (CD$_3$OD) 152.4, 151.0, 147.6, 129.8, 116.1, 115.4, 70.8, 67.2, 60.1, 50.3, 40.2, 38.8, 16.7.

Example 9

Synthesis of (2RS,3RS)-2-{[(4-amino-5H-pyrrolo[3,2-d]pyrimidin-7-yl)methylamino]methyl}-4-(methylthio)butane-1,3-diol

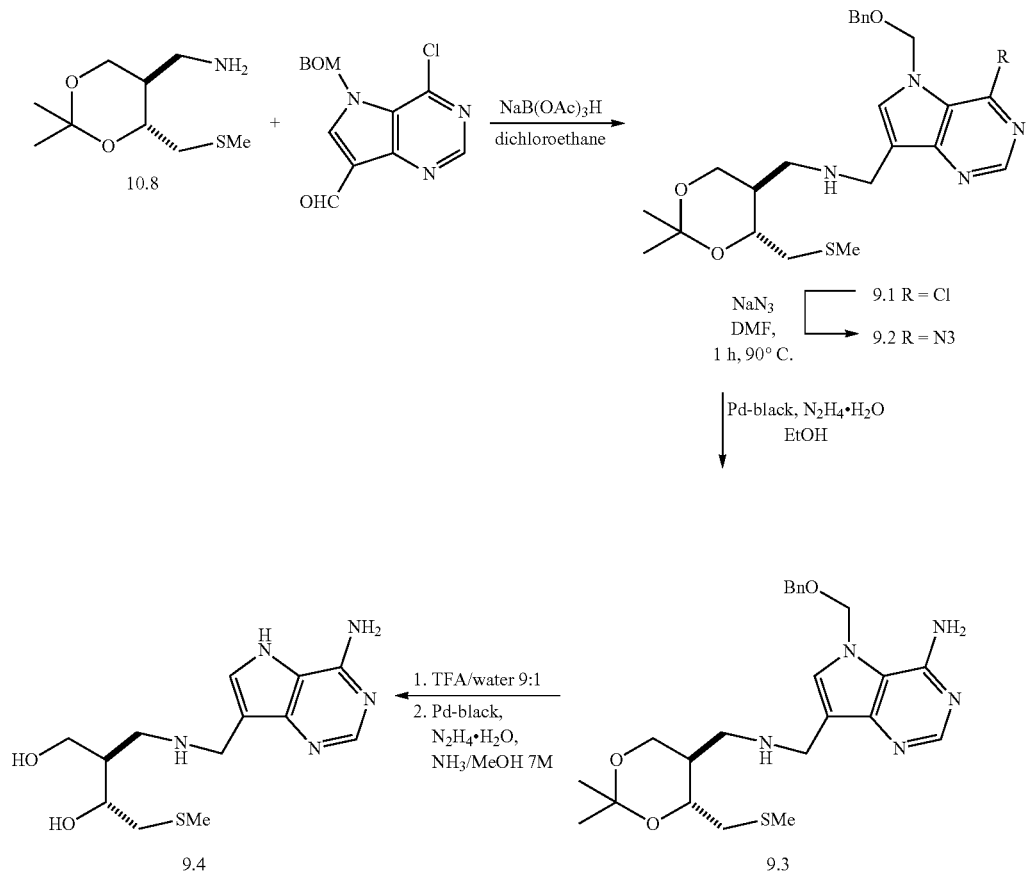

Example 9.1

Synthesis of 1-[5-(benzyloxymethyl)-4-chloro-5H-pyrrolo[3,2-d]pyrimidin-7-yl]-N-{[(4RS,5RS)-2,2-dimethyl-4-(methylthiomethyl)-1,3-dioxan-5-yl]methyl}methanamine To a stirred solution of compound from Example 10.8 (75 mg, 0.37 mmol) and 5-(benzyloxymethyl)-4-chloro-5H-pyrrolo[3,2-d]pyrimidine-7-carbaldehyde (121 mg, 0.40 mmol) in 1,2-dichloroethane (5 mL) was added Na(OAc)$_3$BH (154 mg, 0.69 mmol) at room temperature. After 45 min saturated aqueous NaHCO$_3$ (10 mL) was added, vigorously stirred and the organic layer was separated, the aqueous layer was extracted with CHCl$_3$ (5 mL), and the combined organic layers were dried (MgSO$_4$), filtered and evaporated. The residue was preabsorbed on silica and purified by chromatography (~20 g silica, CHCl$_3$, then CHCl$_3$/MeOH=15:1 v/v) which gave compound 9.1 product as colourless oil (122 mg, 68%). R$_f$=0.30 (CHCl$_3$/MeOH=15:1 v/v). $^1$H NMR (CDCl$_3$) δ 8.72 (s, 1H), 7.51, 7.37-7.22 (m, 5H), 5.82 (s, 2H), 4.54 (s, 2H), 4.05-3.89 (m, 3H), 3.84 (ddd, J=3.0, 6.9, 9.8 Hz, 1H), 3.67 (dd, J=9.9, 11.6 Hz, 1H), 2.80 (dd, J=2.9, 13.8 Hz, 1H), 2.66 (dd, J=4.9, 12.1 Hz, 1H), 2.63 (dd, J=6.8, 13.8 Hz, 1H), 2.50 (dd, J=7.6, 12.1 Hz, 1H), 2.15 (s, 3H), 2.13-1.93 (m, 2H), 1.42 (s, 3H), 1.38 (s, 3H). $^{13}$C NMR (CDCl$_3$, referenced to the middle chlorofrom peak at 77.4 ppm) δ 152.1, 150.2, 142.8, 136.7, 135.3, 128.8, 128.4, 127.9, 124.6, 116.1, 98.7, 76.8, 73.6, 70.8, 63.1, 48.6, 43.6, 39.1, 38.4, 29.2, 20.0, 17.3. HRMS: (M+H)$^+$ calcd. for C$_{24}$H$_{32}$N$_4$O$_3$S$^{35}$Cl: 491.1884. found: 491.1877.

Example 9.2

Synthesis of 1-[4-azido-5-(benzyloxymethyl)-5H-pyrrolo[3,2-d]pyrimidin-7-yl]-N-{[(4RS,5RS)-2,2-dimethyl-4-(methylthiomethyl)-1,3-dioxan-5-yl]methyl}methanamine Under Argon the product of Example 9.1 (120 mg, 0.24 mmol) was dissolved in dry DMF (5 ml), NaN$_3$ (48 mg, 0.73 mmol) was added and the mixture was heated to 90° C. After 1 h cooled to RT and concentrated in vacuo. The residue was suspended in CHCl3/MeOH and absorbed on silica in vacuo and purified by chromatography (~20 g silica, CHCl$_3$/MeOH=20:1 v/v) which gave the compound 9.2 as an oil (125 mg, 103%)—contained a trace of DMF. R$_f$=0.28 (CHCl$_3$/MeOH=20:1 v/v). $^1$H NMR (CDCl$_3$) δ 9.39 (s, 1H), 7.53 (s, 1H), 7.26-7.16 (m, 5H), 6.04 (s, 2H), 4.64 (s, 2H), 4.10-4.00 (m, 2H), 3.95 (dd, J=5.3, 11.7 Hz, 1H), 3.86 (ddd, J=2.9, 6.8, 9.7 Hz, 1H), 3.68 (dd, J=9.9, 11.6 Hz, 1H), 2.82 (dd, J=2.9, 13.9 Hz, 1H), 2.69 (dd, J=4.8, 12.1 Hz, 1H), 2.64 (dd, J=6.8, 13.8 Hz, 1H), 2.54 (dd, J=7.5, 12.1 Hz, 1H), 2.16 (s, 3H), 2.11-1.94 (m, 1H), 1.78 (br s, 1H), 1.43 (s, 3H), 1.39 (s, 3H). $^{13}$C NMR (CDCl$_3$, referenced to the middle chloroform peak at 77.4 ppm) δ 142.1, 138.7, 136.7, 131.6, 129.4, 128.6, 128.3, 127.9, 119.8, 113.7, 98.7, 78.3, 73.7, 71.8, 63.2, 48.7, 43.9, 39.1, 38.4, 29.2, 20.0, 17.3.

Example 9.3

Synthesis of 5-(benzyloxymethyl)-7-{{[(4RS,5RS)-2,2-dimethyl-4-(methylthiomethyl)-1,3-dioxan-5-yl]methylamino}methyl}-5H-pyrrolo[3,2-d]pyrimidin-4-amine The product from Example 9.2 (25 mg, 0.050 mmol) was dissolved in dry ethanol (2 mL) and Pd-black (25 mg, 0.24 mmol) was added, to the stirred mixture was added hydrazine hydrate (200 μL, 4.1 mmol). After 20 min the mixture was heated to 50° C. for 30 min. and then filtered through flux calcined diatomaceous earth. The filtrate was evaporated in vacuo and the residue was absorbed on silica and purified by chromatography (~5 g silica, CHCl$_3$/MeOH=9:1 v/v) which gave compound 9.3 as a colourless oil (17 mg, 73%). R$_f$=0.21 (CHCl$_3$/MeOH=9:1 v/v). $^1$H NMR (300 MHz, CDCl$_3$) δ 8.37 (s, 1H), 7.42-7.24 (m, 5H), 7.11 (s, 1H), 5.78 (br s, 2H), 5.49 (s, 2H), 4.56 (s, 2H), 4.06-3.90 (m, 3H), 3.85 (ddd, J=2.8, 7.0, 10.0 Hz, 1H), 3.69 (dd, J=10.0, 11.6 Hz, 1H), 2.81 (dd, J=2.8, 13.8 Hz, 1H), 2.70 (dd, J=4.8, 12.0 Hz, 1H), 2.63 (dd, J=7.0, 13.8 Hz, 1H), 2.54 (dd, J=7.7, 12.0 Hz, and br s 2H), 2.15 (s, 3H), 2.10-1.94 (m, 1H), 1.43 (s, 3H), 1.38 (s, 3H). HRMS: (M+H)$^+$ calcd. for C$_{24}$H$_{34}$N$_5$O$_3$S: 472.2382. found: 472.2368.

Example 9.4

Synthesis of (2RS,3RS)-2-{[(4-amino-5H-pyrrolo[3,2-d]pyrimidin-7-yl)methylamino]methyl}-4-(methylthio)butane-1,3-diol The product of Example 9.3 (17 mg, 0.036 mmol) was treated with TFA/water (9:1 v/v, 1 mL). After 5 min the mixture was evaporated in vacuo. The residue was redissolved in methanolic ammonia (7M, 4 mL) and Pd-black (17 mg, 0.16 mmol) was added, followed by hydrazine hydrate (250 μL, 5.1 mmol). After 15 min more Pd-black (22 mg, 0.21 mmol) was added and again after further 15 min (55 mg, 0.52 mmol) and also hydrazine hydrate (0.5 mL, 10.2 mmol). Shortly after the mixture was filtered through flux calcined diatomaceous earth and evaporated. The residue was dissolved in MeOH (2 mL) and treated with Amberlyst® A-26 (OH) ion exchange resin (~1 g) for 5 min, the solution was filtered and evaporated in vacuo which gave the product as an oil (7 mg, 62%). $^1$H NMR (CD$_3$OD) δ 8.16 (s, 1H), 7.48 (s, 1H), 3.97-3.80 (m, 2H), 3.79-3.61 (m, 2H), 3.16-3.05 (m, 1H), 2.85 (dd, J=6.0, 12.1, 1H), 2.79 (dd, J=6.7, 12.0 Hz, 1H), 2.66 (dd, J=4.8, 13.5 Hz, 1H), 2.56 (dd, J=8.0, 13.5 Hz, 1H), 2.11-1.88 (m, 4H). $^{13}$C NMR (CD$_3$OD, referenced to the middle methanol peak at 49.0 ppm) δ 150.8, 146.5, 129.1, 114.6, 72.1, 62.1, 45.5, 43.9, 40.1, 16.3. HRMS: (M+H)$^+$ calcd. for C$_{13}$H$_{22}$N$_5$O$_2$S: 312.1494. found: 312.1494.

Example 10
Synthesis of (2RS,3RS)-2-((((4-amino-5H-pyrrolo[3,2-d]pyrimidin-7-yl)methyl)(methyl)amino)methyl)-4-(methylthio)butane-1,3-diol
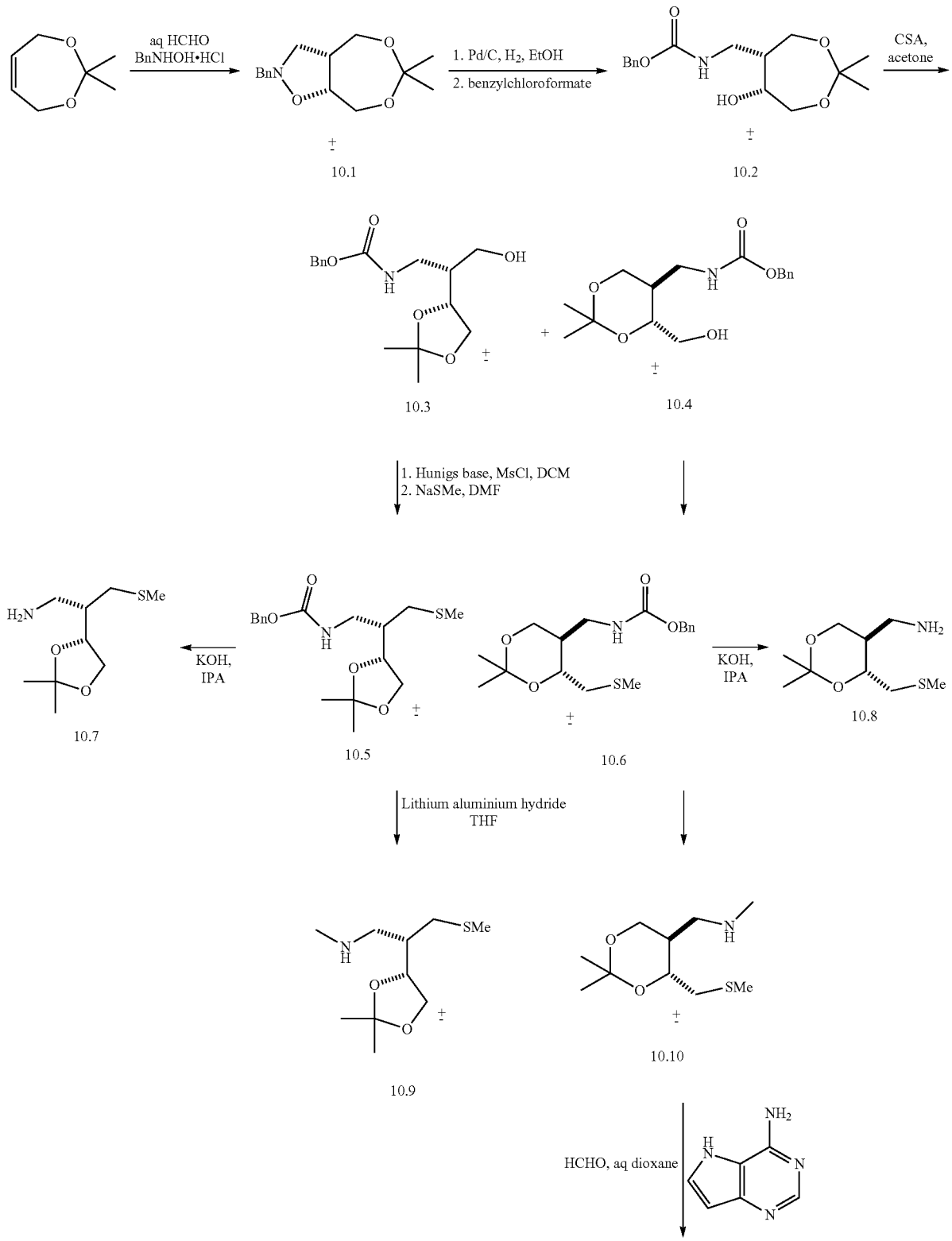

-continued

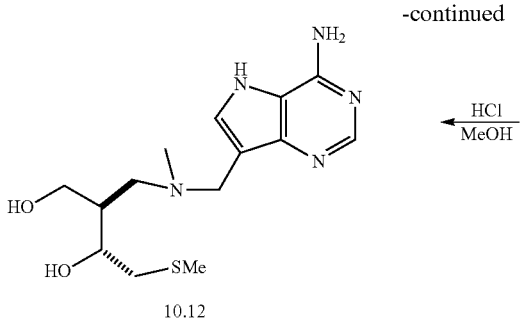

10.12

$\xleftarrow{\text{HCl}}{\text{MeOH}}$

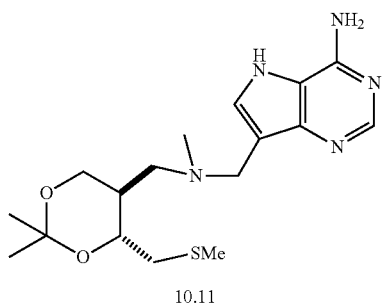

10.11

Example 10.1

Synthesis of (3aRS,8aRS)-2-benzyl-6,6-dimethyl-hexahydro-[1,3]dioxepino[5,6-d]isoxazole A mixture of N-benzylhydroxylamine hydrochloride (22.42 g, 140 mmol) and sodium acetate (15.36 g, 187 mmol) in ethanol (120 mL) was stirred at RT for 15 mins, and then 37% aq formaldehyde (20.91 ml, 281 mmol) was added and the resulting mixture was stirred again for 30 mins. Then added (Z)-2,2-dimethyl-4,7-dihydro-1,3-dioxepine (J. Org. Chem. 1976, 41, 2469) (12 g, 94 mmol) and the mixture was stirred and heated under reflux for 6 h. The mixture was concentrated to dryness and the residue was partitioned between chloroform and water, and the aq phase was adjusted to pH 8 with aq NaOH. The organic phase was washed again with aq NaHCO$_3$ and processed normally to a brown mobile syrup. Chromatography (EtOAc/Hex 1:2 then 1:1) gave the desired isoxazole (10.47 g, 39.8 mmol, 42.5% yield) as a yellow solid. $^1$H NMR (CDCl$_3$) δ 7.41-7.23 (m, 5H), 4.02-3.98 (m, 2H), 3.76 (m, 3H), 3.12 (brs, 1H), 2.74 (m, 2H), 1.35 (s, 6H). $^{13}$C NMR (CDCl$_3$) δ 137.2, 129.6, 128.7, 127.8, 102.2, 78.1, 64.1, 60.6, 60.4, 56.2, 45.8, 25.2, 24.2.

Example 10.2

Synthesis of benzyl ((5RS,6RS)-6-hydroxy-2,2-dimethyl-1,3-dioxepan-5-yl)methylcarbamate To a solution of (3aR/S,8aR/S)-2-benzyl-6,6-dimethyl-hexahydro-[1,3]dioxepino[5,6-d]isoxazole (10.4 g, 39.5 mmol) in ethanol (150 mL) was added 10% Pd/C (2.5 g) and the mixture was stirred under a hydrogen atmosphere. After 2 days the solids and solvent were removed. A solution of the residue in methanol (100 mL) and triethylamine (11.01 ml, 79 mmol) was cooled in an ice bath and benzyl chloroformate (7.30 ml, 51.3 mmol) was added, then the solution was allowed to warm to RT. Then chloroform was added and the solution was washed with water and processed normally. The crude residue was triturated with petroleum ether to give benzyl ((5R/S,6R/S)-6-hydroxy-2,2-dimethyl-1,3-dioxepan-5-yl)methylcarbamate (7.73 g, 24.99 mmol, 63.3% yield) as a white solid. $^{13}$C NMR (CDCl$_3$) δ 157.3, 136.9, 128.9, 128.5, 128.5, 102.1, 69.1, 67.2, 64.6, 59.8, 46.4, 40.0, 25.2, 25.0.

Examples 10.3 and 10.4

Synthesis of benzyl (RS)-2-((RS)-2,2-dimethyl-1,3-dioxolan-4-yl)-3-hydroxypropylcarbamate and benzyl ((4RS,5RS)-4-(hydroxymethyl)-2,2-dimethyl-1,3-dioxan-5-yl)methylcarbamate Camphorsulfonic acid (0.069 g, 0.296 mmol) was added to a solution of benzyl ((5R/S,6R/S)-6-hydroxy-2,2-dimethyl-1,3-dioxepan-5-yl)methylcarbamate (1.83 g, 5.92 mmol) in acetone (50 mL) and the solution was stirred at RT. After 40 mins chloroform was added and the solution was washed with aq NaHCO3 and then processed normally. Chromatography (EtOAc/Hex 1:1, and then 3:1) gave firstly benzyl (RS)-2-((RS)-2,2-dimethyl-1,3-dioxolan-4-yl)-3-hydroxypropylcarbamate (0.86 g, 2.78 mmol, 47.0% yield) and then benzyl ((4RS,5RS)-4-(hydroxymethyl)-2,2-dimethyl-1,3-dioxan-5-yl)methylcarbamate (0.942 g, 3.05 mmol, 51.5% yield) as syrups; compound 10.3 $^{13}$C NMR (CDCl$_3$) δ 157.6, 136.8, 128.9, 128.6, 128.5, 109.3, 76.4, 68.0, 67.3, 61.3, 44.3, 39.9, 26.9, 25.7; compound 10.4 $^{13}$C NMR (CDCl$_3$) δ 157.1, 136.8, 128.9, 128.6, 128.5, 99.0, 72.5, 69.1, 67.3, 64.2, 62.3, 40.3, 36.7, 29.1, 20.2.

Example 10.5

Synthesis of benzyl (SR)-2-((RS)-2,2-dimethyl-1,3-dioxolan-4-yl)-3-(methylthio)propylcarbamate To a solution of benzyl (RS)-2-((RS)-2,2-dimethyl-1,3-dioxolan-4-yl)-3-hydroxypropylcarbamate (0.843 g, 2.73 mmol) in dry dichloromethane (30 mL) was added diisopropylethylamine (1.351 ml, 8.18 mmol) and then methanesulfonyl chloride (0.274 ml, 3.54 mmol) and the resulting solution was stirred at RT. After 15 mins it was washed with water, dil HCl, and sat aq NaHCO$_3$ and then processed normally. A solution of the crude product in DMF (15 mL) was treated with sodium thiomethoxide (0.573 g, 8.18 mmol) and the mixture was stirred at RT for 1 h. Then toluene was added and the mixture was washed with water (×2) and processed normally. Chromatography (EtOAc/Hex 1:2) gave benzyl (SR)-2-((RS)-2,2-dimethyl-1,3-dioxolan-4-yl)-3-(methylthio)propylcarbamate (0.77 g, 2.268 mmol, 83% yield) as a syrup. $^{13}$C NMR (CDCl$_3$) δ 156.9, 136.9, 128.9, 128.5, 128.5, 109.3, 76.8, 67.7, 67.1, 41.9, 33.7, 26.9, 25.6, 16.6.

Example 10.6

Synthesis of benzyl((4RS,5RS)-2,2-dimethyl-4-(methylthiomethyl)-1,3-dioxan-5-yl)methylcarbamate To a solution of benzyl((4RS,5RS)-4-(hydroxymethyl)-2,2-dimethyl-1,3-dioxan-5-yl)methylcarbamate (0.884 g, 2.86 mmol) in dry dichloromethane (30 mL) was added diisopropylethylamine (1.417 ml, 8.57 mmol) and then methanesulfonyl chloride (0.288 ml, 3.71 mmol) and the solution was stirred at RT. After 30 mins the reaction mixture was washed with water, dil HCl and then sat aq NaHCO$_3$. Normal processing afforded a syrup, which was dissolved in DMF (15 mL) and then sodium thiomethoxide (0.601 g, 8.57 mmol) was added with stirring. After 1 h, toluene was added and the mixture was washed with water (×2) and processed normally. Chromatography (EtOAc/Hex 1:2) gave benzyl((4RS,5RS)-2,2-dimethyl-4-(methylthiomethyl)-1,3-dioxan-5-yl)methylcarbamate (0.839 g, 2.472 mmol, 86% yield) as a syrup. $^{13}$C NMR (CDCl$_3$) δ 156.9, 136.8, 128.9, 128.6, 128.5, 99.2, 72.3, 67.3, 62.4, 40.4, 39.9, 38.4, 29.0, 20.3, 17.3.

Example 10.7

Synthesis of (SR)-2-((RS)-2,2-dimethyl-1,3-dioxolan-4-yl)-3-(methylthio)propan-1-amine A solution of benzyl (SR)-2-((RS)-2,2-dimethyl-1,3-dioxolan-4-yl)-3-(methylthio)propylcarbamate (50 mg, 147 μmol) and potassium hydroxide (248 mg, 4419 μmol) in isopropanol (2 mL) was heated under reflux for 2 h. Silica gel was added and the mixture was concentrated to dryness, then applied to a silica gel column and eluted with 5% MeOH/CH$_2$Cl$_2$, then 7% 7N NH$_3$/MeOH in CH$_2$Cl$_2$ to give (SR)-2-((RS)-2,2-dimethyl-1,3-dioxolan-4-yl)-3-(methylthio)propan-1-amine (25 mg, 122 μmol, 83% yield) as a syrup. $^1$H NMR (CDCl$_3$) δ 4.20 (1H, dd, J=6.6, 13.5 Hz), 4.06 (1H, dd, J=6.3, 8.0 Hz); 3.70 (1H, t, J=7.7 Hz); 2.82-2.74 (3H, m); 2.61 (1H, dd, J=8.0, 13.0 Hz); 2.13 (3H, s); 1.85-1.75 (1H, m); 1.41 (3H, s); 1.35 (3H, s). $^{13}$C NMR (CDCl$_3$) δ 109.1, 76.9, 67.9, 44.5, 42.3, 33.7, 26.9, 25.7, 16.8.

Example 10.8

Synthesis of ((4RS,5RS)-2,2-Dimethyl-4-(methylthiomethyl)-1,3-dioxan-5-yl)methanamine A solution of benzyl ((4RS,5RS)-2,2-dimethyl-4-(methylthiomethyl)-1,3-dioxan-5-yl)methylcarbamate (200 mg, 589 μmol) and potassium hydroxide (992 mg, 1.77E+04 μmol) in isopropanol (8 mL) was heated under reflux for 2 h. Silica gel was added and the mixture was concentrated to dryness, then applied to a silica gel column and eluted with 5% MeOH/CH$_2$Cl$_2$, then 7% 7N NH$_3$/MeOH in CH$_2$Cl$_2$ to give ((4RS,5RS)-2,2-dimethyl-4-(methylthiomethyl)-1,3-dioxan-5-yl)methanamine (112 mg, 545 μmol, 93% yield) as a syrup. $^1$H NMR δ 3.96-3.83 (3H, m); 3.70 (1H, dd, J=9.9, 11.5 Hz); 2.83-2.73 (2H, m); 2.67-2.55 (2H, m); 2.18 (3H, s); 1.89-1.77 (1H, m); 1.44 (3H, s); 1.39 (3H, s). $^{13}$C NMR (CDCl$_3$) δ 98.8, 72.9, 62.8, 41.9, 41.4, 38.5, 29.3, 20.2, 17.3.

Example 10.9

Synthesis of (SR)-2-((RS)-2,2-dimethyl-1,3-dioxolan-4-yl)-N-methyl-3-(methylthio)propan-1-amine To a solution of benzyl (SR)-2-((RS)-2,2-dimethyl-1,3-dioxolan-4-yl)-3-(methylthio)propylcarbamate (210 mg, 619 μmol) in dry THF (5 mL) was added sodium hydride 60% (34.6 mg, 866 μmol) and then methyl iodide (77 μl, 1237 μmol) and the mixture was stirred RT under argon for 30 mins. Chloroform was added followed by water. Normal processing afforded a syrup. Potassium hydroxide (1.0 g, 1.78E+04 μmol) was added to this material in isopropanol (8 mL) and the resulting solution was heated under reflux for 5 h. Silica gel was added, the mixture was concentrated to dryness and applied to a silica column. Elution with 5% MeOH/CH$_2$Cl$_2$ and then 7% 7N NH3/MeOH in CH$_2$Cl$_2$ gave (SR)-2-((RS)-2,2-dimethyl-1,3-dioxolan-4-yl)-N-methyl-3-(methylthio)propan-1-amine (105 mg, 479 μmol, 77% yield) as a syrup. $^1$H NMR δ 4.19 (1H, dd, J=6.7, 13.4 Hz); 4.06 (1H, dd, J=6.3, 8.1 Hz); 3.70 (1H, dd, J=7.3, 8.0 Hz); 2.76 (1H, dd, J=4.4, 13.1 Hz); 2.70-2.56 (3H, m); 2.42 (3H, s); 2.12 (3H, s); 1.97-1.87 (1H, m); 1.40 (3H, s); 1.34 (3H, s). $^{13}$C NMR (CDCl$_3$) δ 109.0, 77.1, 68.0, 52.6, 42.2, 37.2, 34.5, 27.0, 25.7, 16.8.

Example 10.10

Synthesis of 1-((4RS,5RS)-2,2-dimethyl-4-(methylthiomethyl)-1,3-dioxan-5-yl)-N-methylmethanamine To a solution of benzyl ((4RS,5RS)-2,2-dimethyl-4-(methylthiomethyl)-1,3-dioxan-5-yl)methylcarbamate (82 mg, 242 μmol) in dry THF (1.5 mL) was added lithium aluminium hydride 2.0 M in THF (1208 μl, 2416 μmol) and the solution was stirred at RT for 18 h. Then water (0.12 mL), 15% NaOH (0.12 mL) and water (0.36 mL) were added carefully. The resulting mixture was filtered, the solids were washed with warm EtOAc and the filtrate was concentrated to dryness. Chromatography (5% MeOH in CH$_2$Cl$_2$, then 5% 7N NH$_3$/MeOH in CH$_2$Cl$_2$) gave 1-((4RS,5RS)-2,2-dimethyl-4-(methylthiomethyl)-1,3-dioxan-5-yl)-N-methylmethanamine (30 mg, 137 μmol, 56.6% yield) as a syrup. $^1$H. NMR (CDCl$_3$) δ 3.94-3.80 (2H, m); 3.69-3.62 (2H, m); 2.82 (1H, dd, J=2.9, 13.8 Hz); 2.64 (1H, dd, J=6.9, 13.8 Hz); 2.55 (1H, dd, J=4.7, 12.0 Hz); 2.44-2.38 (1H, m); 2.39 (3H, s); 2.18 (3H, s); 2.01-1.90 (1H, m); 1.44 (3H, s); 1.39 (3H, s). $^{13}$C NMR (CDCl$_3$) δ 99.1, 73.9, 63.6, 51.8, 39.5, 38.7, 37.5, 29.6, 20.3, 17.6.

Example 10.11

Synthesis of 7-(((((4RS,5RS)-2,2-dimethyl-4-(methylthiomethyl)-1,3-dioxan-5-yl)methyl)(methyl)amino)methyl)-5H-pyrrolo[3,2-d]pyrimidin-4-amine To a solution of 1-((4RS,5RS)-2,2-dimethyl-4-(methylthiomethyl)-1,3-dioxan-5-yl)-N-methylmethanamine (30 mg, 137 μmol) in dioxane (2 mL) and water (0.5 mL) was added 9-deazaadenine (27.5 mg, 205 μmol) and 37% aqueous formaldehyde (15.86 μl, 205 μmol). The reaction mixture was heated at 85° C. for 15 mins and then cooled and 7N NH$_3$/MeOH (2.5 mL) was added. The solution was allowed to stand at RT for 3 days and concentrated to dryness. Chromatography (10% 7N NH3/MeOH in CH$_2$Cl$_2$) gave 7-(((((4RS,5RS)-2,2-dimethyl-4-(methylthiomethyl)-1,3-dioxan-5-yl)methyl)(methyl)amino)methyl)-5H-pyrrolo[3,2-d]pyrimidin-4-amine (34 mg, 93 μmol, 68% yield) as a syrup. $^1$H NMR (CD$_3$OD) δ 8.16 (1H, s); 7.45 (1H, s); 3.86 (1H, dd, J=5.2, 11.9 Hz); 3.73-3.58 (3H, m); 3.52 (1H, dd, J=10.6, 11.7 Hz); 2.79 (1H, dd, J=2.5, 14.0 Hz); 2.53 (1H, dd, J=7.1, 14.0 Hz); 2.32 (1H, dd, J=5.5, 12.7 Hz); 2.24 (3H, s); 2.16 (1H, dd, J=8.1, 12.4 Hz); 2.06 (3H, s); 2.03-1.96 (1H, m); 1.36 (3H, s); 1.31 (3H. s). $^{13}$C NMR (CD$_3$OD) δ 152.6, 151.4, 147.8, 130.6, 115.7, 113.4, 100.1, 75.9, 64.7, 57.3, 52.4, 43.6, 39.3, 38.3, 29.9, 20.4, 17.4.

Example 10.12

Synthesis of (2RS,3RS)-2-(((((4-amino-5H-pyrrolo[3,2-d]pyrimidin-7-yl)methyl)(methyl)amino)methyl)-4-(methylthio)butane-1,3-diol To a solution of 7-(((((4RS,5RS)-2,2-dimethyl-4-(methylthiomethyl)-1,3-dioxan-5-yl)methyl)(methyl)amino)methyl)-5H-pyrrolo[3,2-d]pyrimidin-4-amine (34 mg, 93 μmol) in MeOH (2 mL) was added conc aq HCl (0.5 mL) and the solution was allowed to stand at RT for 2 h, then was concentrated to dryness. Chromatography (15% then 25% 7N NH$_3$/MeOH in CH$_2$Cl$_2$) gave (2RS,3RS)-2-(((((4-amino-5H-pyrrolo[3,2-d]pyrimidin-7-yl)methyl)(methyl)amino)methyl)-4-(methylthio)butane-1,3-diol (24 mg, 73.7 μmol, 79% yield) as a syrup. $^1$H NMR (CD$_3$OD) δ 8.16 (1H, s); 7.49 (1H, s); 3.83-3.75 (3H, m); 3.67 (1H, dd, J=5.0, 10.9 Hz); 3.56 (1H, dd, J=7.1, 10.8 Hz); 2.64 (2H, m); 2.57 (1H, dd, J=4.6, 13.6 Hz); 2.41 (1H, dd, J=8.3, 13.5 Hz); 2.34 (3H, s); 2.21-2.12 (1H, m); 2.04 (3H, s). $^{13}$C NMR (CD$_3$OD) δ 155.0, 154.0, 150.1, 133.2, 118.2, 115.3, 75.4, 66.3, 61.4, 54.8, 45.9, 45.6, 42.6, 18.9.

Example 11

Synthesis of (2S,3R)-1-(((4-amino-5H-pyrrolo[3,2]pyrimidin-7-yl)methyl)(methyl)amino)-4-(methylthio)butane-2,3-diol

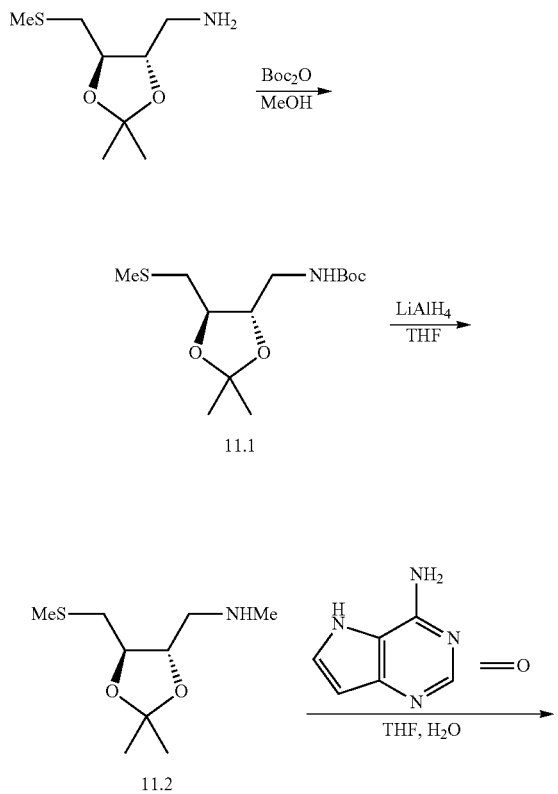

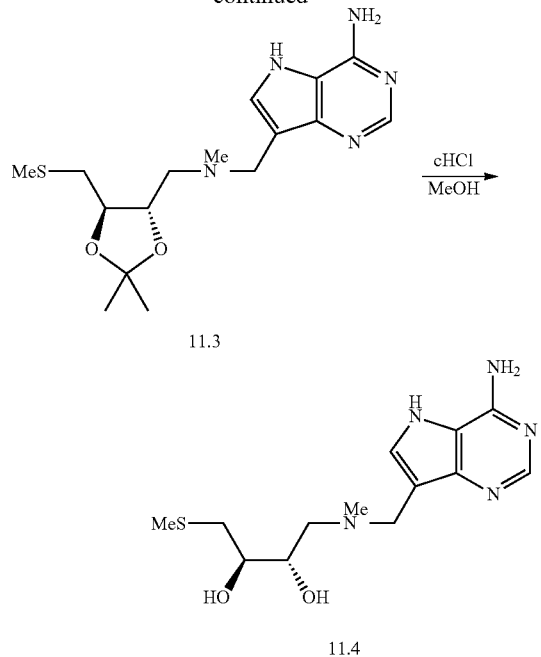

Example 11.1

Synthesis of tert-butyl((4S,5R)-2,2-dimethyl-5-(methylthiomethyl)-1,3-dioxolan-4-yl)methylcarbamate Di-tert-butyl dicarbonate (1.08 g, 4.9 mmol) was added portionwise to a solution of ((4R,5S)-2,2-dimethyl-5-(methylthiomethyl)-1,3-dioxolan-4-yl)methanamine (630 mg, 3.3 mmol) in methanol (10 ml, 3293 μmol) and the reaction monitored by TLC. After 10 minutes the reaction was complete therefore concentrate in vacuo. The residue was purified by flash chromatography on silica gel eluting with DCM=>5% MeOH/DCM to afford tert-butyl((4R,5S)-2,2-dimethyl-5-(methylthiomethyl)-1,3-dioxolan-4-yl)methylcarbamate (670 mg, 69.8%) as a syrup. $^1$H NMR (CDCl$_3$) δ 4.99 (brs, 1H), 3.91 (m, 2H), 3.47 (m, 2H), 3.31 (m, 1H), 2.72 (d, J=5.4 Hz, 2H), 2.18 (s, 3H), 1.45 (s, 9H), 1.41 (s, 6H). $^{13}$C NMR (CDCl$_3$) δ 156.7, 109.9, 80.4, 80.2, 78.1, 42.7, 37.3, 29.1, 27.9, 17.2.

Example 11.2

Synthesis of ((4S,5R)-2,2-dimethyl-5-(methylthiomethyl)-1,3-dioxolan-4-yl)-N-methylmethanamine Lithium aluminium hydride (3 ml, 2M in THF, 6.0 mmol) was added dropwise to a solution of tert-butyl((4R,5S)-2,2-dimethyl-5-(methylthiomethyl)-1,3-dioxolan-4-yl)methylcarbamate (620 mg, 2.1 mmol) in tetrahydrofuran (5 ml) and the resulting suspension heated to reflux and monitored by TLC. After 1 h at reflux the reaction appeared complete by TLC analysis therefore cool to ambient and quench with water (0.25 ml), 15% aq NaOH (0.25 ml), and water (0.75 ml) and stir the resulting white suspension for 30 minutes. The suspension was then filtered through Celite®, washed with hot ethyl acetate, and the filtrate concentrated in vacuo to afford a mobile oil. The residue was purified by flash chromatography on silica gel eluting with Purify the resulting oil by flash chromatography on silica gel eluting with 5% 7 N NH₃ in MeOH/DCM to afford ((4R,5S)-2,2-dimethyl-5-(methylthiomethyl)-1,3-dioxolan-4-yl)-N-methylmethanamine (330 mg, 76%) as a colourless oil. $^1$H NMR (CDCl₃) δ 3.94 (m, 2H), 2.85 (dd, J=12.3, 3.2 Hz, 1H), 2.75 (m, 3H), 2.47 (s, 3H), 2.18 (s, 3H), 1.41 (s, 3H), 1.41 (s, 3H). $^{13}$C NMR (CDCl₃) δ 109.4, 80.7, 79.0, 54.8, 37.6, 37.5, 28.1, 27.9, 17.3.

Example 11.3

Synthesis of 7-(((((4S,5R)-2,2-dimethyl-5-(methylthiomethyl)-1,3-dioxolan-4-yl)methyl)(methyl)amino)methyl)-5H-pyrrolo[3,2-d]pyrimidin-4-amine 9-Deazaadenine (73.4 mg, 0.55 mmol) was added to a solution of (S)-2-((R)-2,2-dimethyl-1,3-dioxolan-4-yl)-N-methyl-3-(methylthio)propan-1-amine (80 mg, 0.37 mmol) and formaldehyde (0.044 ml, 0.55 mmol) in a 1,4-dioxane (2 ml) and water (0.5 ml) mixture and the resulting suspension heated to 90 C (bath temp). After 1 h the reaction was complete by TLC, therefore cool to ambient, add 7N NH3 in MeOH (2.5 ml), and leave to stir for 1 h. The reaction was concentrated in vacuo and the residue purified by flash chromatography on silica gel, eluting with 10% 7N NH3 in MeOH/DCM=>20% 7N NH3 in MeOH/DCM, to presumably afford 7-(((((4S,5R)-2,2-dimethyl-5-(methylthiomethyl)-1,3-dioxolan-4-yl)methyl)(methyl)amino)methyl)-5H-pyrrolo[3,2-d]pyrimidin-4-amine (110 mg, 83%) which was committed to the next step without characterisation.

Example 11.4

Synthesis of (2S,3R)-1-(((4-amino-5H-pyrrolo[3,2-d]pyrimidin-7-yl)methyl)(methyl)amino)-4-(methylthio)butane-2,3-diol Concentrated hydrochloric acid (0.5 ml, 3.1 mmol) was added dropwise to a stirred solution of 7-(((((4R,5S)-2,2-dimethyl-5-(methylthiomethyl)-1,3-dioxolan-4-yl)methyl)(methyl)amino)methyl)-5H-pyrrolo[3,2-d]pyrimidin-4-amine (110 mg, 0.31 mmol) in methanol (10 ml). The reaction was immediately concentrated in vacuo to afford a crude residue which was purified by flash chromatography on silica gel, eluting with 20%.7N NH3 in methanol/DCM, to afford (2R,3S)-1-(((4-amino-5H-pyrrolo[3,2-d]pyrimidin-7-yl)methyl)(methylamino)-4-(methylthio)butane-2,3-diol (73 mg, 234 μmol, 74.9% yield) as a white solid. $^1$H NMR (CD₃OD) δ 8.17 (s, 1H), 7.48 (s, 1H), 3.91 (m, 1H), 3.88 (d, J=13.6 Hz, 1H), 3.78 (d, J=13.6 Hz, 1H), 3.65 (m, 1H), 2.62 (m, 4H), 2.33 (s, 3H), 2.08 (s, 3H). $^{13}$C NMR (CD₃OD) δ 152.5, 151.4, 147.6, 130.7, 115.7, 112.8, 73.7, 70.9, 60.8, 52.2, 43.4, 38.6, 16.4.

Example 12

Synthesis of (S)-2-((S)-1-(4-amino-5H-pyrrolo[3,2-d]pyrimidin-7-yl)-2-hydroxyethylamino)-3-(methylthio)propan-1-ol

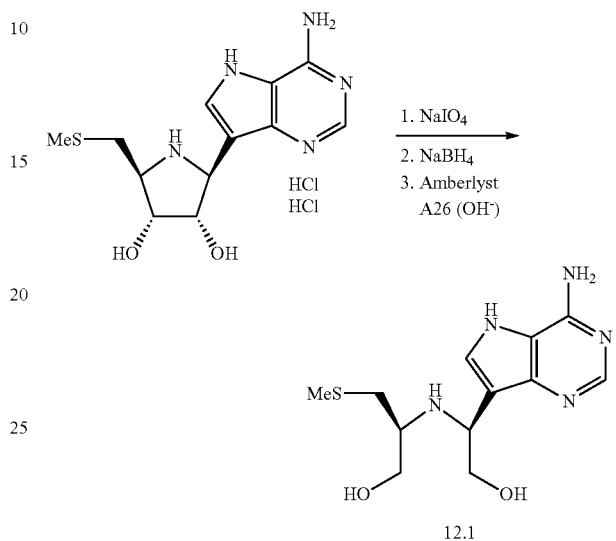

12.1

Example 12.1

Synthesis of (S)-2-((S)-1-(4-amino-5H-pyrrolo[3,2-d]pyrimidin-7-yl)-2-hydroxyethylamino)-3-(methylthio)propan-1-ol Sodium periodate (0.070 g, 0.326 mmol) was added to a solution of (2S,3S,4R,5S)-2-(4-amino-5H-pyrrolo[3,2-d]pyrimidin-7-yl)-5-(methylthiomethyl)pyrrolidine-3,4-diol dihydrochloride (0.1 g, 0.272 mmol, prepared according to G. B. Evans, R. H. Furneaux, V. L. Schramm, V. Singh, P. C. Tyler, J. Med. Chem., 2004, 47, 3275) in water (3 ml) and stirred at rt for 1 h. Sodium borohydride (0.051 g, 1.358 mmol) was added in small portions (vigorous reaction). The solution, which momentarily darkened then became almost colourless, was stirred for 15 mins. Silica gel was added and the solvent evaporated. The residue was chromatographed on silica gel (CH₂Cl₂-MeOH-28% aq. NH₄OH, 50:10:1) and the fractions containing product were evaporated to a gum (70 mg) which was dissolved in MeOH and passed through Amberlyst A26 (OH⁻) resin using MeOH as eluant. The solvent was evaporated to a yellow gum, dissolved in water and lyophilised to give (S)-2-((S)-1-(4-amino-5H-pyrrolo[3,2-d]pyrimidin-7-yl)-2-hydroxyethylamino)-3-(methylthio)propan-1-ol as a cream coloured solid (38 mg, 47%).

$^1$H NMR (CD₃OD) δ 8.14 (s, 1H), 7.54 (s, 1H), 4.26 (dd, J=6.5, 4.6 Hz, 1H), 3.85 (dd, J=10.9, 4.6 Hz, 1H), 3.77 (dd, J=10.9, 6.6 Hz, 1H), 2.77-2.66 (m, 1H), 2.64 (dd, J=13.4, 5.6 Hz, 1H), 2.41 (dd, J=13.3, 7.6 Hz, 1H), 1.72 (s, 3H). $^{13}$C NMR (CD₃OD, referenced to the centre line of CD₃OD at 49.0 ppm) δ 152.1, 150.7, 146.3, 128.8, 116.5, 115.5, 66.8, 63.5, 55.9, 54.5, 37.6, 15.1. +ESMS Found 320.1154 (M+Na)⁺ C₁₂H₁₉N₅NaO₂S requires 320.1157.

Example 13

Inhibition Studies

E. coli MTAN and human MTAP were obtained according to the reported methods (Singh, et al, *Biochemistry* 44, 11647-11659 (2005); Singh and Schramm *J. Am. Chem. Soc.* 128, 14691-14696 (2006). The MTAN gene sequences from *N. meningitides* MC58 and *H. pylori* J99 were amplified from genomic DNA (ATCC) and cloned into a modified pET-32 vector to direct high-level expression of MTAN with a non-cleavable N-terminal 6His tag. 1.5 L cultures of BL21(DE3) harbouring MTAN constructs were induced with 0.5 mM IPTG for 20 hours at 25° C. with vigorous shaking. Cell pellets were washed and lysed in 40 mL lysis buffer (25 mM HEPES, 0.5M NaCl, 10 mM imidazole pH 7.6, protease inhibitors and 0.25 mM TCEP) with the use of a cell disrupter at 15K psi. After removal of cell debris by centrifugation, the soluble cell lysates were loaded onto nickel-charged chelating sepharose (GE Healthcare) and washed with lysis buffer containing 20-150 mM imidazole. The 6His-MTANs were eluted in 250 mM imidazole, desalted using a Sephadex G-15 (GE Healthcare) gel filtration column, equilibrated with low salt buffer (100 mM HEPES, 30 mM KCL, pH 7.6) and concentrated to 40 mg/mL.

Inhibitor concentrations were obtained from the absorbance at 274 nm with extinction coefficient of 8.5 mM$^{-1}$ cm$^{-1}$ for 9-deazaadenine moiety.

Continuous spectrophotometric assays were used to characterize the inhibitors of the invention and in vivo inhibition of MTAP. The conversion of MTA into adenine was measured as a decrease in absorbance at 274 nm. At 274 nm, the difference in spectral properties is maximum and the millimolar extinction coefficient (cm$^{-1}$) is 1.6 for the conversion of MTA to adenine.

MTAN activities were assayed as reported previously (Singh et al (2006) *Biochemistry* 45, 12929-12941; Singh, et al (2005) *J. Biol. Chem.* 280, 18265-18273). Briefly, all experiments were carried out at 25° C., in 1 mL total reaction volume containing 100 mM HEPES buffer, pH 7.5 and 50 mM KCl with 5'-deoxymethylthioadenosine (MTA) as substrate. Kinetic constants ($k_{cat}$ and $K_m$) were determined by monitoring MTA hydrolysis at 274 nm where $\Delta\epsilon_{MTA}$=1.6 mM$^{-1}$ cm$^{-1}$. For measuring dissociation constant ($K_d$) of inhibitors, a xanthine oxidase-coupled assay was carried out. In this assay, saturating levels (1-2 mM) of MTA and various concentrations of inhibitor were mixed with xanthine oxidase (0.5 unit/mL), which is used to convert the MTAN product adenine to 2,8-dihydroxyadenine ($\epsilon_{2,8\text{-}dihydroxadenine}$=15.2 mM$^{-1}$ cm$^{-1}$ at 293 nm). Reactions were initiated by the addition of 8-10 nM MTAN, and the absorbance at 293 was monitored. Control experiments were carried out in the absence of either inhibitor or MTAN. Slow onset dissociation constants $K_d$ in the presence of more than 10-fold excessive inhibitor were obtained using the following equation:

$$v_s'/v_s = \frac{K_m + [S]}{K_m + [S] + K_m[I]/K_d}$$

where $v_s'$ and $v_s$ are steady state rates in the presence, and absence of inhibitor, respectively; $K_m$ is substrate Michaelis constant which was obtained as described above; [S] and [I] are the concentrations of the substrate MTA and inhibitor, respectively. If the concentration of inhibitor is smaller than 10-fold concentration of enzymes, the following correction was then applied:

$$I'=I-(1-v_0'/v_0)E_t$$

where I' is the effective inhibitor concentration; I is the concentration of inhibitor used in the assay; $v_0'$ and $v_0$ are initial rates in the presence, and absence of inhibitor, respectively; and $E_t$ is total MTAN concentration used in the assay. All data fitting was carried out with KaleidaGraph™ ver. 3.5 (Synergy Software).

TABLE 1

Inhibition constants with MTAP, *E. coli* MTAN, and *N. meningitides* MTAN.

Structure (Using Fischer projection formula)

| Example No | Configuration | R = | Kd vs MTAP | Kd vs E. coli MTAN | Kd vs N. meningitides MTAN |
|---|---|---|---|---|---|
| *Achiral amines* | | | | | |
| 1 | | 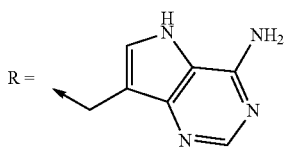 | 34 ± 24 nM | 5.8 ± 0.8 nM | 4 ± 2 nM |
| *Glycerol derivatives* | | | | | |
| 2 | L-glycero | 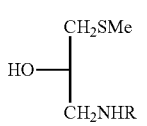 | 60 ± 8 nM | 4.0 ± 0.5 nM | 3.6 ± 0.4 nM |

TABLE 1-continued

Inhibition constants with MTAP, *E. coli* MTAN, and *N. meningitides* MTAN.

R = 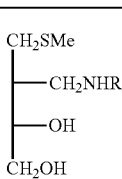

| Example No | Configuration | Structure (Using Fischer projection formula) | Kd vs MTAP | Kd vs E. coli MTAN | Kd vs N. meningitides MTAN |
|---|---|---|---|---|---|
| | | 2-Aminomethyl-2-deoxy-1-methylthio-tetritol derivatives | | | |
| 3 | DL-erythro | CH$_2$SMe — CH$_2$NHR — OH — CH$_2$OH | 34 ± 6 nM | 9 ± 2 nM | 5 ± 1 nM |
| 4 | N-Methyl-L-erythro | CH$_2$SMe — R(Me)NH$_2$C — HO — CH$_2$OH | 12 ± 2 nM | 2.3 ± 0.6 microM | 61 ± 5 nM |
| | | 3-Amino-3-deoxy-1-methylthio-tetritol derivatives | | | |
| 5 | D-erythro | CH$_2$SMe — OH — NHR — CH$_2$OH | 87 ± 8 nM | 10 ± 2 nM | 10 ± 1 nM |
| | L-erythro | CH$_2$SMe — HO — RHN — CH$_2$OH | 34 ± 18 nM | 2.1 ± 0.5 nM | 1.8 ± 0.4 nM |
| 6 | D-threo | CH$_2$SMe — HO — NHR — CH$_2$OH | 5.2 ± 0.4 nM | 0.8 ± 0.1 nM | 0.9 ± 0.1 nM |
| 7 | L-threo | CH$_2$SMe — OH — RHN — CH$_2$OH | 87 ± 11 nM | 3.9 ± 0.5 nM | 6 ± 1 nM |

TABLE 1-continued

Inhibition constants with MTAP, *E. coli* MTAN, and *N. meningitides* MTAN.

Structure (Using Fischer projection formula)

R = (7-deazaadenine-CH2- group, i.e., 4-amino-7H-pyrrolo[3,2-d]pyrimidin-7-yl methyl)

| Example No | Configuration | Structure | Kd vs MTAP | Kd vs *E. coli* MTAN | Kd vs *N. meningitides* MTAN |
|---|---|---|---|---|---|
| 8 | N-methyl-D-threo | CH2SMe / HO— / —N(Me)(R) / CH2OH | 88 ± 21 nM | 62 ± 5 nM | 19.3 ± 0.3 nM |

3-Aminomethyl-3-deoxy-1-methylthio-tetritol derivatives

| Example No | Configuration | Structure | Kd vs MTAP | Kd vs *E. coli* MTAN | Kd vs *N. meningitides* MTAN |
|---|---|---|---|---|---|
| 9 | DL-erythro | CH2SMe / —OH / —CH2NHR / CH2OH | 278 ± 27 nM | 25 ± 2 nM | 12.8 ± 0.9 nM |
| 10 | N-methyl-DL-erythro | CH2SMe / —OH / —CH2N(Me)R / CH2OH | 105 ± 30 nM | 65 ± 6 nM | 132 ± 9 nM |

4-Amino-4-deoxy-1-methylthio-tetritol derivatives

| Example No | Configuration | Structure | Kd vs MTAP | Kd vs *E. coli* MTAN | Kd vs *N. meningitides* MTAN |
|---|---|---|---|---|---|
| 11 | N-Methyl-D-erythro | CH2SMe / —OH / —OH / CH2N(Me)R | 368 ± 153 nM | 202 ± 35 nM | 85 ± 6 nM |

Other

| Example No | Configuration | Structure | Kd vs MTAP | Kd vs *E. coli* MTAN | Kd vs *N. meningitides* MTAN |
|---|---|---|---|---|---|
| 12 | | MeSH2C—CH(CH2OH)—NH—CH(CH2OH)—(4-amino-7H-pyrrolo[3,2-d]pyrimidin-7-yl) | 130 ± 20 nM | 154 ± 15 nM | 47 ± 4 nM |

Although the invention has been described by way of example, it should be appreciated the variations or modifications may be made without departing from the scope of the invention. Furthermore, when known equivalents exist to specific features, such equivalents are incorporated as if specifically referred to in the specification.

INDUSTRIAL APPLICABILITY

The invention relates to compounds that are inhibitors of MTAP and/or MATN. The compounds are therefore expected to be useful in the treatment of diseases in which the inhibition of MTAP or MTAN is desirable, particularly cancer.

The invention claimed is:
1. A compound of the formula (I):

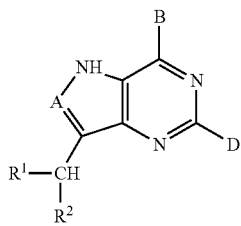

where:
$R^1$ is H or $NR^3R^4$;
$R^2$ is H or is an alkyl, alkenyl, alkynyl, aralkyl, aralkenyl, aralkynyl, or aryl group each of which is optionally substituted with one or more hydroxy, alkoxy, thiol, alkylthio, arylthio, aralkylthio, halogen, carboxylic acid, carboxylate alkyl ester, nitro, or $NR^3R^4$ groups, where each alkylthio, arylthio and aralkylthio group is optionally substituted with one or more alkyl, halogen, amino, hydroxy, or alkoxy groups;
provided that when $R^1$ is H, $R^2$ is an alkyl, alkenyl, alkynyl, aralkyl, aralkenyl, aralkynyl, or aryl group which is substituted with at least one $NR^3R^4$ group;
$R^3$ and $R^4$, independently of each other, is H or is an alkyl, alkenyl, alkynyl, aralkyl, aralkenyl, aralkynyl, or aryl group each of which is optionally substituted with one or more hydroxy, alkoxy, thiol, alkylthio, arylthio, aralkylthio, halogen, carboxylic acid, carboxylate alkyl ester, or nitro groups, where each alkylthio, arylthio and aralkylthio group is optionally substituted with one or more alkyl, halogen, hydroxy, or alkoxy groups;
A is or CH;
B is $NH_2$ or $NHR^5$,
$R^5$ is an alkyl, alkenyl, alkynyl, aralkyl, aralkenyl, aralkynyl, or aryl group, each of which is optionally substituted with one or more halogen or hydroxy groups; and
D is H, OH, $NH_2$, or $SCH_3$;
or a tautomer thereof, or a pharmaceutically acceptable salt thereof, or an ester thereof.

2. A compound as claimed in claim 1 where $R^1$ is H and $R^2$ is alkyl substituted with at least one $NR^3R^4$ group.

3. A compound as claimed in claim 1 where $R^3$ and $R^4$, independently of each other, are optionally substituted alkyl or H.

4. A compound as claimed in claim 3 where $R^3$ or $R^4$ is optionally substituted $C_1$-$C_5$ alkyl.

5. A compound as claimed in claim 4 where $R^3$ or $R^4$ is $C_1$-$C_5$ alkyl optionally substituted by one or more hydroxy groups.

6. A compound as claimed in claim 5 where $R^3$ or $R^4$ is hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxypentyl.

7. A compound as claimed in claim 4 where $R^3$ or $R^4$ is $C_1$-$C_5$ alkyl substituted by one or more hydroxy groups and/or one or more optionally substituted thiol, alkylthio, arylthio, or aralkylthio groups.

8. A compound as claimed in claim 7 where $R^3$ or $R^4$ is methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

9. A compound as claimed in claim 1 where $R^1$ is $NR^3R^4$, $R^3$ and $R^4$ are H, and $R^2$ is alkyl optionally substituted with one or more hydroxy, alkoxy, thiol, alkylthio, arylthio, aralkylthio, halogen, carboxylic acid, carboxylate alkyl ester, nitro, or $NR^3R^4$ groups, where each alkylthio, arylthio and aralkylthio group is optionally substituted with one or more alkyl, halogen, amino, hydroxy, or alkoxy groups.

10. A compound as claimed in claim 9 where $R^2$ is optionally substituted $C_1$-$C_5$ alkyl.

11. A compound as claimed in claim 10 where $R^2$ is $C_1$-$C_5$ alkyl optionally substituted by one or more hydroxy groups.

12. A compound as claimed in claim 11 where $R^2$ is hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxypentyl.

13. A compound as claimed in claim 10 where $R^2$ is $C_1$-$C_5$ alkyl substituted by one or more hydroxy groups and/or one or more optionally substituted thiol, alkylthio, arylthio, or aralkylthio groups.

14. A compound as claimed in claim 13 where $R^2$ is methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

15. A compound as claimed in claim 1 where $R^1$ is $NR^3R^4$, $R^3$ is H, $R^4$ is alkyl optionally substituted with one or more hydroxy, alkoxy, thiol, alkylthio, arylthio, aralkylthio, halogen, carboxylic acid, carboxylate alkyl ester, nitro, or nitro groups, where each alkylthio, arylthio and aralkylthio group is optionally substituted with one or more alkyl, halogen, hydroxy, or alkoxy groups, and $R^2$ is H.

16. A compound as claimed in claim 15 where $R^4$ is optionally substituted $C_1$-$C_5$ alkyl.

17. A compound as claimed in claim 16 where $R^4$ is $C_1$-$C_5$ alkyl optionally substituted by one or more hydroxy groups.

18. A compound as claimed in claim 17 where $R^4$ is hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxypentyl.

19. A compound as claimed in claim 16 where $R^4$ is $C_1$-$C_5$ alkyl substituted by one or more hydroxy groups and/or one or more optionally substituted thiol, alkylthio, arylthio, or aralkylthio groups.

20. A compound as claimed in claim 19 where $R^4$ is methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

21. A compound as claimed in claim 1 where $R^1$ is $NR^3R^4$, $R^3$ is H, $R^4$ and $R^2$ are alkyl optionally substituted with one or more hydroxy, alkoxy, thiol, alkylthio, arylthio, aralkylthio, halogen, carboxylic acid, carboxylate alkyl ester, or nitro groups, where each alkylthio, arylthio and aralkylthio group is optionally substituted with one or more alkyl, halogen, hydroxy, or alkoxy groups.

22. A compound as claimed in claim 21 where $R^2$ or $R^4$ is optionally substituted $C_1$-$C_5$ alkyl.

23. A compound as claimed in claim 22 where $R^2$ or $R^4$ is $C_1$-$C_5$ alkyl optionally substituted by one or more hydroxy groups.

24. A compound as claimed in claim 23 where $R^2$ or $R^4$ is hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxypentyl.

25. A compound as claimed in claim 22 where $R^2$ or $R^4$ is $C_1$-$C_5$ alkyl substituted by one or more hydroxy groups and/or one or more optionally substituted thiol, alkylthio, arylthio, or aralkylthio groups.

26. A compound as claimed in claim 25 where $R^2$ or $R^4$ is methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

27. A compound as claimed in claim 1 where $R^1$ is $NR^3R^4$, $R^3$ and $R^4$ are each alkyl optionally substituted with one or more hydroxy, alkoxy, thiol, alkylthio, arylthio, aralkylthio, halogen, carboxylic acid, carboxylate alkyl ester, or nitro groups, where each alkylthio, arylthio and aralkylthio group is optionally substituted with one or more alkyl, halogen, amino, hydroxy, or alkoxy groups, and $R^2$ is H.

28. A compound as claimed in claim 27 where $R^3$ or $R^4$ is optionally substituted $C_1$-$C_5$ alkyl.

29. A compound as claimed in claim 28 where $R^3$ or $R^4$ is $C_1$-$C_5$ alkyl optionally substituted by one or more hydroxy groups.

30. A compound as claimed in claim 29 where $R^3$ or $R^4$ is hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxypentyl.

31. A compound as claimed in claim 28 where $R^3$ or $R^4$ is $C_1$-$C_5$ alkyl substituted by one or more hydroxy groups and/or one or more optionally substituted thiol, alkylthio, arylthio, or aralkylthio groups.

32. A compound as claimed in claim 31 where $R^3$ or $R^4$ is methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

33. A compound as claimed in claim 1 where B is $NH_2$.

34. A compound as claimed in claim 1 where D is H or $NH_2$.

35. A compound as claimed in claim 1 where D is OH or $SCH_3$.

36. A compound that is:
2-amino-7-(2,3-dihydroxy-1-(2-(methylthio)ethylamino)propyl)-4-amino-5H-pyrrolo[3,2-d]pyrimidine;
7-(2,3-dihydroxy-1-(2-(methylthio)ethylamino)propyl)-4-amino-5H-pyrrolo[3,2-d]pyrimidine;
2-amino-7-(1-amino-2,3-dihydroxy-5-(methylthio)pentyl)-4-amino-5H-pyrrolo[3,2-d]pyrimidine;
7-(1-amino-2,3-dihydroxy-5-(methylthio)pentyl)-4-amino-5H-pyrrolo[3,2-d]pyrimidine;
2-amino-7-(2-hydroxy-1-(1-hydroxy-3-(methylthio)propan-2-ylamino)ethyl)-4-amino-5H-pyrrolo[3,2-d]pyrimidine;
7-(2-hydroxy-1-(1-hydroxy-3-(methylthio)propan-2-ylamino)ethyl)-4-amino-5H-pyrrolo[3,2-d]pyrimidine;
2-amino-7-((3,4-dihydroxy-1-(methylthio)butan-2-ylamino)methyl)-4-amino-5H-pyrrolo[3,2-d]pyrimidine;
7-((3,4-dihydroxy-1-(methylthio)butan-2-ylamino)methyl)-4-amino-5H-pyrrolo[3,2-d]pyrimidine;
2-amino-7-(((2-hydroxy-4-(methylthio)butyl)(methyl)amino)methyl)-4-amino-5H-pyrrolo[3,2-d]pyrimidine;
7-(((2-hydroxy-4-(methylthio)butyl)(methyl)amino)methyl)-4-amino-5H-pyrrolo[3,2-d]pyrimidine;
2-amino-7-((2-hydroxy-4-(methylthio)butylamino)methyl)-4-amino-5H-pyrrolo[3,2-d]pyrimidine;
7-((2-hydroxy-4-(methylthio)butylamino)methyl)-4-amino-5H-pyrrolo[3,2-d]pyrimidine;
2-amino-7-((3,4-dihydroxy-2-(methylthiomethyebutylamino)methyl)-4-amino-5H-pyrrolo[3,2-d]pyrimidine;
7-((3,4-dihydroxy-2-(methylthiomethyebutylamino)methyl)-4-amino-5H-pyrrolo[3,2-d]pyrimidine;
2-amino-7-((3-hydroxy-2-(methylthiomethyl)propylamino)methyl)-4-amino-5H-pyrrolo[3,2-d]pyrimidine;
7-((3-hydroxy-2-(methylthiomethyl)propylamino)methyl)-4-amino-5H-pyrrolo[3,2-d]pyrimidine;
7-(((3-hydroxy-2-(methylthiomethyl)propyl)(methyl)amino)methyl)-4-amino-5H-pyrrolo[3,2-d]pyrimidine;
2-amino-7-(((3-hydroxy-2-(methylthiomethyl)propyl)(methyl)amino)methyl)-4-amino-5H-pyrrolo[3,2-d]pyrimidine;
2-((4-amino-5H-pyrrolo[3,2-d]pyrimidin-7-yl)methylamino)-2-(methylthiomethyl)propane-1,3-diol;
(S)-1-((4-amino-5H-pyrrolo[3,2-d]pyrimidin-7-yl)methylamino)-3-(methylthio)propan-2-ol;
(R)-4-amino-5H-pyrrolo[3,2-d]pyrimidin-7-yl)methylamino)-3-(methylthio)propan-2-ol;
(2R,3S)-4-[(4-amino-5H-pyrrolo[3,2-d]pyrimidin-7-yl)methylamino]-3-(methylthiomethyl)butane-1,2-diol;
(2R,3S)-4-[(4-amino-5H-pyrrolo[3,2-d]pyrimidin-7-yl)methylamino]-3-(methylthiomethyl)butane-1,2-diol;
(2R,3S)-4-[(4-amino-5H-pyrrolo[3,2-d]pyrimidin-7-yl)methylamino]-3-(methylthiomethyl)butane-1,2-diol;
(2R,3S)-4-[(4-amino-5H-pyrrolo[3,2-d]pyrimidin-7-yl)methylamino]-3-(methylthiomethyl)butane-1,2-diol;
(2R,3R)-4-(((4-amino-5H-pyrrolo[3,2-d]pyrimidin-7-yl)methyl)(methyl)amino)-3-(methylthiomethyl)butane-1,2-diol;
(2R,3S)-4-(((4-amino-5H-pyrrolo[3,2-d]pyrimidin-7-yl)methyl)(methyl)amino)-3-(methylthiomethyl)butane-1,2-diol;
(2R,3S)-4-(((4-amino-5H-pyrrolo[3,2-d]pyrimidin-7-yl)methyl)(methyl)amino)-3-(methylthiomethyl)butane-1,2-diol;

(2R,3R)-4-(((4-amino-5H-pyrrolo[3,2-d]pyrimidin-7-yl)methyl)(methyl)amino)-3-(methylthiomethyl) butane-1,2-diol;
(2R,3R)-2-((4-amino-5H-pyrrolo[3,2-d]pyrimidin-7-yl)methylamino)-4-(methylthio)butane-1,3-diol;
(2R,3S)-2-((4-amino-5H-pyrrolo[3,2-d]pyrimidin-7-yl)methylamino)-4-(methylthio)butane-1,3-diol;
(2R,3S)-2-((4-amino-5H-pyrrolo[3,2-d]pyrimidin-7-yl)methylamino)-4-(methylthio)butane-1,3-diol;
(2R,3R)-2-((4-amino-5H-pyrrolo[3,2-d]pyrimidin-7-yl)methylamino)-4-(methylthio)butane-1,3-diol;
(2R,3R)-2-(((4-amino-5H-pyrrolo[3,2-d]pyrimidin-7-yl)methyl)(methyl)amino)-4-(methylthio)butane-1,3-diol;
(2S,3S)-2-(((4-amino-5H-pyrrolo[3,2-d]pyrimidin-7-yl)methyl)(methyl)amino)-4-(methylthio)butane-1,3-diol;
(2R,3S)-2-(((4-amino-5H-pyrrolo[3,2-d]pyrimidin-7-yl)methyl)(methyl)amino)-4-(methylthio)butane-1,3-diol;
(2R,3R)-2-(((4-amino-5H-pyrrolo[3,2-d]pyrimidin-7-yl)methyl)(methyl)amino)-4-(methylthio)butane-1,3-diol;
(2R,3R)-2-{[(4-amino-5H-pyrrolo[3,2-d]pyrimidin-7-yl)methylamino]methyl}-4-(methylthio)butane-1,3-diol;
(2R,3S)-2-{[(4-amino-5H-pyrrolo[3,2-d]pyrimidin-7-yl)methylamino]methyl}-4-(methylthio)butane-1,3-diol;
(2R,3S)-2-{[(4-amino-5H-pyrrolo[3,2-d]pyrimidin-7-yl)methylamino]methyl}-4-(methylthio)butane-1,3-diol;
(2S,3R)-2-{[(4-amino-5H-pyrrolo[3,2-d]pyrimidin-7-yl)methylamino]methyl}-4-(methylthio)butane-1,3-diol;
(2R,3R)-1-(((4-amino-5H-pyrrolo[3,2-d]pyrimidin-7-yl)methyl)(methyl)amino)-4-(methylthio)butane-2,3-diol;
(2S,3S)-1-(((4-amino-5H-pyrrolo[3,2-d]pyrimidin-7-yl)methyl)(methyl)amino)-4-(methylthio)butane-2,3-diol;
(2R,3S)-1-(((4-amino-5H-pyrrolo[3,2-d]pyrimidin-7-yl)methyl)(methyl)amino)-4-(methylthio)butane-2,3-diol;
(2S,3R)-1-(((4-amino-5H-pyrrolo[3,2-d]pyrimidin-7-yl)methyl)(methyl)amino)-4-(methylthio)butane-2,3-diol;
(R)-2-((R)-1-(4-amino-5H-pyrrolo[3,2-d]pyrimidin-7-yl)-2-hydroxyethylamino)-3-(methylthio)propan-1-ol;
(S)-2-((S)-1-(4-amino-5H-pyrrolo[3,2-d]pyrimidin-7-yl)-2-hydroxyethylamino)-3-(methylthio)propan-1-ol;
(R)-2-((S)-1-(4-amino-5H-pyrrolo[3,2-d]pyrimidin-7-yl)-2-hydroxyethylamino)-3-(methylthio)propan-1-ol; or
(S)-2-((R)-1-(4-amino-5H-pyrrolo[3,2-d]pyrimidin-7-yl)-2-hydroxyethylamino)-3-(methylthio)propan-1-ol.

37. A pharmaceutical composition comprising a pharmaceutically effective amount of a compound of claim 1.

* * * * *

UNITED STATES PATENT AND TRADEMARK OFFICE
CERTIFICATE OF CORRECTION

PATENT NO. : 8,383,636 B2
APPLICATION NO. : 12/310597
DATED : February 26, 2013
INVENTOR(S) : Kieth Clinch et al.

Page 1 of 1

It is certified that error appears in the above-identified patent and that said Letters Patent is hereby corrected as shown below:

ON THE TITLE PAGE:

In item (75), Inventors, change

"Shivall Ashwah Ashwin Gulab" to --Shivali Ashwin Gulab--

Signed and Sealed this
Fourth Day of June, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,383,636 B2 | Page 1 of 1 |
| APPLICATION NO. | : 12/310597 | |
| DATED | : February 26, 2013 | |
| INVENTOR(S) | : Keith Clinch et al. | |

It is certified that error appears in the above-identified patent and that said Letters Patent is hereby corrected as shown below:

In the Specification

Column 1, lines 15-21, should read:

-- STATEMENT OF GOVERNMENT SUPPORT

This invention was made with government support under grant number GM041916 awarded by the National Institutes of Health. The government has certain rights in the invention. --

Signed and Sealed this
Twenty-ninth Day of December, 2015

Michelle K. Lee
*Director of the United States Patent and Trademark Office*